US012751426B2

(12) United States Patent
Pawlick

(10) Patent No.: US 12,751,426 B2
(45) Date of Patent: Oct. 6, 2026

(54) ANIMAL HEALTH AND SAFETY SYSTEM AND METHOD

(71) Applicant: EQUINE SAFETY INC., Reno, NV (US)

(72) Inventor: Harvey Pawlick, Reno, NV (US)

(73) Assignee: EQUINE SAFETY INC., Reno, NV (US)

( * ) Notice: Subject to any disclaimer, the term of this patent is extended or adjusted under 35 U.S.C. 154(b) by 0 days.

(21) Appl. No.: 19/255,586

(22) Filed: Jun. 30, 2025

(65) Prior Publication Data

US 2025/0324949 A1 Oct. 23, 2025

Related U.S. Application Data

(63) Continuation of application No. 19/009,168, filed on Jan. 3, 2025, now Pat. No. 12,376,570, which is a continuation-in-part of application No. 18/201,606, filed on May 24, 2023, now Pat. No. 12,225,886.

(60) Provisional application No. 63/473,540, filed on Jun. 3, 2022.

(51) Int. Cl.
*A01K 29/00* (2006.01)
*G16H 50/20* (2018.01)

(52) U.S. Cl.
CPC ........... *A01K 29/005* (2013.01); *G16H 50/20* (2018.01)

(58) Field of Classification Search
CPC ....... A01K 29/00; A01K 29/005; G16H 50/20
See application file for complete search history.

(56) References Cited

U.S. PATENT DOCUMENTS

| | | | |
|---|---|---|---|
| 4,852,336 | A | 8/1989 | Gammill |
| 5,848,576 | A | 12/1998 | Colaianni |
| 6,081,607 | A | 6/2000 | Mori |
| 6,910,050 | B2 | 6/2005 | Pawlick |
| 7,649,465 | B1 | 1/2010 | Vogel |
| 8,830,068 | B2 | 9/2014 | Campbell |
| 9,538,728 | B2 | 1/2017 | Womble et al. |

(Continued)

FOREIGN PATENT DOCUMENTS

AU 2020102206 A4 10/2020

OTHER PUBLICATIONS www.ebay.com/itm/https://chn=ps&var=601930839867&norover=1&mkevt=1&mkrid=711-117182-37290-0&mkcid=2&mkscid=101&itemid=601930839867_302982505599&targetid=1262749492542&device=c&mktype=&googleloc=9004032&poi=&campaignid=14859008593&mkgroupid=130497710760&rlsatarget=pla-1262749492542&abcld=9300678&merchantid=6478414&gclid=EAlalQobChMlofDytKiJ; originally accessed Apr. 19, 2023; pp. 3.

(Continued)

*Primary Examiner* — Monica L Perry
*Assistant Examiner* — Aaron M Rodziwicz
(74) *Attorney, Agent, or Firm* — Nixon Peabody LLP

(57) ABSTRACT

A human or artificial intelligence (AI) operated animal health and safety system and method are described for use with living, individually identified animals, such as equines, other ungulates, canines and felines. Sensors/monitors/signs and sources ("DMSS") obtain data on vital life-sustaining or life-threatening processes and signs directly from the animal. The vital life-sustaining and/or life-threatening processes and signs in the form of data, together with archived/real-time location/monitoring/external conditions, e.g., weather forecasts/alerts are processed in a system which can be operated partially, or almost exclusively by AI. The AI system and method re-purposes/re-re-purposes the data (Continued)

originally obtained for another use/diagnosis or purpose. A method of utilizing the AI system is also described.

23 Claims, 16 Drawing Sheets

(56) References Cited

U.S. PATENT DOCUMENTS

| | | | | |
|---|---|---|---|---|
| 9,936,680 | B2 | 4/2018 | Womble et al. | |
| 10,041,843 | B2 | 8/2018 | Zakharov et al. | |
| 10,049,278 | B2 | 8/2018 | Womble et al. | |
| 10,555,498 | B2 | 2/2020 | Womble et al. | |
| 10,986,817 | B2 * | 4/2021 | Singh | A01K 11/004 |
| 11,071,279 | B2 * | 7/2021 | Singh | A01K 11/008 |
| 11,457,614 | B2 * | 10/2022 | Maher | A01K 27/008 |
| 11,564,572 | B2 * | 1/2023 | Maher | A61B 5/0008 |
| 11,960,957 | B2 * | 4/2024 | Mitchell | A01K 11/006 |
| 12,099,893 | B2 * | 9/2024 | Kreuscher | G06K 7/10366 |
| 12,144,320 | B2 * | 11/2024 | Bateman | A01K 11/006 |
| 12,193,413 | B2 * | 1/2025 | Wilkinson | A01K 1/0613 |
| 12,213,449 | B2 * | 2/2025 | Fichman | H04W 4/38 |
| 12,239,098 | B2 * | 3/2025 | Wilkinson | A01K 11/006 |
| 12,409,474 | B2 * | 9/2025 | Gyde | B06B 1/067 |
| 2004/0230607 | A1 | 11/2004 | Pawlick | |
| 2007/0221140 | A1 | 9/2007 | Warren et al. | |
| 2010/0111600 | A1 | 5/2010 | De Bien | |
| 2012/0108989 | A1 | 5/2012 | Gargiulo et al. | |
| 2012/0226751 | A1 | 9/2012 | Schwaderer | |
| 2014/0352632 | A1 | 12/2014 | Mclaughlin | |
| 2015/0334994 | A1 | 11/2015 | Prasad | |
| 2016/0063188 | A1 | 3/2016 | Thornberry et al. | |
| 2017/0095206 | A1 | 4/2017 | Leib et al. | |
| 2018/0098523 | A1 | 4/2018 | Basom | |
| 2019/0254599 | A1 * | 8/2019 | Young | A61B 5/14532 |
| 2019/0392200 | A1 | 12/2019 | Polimeno et al. | |
| 2020/0113728 | A1 | 4/2020 | Spector et al. | |
| 2020/0359605 | A1 | 11/2020 | Maher et al. | |

OTHER PUBLICATIONS https://www.twohorsetack.com/p-1865-beta-biothane-affordable-beginner-harness.aspx?gclid=EAlalQobChMI5JSxjaeJ_wlVeQFMCh0BiQDcEAQYASABEgK5nPD_BWEEbay; Beta Biothane Affordable Beginner Harness; originally accessed Apr. 19, 2023; pp. 4.

https://www.nature.com/articles/d41586-019-02143-0 Nature 571, 319-321 (2019) Comment Jul. 18, 2019, originally accessed Dec. 10, 2021; pp. 3.

https://apple.news; "How Health and Fitness Trackers are About to Get a lot More Granular" / AgtMj12RATNWXP_ZmYyUYng originally accessed Jan. 12, 2022; pp. 12.

Libby Schultz; "Innovating Til the Cows Come Home"; AJ Park; Feb. 8, 2023; pp. 3.

* cited by examiner

ANIMAL HEALTH AND SAFETY SYSTEM AND METHOD

CROSS-REFERENCE TO RELATED APPLICATIONS

This application is a Continuation of U.S. Non-provisional patent application Ser. No. 19/009,168, filed Jan. 3, 2025; which in turn is a Continuation-in-Part ("CIP") of U.S. Non-provisional application Ser. No. 18/201,606, filed May 24, 2023; which in turn claims benefit of domestic priority of Provisional application Ser. No. 63/473,540, filed Jun. 3, 2022, the entire disclosures of each of which are herein incorporated by reference in their entireties.

BACKGROUND

1. Field of the Invention

Please consider the likes of animals, such as Kentucky Derby Horses, worth millions of dollars and often with syndicated ownerships; would not owners like to know . . . their animals' vital signs and healthy ranges, the ambient temperatures in the stables and out on the training track, the animal's location and exercise regimens?

For example, consider the "winning" (later disqualified) 2021 Kentucky Derby Horse, Medina Spirit; with his health and safety comprehensively monitored and reported, per the following Equine Health and Safety disclosure, likely Medina's ailment would have been monitored, discovered and treated, with Medina put out-to-stud, thereby preserving this valuable equine asset, delivering to the owners a continuing income stream. Sadly . . . Medina Spirit died suddenly during a light work out on the Santa Anita Race Track . . . ownership's equine asset lost to health and safety risks . . . risks addressed by the Animal Safety System of this disclosure. While there may have been some monitors or sensors placed on, or in, an animal during diagnostic testing (e.g., painlessly by a veterinarian per anesthesia), this disclosure is directed to obtaining, from at least one sensor on, in, or otherwise combined with halter/harness/hackamore/bridles, or other trappings as associated with equines, as well as other animals, such as canines and/or felines, or borne by the animal itself (such as a sensor attached directly to the skin of an animal), to generate data from an animal's real time conditions and/or signs, and, if required, amplifying, and then transmitting data to a location remote from the animal, to either be archived and/or acted upon by human intervention, in response to the data.

2. Summary of the Related Art

Halters and hackamores both lack bits and are generally known in the form of a noseband, and a headpiece that buckles around a head of a horse and can be made of various materials, such as rope, leather, or synthetic materials and combinations thereof. The headpiece fits around the poll and behind both ears/around the neck, and the noseband fits around the muzzle. The noseband and headpiece portions of the halter can be suitably joined to each other by straps of leather, rope, or other suitable materials, running alongside the jaw and cheekbone on either side of the head, as well as a lower strap running from the headpiece below the jaw to just below the chin groove to secure the noseband and headpiece portions together. The various portions of the halter/hackamore can be joined to each other by various means, including sewing, rivets, buckles, metal hoops, and other fasteners. A hoop, or other fitment, can be provided on the noseband and/or lower strap in the vicinity of the chin groove for the purpose of attaching a lead rope. Add a bit to a halter and it typically is termed a bridle, exceptions stated but not limited to text following. A bit in combination with a halter, and/halter-bridle per disclosure text following is within the scope of the halters of the present disclosure.

Halter "nameplates" have also been suggested for placement on a halter, hackamore and/or bridle, the nameplate(s) bearing various indicia thereon. Such indicia may include the horse's name, the owner's identity and/or contact information, or a stable's name, and similar care and custody information and authorizations. The indicia or information carried by these nameplates are fixed at the time of attaching the nameplate to the halter and cannot readily be altered thereafter except by attaching another and/or substitute nameplate with updated indicia thereon. However, as discussed hereinbelow, "Medallions" as disclosed herein, may not only disclose the indicia as heretofore associated with nameplates, but can also provide smart device communications, communication connection codes, information, numbers and symbols, and other indicia far exceeding previous nameplates known in the art.

While halters of various types as bridles have been used for centuries, the functions of such previous halters have been limited to provide a suitable device for controlling movement of the horse during handling. Thus, there has not been any innovation in the form or function of a halter for equine use until the present disclosure.

"Halters," "hackamores," "bridles" are terms utilized in disclosure inclusive terminology in the specification described and illustrated herein. Halters are as likely as old an innovation as animal domestication itself. Also, halter, hackamore and bridle terminology, usage and functions often inclusively overlap, a main operational difference between halter and bridle being . . . the halter is more often used for a walking person to lead or tether a canine/feline and mostly an equine animal, and a bridle-hackamore is more often used by an animal rider to control the ridden equine. The term bridle is also primarily used to describe the device that holds a bit in the mouth of the horse; halters and hackamores generally lack bits. The bridle-halter distinction may overlap, e.g., the Royal Canadian Mounted Police et al. use a halter bridle, that on rest-stops facilitates removing the bit and reins from the horse, without removing the bridle; thus, the terminologies overlap, as most halters do not have bits. As both hackamore horse headgear, and halter headgear, (mostly) lack bits, and are of highly similar-to-same basic design & structure, thereby a hackamore may be seen as an inclusive type of specialized equine halter, thereby fully including hackamores in halter disclosures; as bridles also share commonalities with hackamores, hackamores are also fully included with bridle disclosures, per the following Halters, Hackamores and Bridles disclosure. Hackamores lacking bits, as bridles using bits, are both used for riders' control of equines. Yet while a hackamore gives the rider control of the horse through the nose band aka bosal, by using pressure points on the horse's chin, face and nose, and lacks a bit . . . bridles exert rider control of the horse via a bit. Also overlapping in usage . . . a bosal may also refer to a versatile type of hackamore, more so in the western United States, sourced from Spanish colonial equestrian traditions.

Halter-hackamore-bridle—include the inclusive disclosure of relevant tack terminology: Crownpiece aka headpiece . . . cheekpieces . . . poll . . . reins . . . bit . . . Weymouth double-bit bridle . . . snaffle bridle . . . Pelham bridle . . . western bridle . . . barcoo bridle gag bridle . . . halter bridle . . . figure eight bridle . . . jaquima hackamore . . . mechanical hackamore . . . bosal hackamore . . . fiador hackamore . . . mecate rein . . . harness bridle . . . blinders-blinkers-winkers . . . throatlatch-throatlash . . . browband . . . noseband . . . cavesson . . . sliphead . . . frentera bit and bradoon/four reins . . . curb strap . . . bit hobble . . . check rein . . . shank hobble . . . phalerae . . . sallongs. Key Shared Commonalities/Differences—Halters-Hackamores-Bridles 1) Shared—hackamores (FIG. 1-I), and bridles (FIG. 1-H), provide the equine rider control of the horse.
1) Difference—halters (FIG. 1 A-B) provide a walking person a means to lead an animal, small animals too, e.g. canines, felines, etc., yet mostly larger ungulates; halters are not used for rider control of equines/animals.
2) Shared—bridle riders, and hackamore riders (FIG. 1-I), use reins for equine control. 2) Difference—halter walkers use a hoop (FIGS. 1 A, B-46) and lead/rope (FIG. 1 B-53) for animal control
3) Shared—halters (FIGS. 1 A, B) and hackamores FIG. 1I) do not use bits for animal control . . . are typically without bits, exceptions below:
3) Difference—bridles use bits (FIG. 1 H-47) for rider control of an equine.

Shared—halter bridles, (also termed an endurance bridle or trail bridle) e.g., used by the RCMP (Royal Canadian Mounted Police), Queens Household Cavalry, etc., represent exceptions to the general halter-no-bit and bridle-bit distinction . . . RCMP halter bridles, and similar halter bridles, having quick-release cheekpieces that hold the bit and reins, for no-mouth-bit equine watering, feeding, and rest when tack-n-saddled-up for duty. Such is a source of hybrid halters-with-bits.

4) Shared—halters, hackamores and bridles use behind-the-ears crownpieces/headpieces (FIGS. 1 A, B, H, I-42) running over the horse's poll, connecting the strap/rope around-the-neck-head-throat juncture, (a headpiece throatlatch per FIGS. 1 H-42, I-42), an exception being the bosal-style hackamore that lacks a throatlatch, the bosal-style headpiece/strap typically running along both equine cheeks, connecting to the noseband.
4) Shared—halters, hackamores and bridles use side-of-head straps (also rolled or rope material), often termed cheekpieces, (FIGS. 1 A, B, H, I-43/44) connecting the headpiece to the noseband-muzzle.
5) Shared—halters, hackamores and bridles use a noseband, (FIGS. 1 A, B. H, I-41). Thus, applicant notes 7 commonalities of halters, hackamores and bridles, versus 3, often-overlapping differences, disclosing a single inclusive device group by shared animal control application, function, purpose and use.

SUMMARY OF THE INVENTION

Introduction: The following animal bodily systems and/or methods are included in the Animal Health and Safety System and Method; the animal bodily processes/systems inclusively supplement ownerships/designates/veterinarians Animal Safety System usage. Painlessly per veterinarian-anesthesia devices-monitors-sensors are implanted, and/or ingested, and/or inserted, and/or borne by the animal per the stable-tack device-means defined by this disclosure, and-or communicated to computers-devices remote from the animal. Such information is communicated directly, and/or via signal-booster, from the animal, via all smart-sending-receiving communicating and re-communicating devices, equipment, such as antennas, etc. and manners, e.g., frequencies, microwaves, etc. The animals' device-monitored-sensed data-information, is communicated to smart computerized records of ownerships, designates, veterinarians, platforms, programs, and research-other institutions; devices-monitors-sensors-sources ("DMSS"), generate data-information, communicated directly and/or signal boosted, and/or analyzed-read-interpreted-deciphered by communicating smart devices on-animal, in-animal-body, and/or remote sources from the animal, singularly and per interfaced-integrated platform(s)-programs(s) combination(s). Sources may include various animal-health-safety-life-threatening conditions, e.g., sepsis sensed to tornados-forecast. Communication devices include smart phones-wearables-tablets-laptops-computers, plus communications-signal-boosters and medallions, as defined in this disclosure as smart devices. Animal health and safety bodily processes and systems may be monitored and/or sensed and/or communicated and/or treated in situ=on the animal, and/or in the field, via the present Health and Safety System usage; in situ Health and Safety System usage and/or data-monitorings/sensings and/or health information is supplemented per veterinary in-clinic-office-hospital analyses, evaluations, administration(s) and treatments:

1) Heart, and/or blood, and/or circulatory and/or cardiovascular, e.g., Medina Spirit's death-processes and/or systems;
2) Pulmonary—and/or breathing, and/or lungs, and/or respiration, e.g., coughing-contagion-processes and/or systems;
3) Temperature—skin-fur-hair, and/or organs, and/or body-core-processes and/or systems;
4) Temperature—environmental, and/or surrounding, e.g., in automobile, stable, back yard, etc.—impacting healthy-unhealthy-life-threatening bodily processes and/or systems, sourced from animals and/or sourced from prediction-reporting environmental-weather-news institutions-sources, communicated-re-communicated-noticed to ownerships-designates-veterinarians;
5) Organs—e.g., digestive, and/or kidneys, and/or liver, etc.—processes and/or systems;
6) Reproduction—male, and/or female, and/or pregnancy-processes and/or systems;
7) Implants, painless per veterinary-anesthesia, and/or ingested and/or inserted devices-monitors-sensors-sources (DMSS) of animals' bodily processes and/or systems; "sources" as used herein, may include animal-health-safety-life-threatening conditions, e.g. animal-body sepsis-sensed, to remote-from-animal health-safety-life-threatening tornados-forecast, per animal-GPS location, designates zip-code, county, state, regional-other locations.
8) Skeletal—blood-cell production, bone analyses, and/or joints, and/or tendons, etc.—Musculature—bone attachments, tendons, e.g., racing-polo horses-processes and/or systems;
9) Brain—spine, and/or nerves-processes and/or systems;
10) Eye—vision, e.g., eye-worm-parasites, etc.—processes and/or systems.

In an embodiment of the invention, the animal health and safety system includes a halter/harness/hackamore/bridle (hereinafter "HHHB") of the invention which can provide sensing and monitoring of the vital life processes and signs of the animal, e.g., such as equines, upon which the halter is placed.

In another embodiment of the invention, vital life processes and signs can be monitored, especially skin temperature of the animal, internal temperature of the animal, pulmonary—breathing/respiration (e.g., coughing), cardiovascular—heartbeat and blood and sweat analysis, etc., and these vital life processes and signs can be archived and communicated to and from a location remote from the animal itself, such as to a veterinarian, research institution, owner(s) records, trainer or other designated custodian of the animal and/or smart computer(s)/communicating device(s) often employing platform(s) and programs(s).

This monitoring/sensing of the animal vital life signs and processes permits system self-correction: Human created systems can self-correct . . . for instance, the kidney-to-heart-ailment® veterinarian's kidney-ailment-diagnosis . . . to the correct heart-ailment assessment, per DMS-system-data-read . . . the purpose of the system being to correct/confirm veterinary readings of DMS-data per maintaining-sustaining animal health.

Other embodiments of the invention may take the form of:

An animal health and safety system comprising: a registry for animal owners and their animal(s); a database where identification of individual living animals is stored; at least one body covering selected from the group consisting of a halter, a hackamore, a bridal and a harness for placement into contact with an individual living animal; the body covering comprising at least one device to obtain data directly from the living animal; at least one communication device to transmit the obtained data to a location remote from the animal where the data is analyzed or archived; a computer communicating with each of the registry, the database, and the archive to assemble information on the individual, identifiable animal; the computer being reprogrammable/repurposed by one member selected from the group consisting of an human, artificial intelligence (AI), and combinations thereof; or A reprogrammable/repurposed system for manipulating data obtained directly from a living, individually identified animal; the system comprising: a computer; a database; an archive; sources of data taken directly from the living, individually identified animal; sources of data taken from other than from the living, individually identified animal; smart communication units selected from smart devices in the group consisting of smart phones, smart wearables, laptops, tablets, and other smart devices; a communication network operably connected to each of the sources of data taken directly from the living, individual animal and to sources of data taken from other than from the living, individual animal, to the computer, to the database, and to the archive; the communications network further operably connected the smart communications units; the computer being operated by artificial intelligence (AI) to reprogram/repurpose the system to manipulate the data; or A method for reprogramming/repurposing an animal health and safety system containing an initial human diagnosis of a disease in a living, identifiable animal, the method comprising: registering a living, identifiable animal in a database; obtaining data in the form of life-sustaining and life-threatening information directly from the living, identifiable animal; communicating the data to a location remote from the animal; archiving the data; utilizing a computer operated with the aid of artificial intelligence (AI) to search the database, and the archived data and reprograming/repurposing the animal health and safety system to identify a disease other than the initial human diagnosis of disease; or A Bonded Registry system comprising: a database of registered owners and their registered animals; at least one animal borne fitment selected from the group consisting of a harness, a halter, a hackamore, a bridle, a trapping and a tack; the at least one animal borne fitment comprising a device/monitor/sensor/source configured to read/sense/obtain at least one condition specific to the registered animal's vital life processes/signs; an archive containing information at least two forms of identification of the registered animal from the group consisting of image of the animal, video of the animal, retina scan of the animal, DNA of the animal and genetic information of the animal; the archive further comprising real-time communicated veterinarian health history including both text and images; the Bonded Registry system further comprising a bond, posted by the owner(s)/officer(s)/manager(s)/operator(s) of the Bonded Registry system, to guarantee financial payment of at least one of the items selected from the group consisting of recovery, custody, care, transport, remuneration and reunion undertakings, lifetime animal care and endowment therefor.

In still further embodiments of the invention, Healthy Life Sustaining and/or Unhealthy or Life-Threatening conditions for animals would be monitored, communicated, recorded and/or otherwise acted upon immediately by human intervention and/or automatic treatment. Among such embodiments are:

1. Atmospheric-Environmental Monitorings and Alerts—electrical storms-lightning; hurricanes; tornadoes; pesticides; hail; dust storms (asphyxiation); wild fires (smoke, burns); flooding (drowning); industrial fire pollution, e.g. chemical-refinery fires-emergencies; shelter-in-place urgencies-emergencies; extreme atmospheric-environmental heat and other conditions generally, as monitored-sensed by in-animal-body, on-body, about-body, ambient-to-animal-body devices, and-or provided-reported by media-news-weather reporting-prediction sources, all communications by all means to implicated-recorded animal ownerships-designates-veterinarians by the Animal Safety System.
2. Temperature Monitorings and Alerts—normal temperature; skin temperature; body temperature; stable or other animal housing temperature; ambient-atmospheric temperature; situational temperature, e.g., in automobile temperature;
3. Respiration-Pulmonary Monitorings and Alerts—normal respiration rate; elevated respiration rate; irregular respiration rate; reduced respiration rate; coughing, disease(s)-infection(s) symptoms; respiration difficulties generally;
4. Heart-Cardiovascular Monitorings and Alerts—normal heart rate; elevated heart rate; irregular heart rate; reduced heart rate; animal cardiology.
5. Optionally—painlessly-via-veterinarian-administered anesthesia animal implant(s) device(s)-monitors-sensors-sources (DMSS) may be provided for bio-chem-other-monitorings/sensings, communicated-read from all sources by all devices, communicated via low-power-signal to a halter-harness-hackamore-bridle borne signal-booster-device(s), and/or communicated directly, and/or to on-animal-medallions, and/or to smart computers-records-devices-platforms-programs, personal-smart-communicating-devices-wearables, other designates-entities, remote from the animal, per Animal Safety System authorization(s).

In a still further embodiment of the invention, the animal safety system, including an equine safety halter/hackamore/bridle or canine/feline harness, can provide information concerning the environment external of the animal, such as stable or paddock temperature, in-automobile temperature(s), humidity, air quality conditions, including particulates such as dust, air-borne-pesticide, smoke, smog, pollen and other animal health and safety impacting conditions.

In an even still further embodiment of the invention, the sensing/monitoring of the animal's vital life processes and signs, the archived and communicated information, and optionally, external ambient conditions vitally impacting the animal, can be combined into determining whether the environment is unsafe for the animal, of use for establishing, maintaining or modifying an exercise regimen, determining periods of inactivity, and be used to plan/alter/reformulate the caloric feed intake of the animal, as well as monitor, analyze and communicate vital aspects of animal comfort, health and well-being, sourced from communicating devices, monitors sensors and records.

In even further embodiments of the invention, the equine safety halter/hackamore/bridle can be fitted with an animal locator, such as a global positioning ("GPS") sensor, to identify the location of the animal, including the animal's location within and without zones of safety, zones of danger, or zones outside of predetermined locations, and additionally can therefore be used to locate and recover, a disoriented, missing, or stolen animal. While we generally speak herein of global positioning systems ("GPS") to identify the location of the animal, we are not limiting the scope of this disclosure to only such a system, as it is possible to use other systems to locate an animal. This may be required as an alternative, especially if the current GPS system is compromised or otherwise unavailable. Other animal locating systems can be employed together with GPS, or as an alternative thereto. For example, other technologies, such as triangulation from cell towers; or other systems to locate the animal can be employed, including any improvements to existing GPS. Hereinafter, animal location systems are generically referred to herein as "GPS and/or other technologies"; and applies generally to techniques employed by the Equine Health and Safety System and Method.

In still further embodiments of the invention, "medallion(s)" can be affixed to, or incorporated into, the safety halter/harness/hackamore/bridle. This medallion can carry simple indicia, such as a telephone number, a bar code, or smart phone/device readable QR code or other code-technology. Thus, simple indicia may provide the reader of such indicia, and/or place the reader directly into contact with, the veterinarian or the owner(s) records, stable or designated care-custody-custodian authorizing entity(s) trainer(s), etc. Further, the medallion may be connected to smart send-and/or-receive communications devices, which when activated by a simple gesture [e.g., pressing a button, and/or tapping a smart-device screen, and/or typing instructions into a smart-communicating-device, or other indicia and/or procedures, etc., connects to an authorizing entity, and/or a veterinarian, owner, designated animal-emergency care-custody-custodian(s), etc.]. Alternatively, the medallion(s) can contain an upgradeable memory, and/or communications links via which numerous types of authorizations, data, and information can be included, and communicated, including specific identity information of the animal, (such as retina/eye, DNA/genetic identity/information, including breeding and genetic information and/or other forms/devices of identification) and images of the animal(s)/ownership(s) designate(s), plus care, custody, transport and remuneration authorization information for a lost/missing animal if/when found and in-system-recorded authorized ownerships-designates animal(s) urgency-emergencies, and similar health, safety and persons/professional/licensed-care/location/recovery/remuneration authorization(s), and information. Furthermore, the medallion can be used as a device for control(s), such as visual video-images, or a light or series of lights on the halter, preferably light emitting diodes, that can function as visible forward facing and/or overhead and/or on halter/harness/hackamore/bridle illuminating lights, such that the animal can be located by search from the ground or air (e.g., by aircraft, drones, etc.); and/or for path/road illumination, safety and warning lights; or controlling of flashing and warning lights when dusk falls, and/or may emit auditory sounds, such as beeping and/or GPS signaling, and/or other voice or other messages/images, when the animal is surrounded by brush, or otherwise not visible, to assist in locating/recovering an animal, visible or obscured, or in comforting, reassuring and/or calming the distressed animal. The medallion can facilitate communication(s), and also act in conjunction with the GPS and/or other technologies to illuminate the harness lights whenever the animal strays from its GPS designated "safe location(s)," and function as a communication link via the halter-medallion per smart devices to the animals designated care-recovery-authorizing-custodian(s) for out-of-safe-zones-disoriented and/or missing animals; smart communicating devices may also activate lights and/or messages and/or locations to aid in animal location and/or recovery. Miniaturization allows for halters/hackamores/bridles to carry two-plus smart-communications nexus-medallions (as illustrated at 10 in FIG. 1 B and FIG. 6).

In still further embodiments, the safety halter/harness/hackamore/bridle may generate and transmit an alarm and/or smart communicating device message(s) whenever the lead rope is disconnected from the halter/hackamore/bridle, such as when the animal is tethered by the lead rope to a fixed location and unauthorized disconnection of the lead rope from the halter/harness/hackamore/bridle occurs . . . thieves beware. As an option in such an embodiment, upon disconnection of the lead rope, the GPS located in the halter/harness/hackamore/bridle, initiates, and continues obtaining location positions, and in conjunction with the communicating device, apprises the owner, veterinarian, or other designated entity, in real time, the location of the animal.

GPS and-or other location technologies, can/may be combined with any and all of the capabilities and services presented in this disclosure, either in-animal-body, borne by animal, remote from animal, and/or combinations thereof, and/or archived, communicated, logged, tracked, otherwise deployed/proffered, per FIG. 1A through FIG. 9.

The animal health and safety system, including equines, safety halter/harness/hackamore/bridle as well as the canine/feline harness of the invention is provided with varied in-animal, on-animal, and ambient-about-animal-body including communicating devices, monitors and-or sensors to determine one or more of the foregoing conditions of the animal's vital life processes, signs and health-and-safety-impacting ambient conditions; sensors to determine the environmental conditions external to the animal, including GPS location, illuminating and safety lights, audible sounds, including smart telephonic two-way communications; and such sensors may further interact with implants or ingested/inserted device(s)/monitor(s)/sensor(s)/source(s) within the body of the animal, such as implants or ingested or inserted devices/monitors/sensors/sources being placed with the aid of a painless veterinarian-assisted anesthesia and/or other professional(s), to supplement the vital life processes and signs which can be determined by the sensors external to the animal body located on the body and/or the Animal Safety halter/hackamore/bridle for ungulates or canine/feline harness all for the lifetime comfort, health, life and well-being of the animal. Via programs and/or platforms, animal health and safety information optionally may be integrated, analyzed, diagnosed to optimize animal comfort and health, and address/treat/isolate/cull infectious disease transmission to other animals and-or humans, e.g., equine Chronic Wasting Disease ("CWD"); use of the safety halter/hackamore/bridle system provides an infectious disease agricultural, veterinary, and public health asset and resource.

An Humane Note: Painless-per-veterinary administration of anesthesia, . . . and only for the health, safety and well-being of equines, canines and feline animals, e.g. life-extending=life-saving companion-animal kidney-functions bio-chem monitoring; implants per veterinary-anesthesia are solely used to further the health, safety and over-all well-being, plus life-extension=life-saving of the animal, as monitoring bio-chem processes and/or the results of pharma-administrations, and/or per other vital health processes, signs and symptoms, saves animals' lives, as well as prolonging that life and the animals' continued general well-being, e.g. had Medina Spirit benefitted from cardiac-cardiograph plus general comprehensive health monitoring, per implant and/or other devices/processes, (via the health, safety and well-being protocols set forth in this disclosure), he likely would not have suddenly died on the Santa Anita Race Track, during a light work-out. Rather, his heart condition would have been diagnosed, monitored and/or treated, and Medina Spirit's very life and general well-being sustained, as an at-stud "daddy" siring a robust line of nobly pampered thoroughbred foals.

The disclosed embodiments further include methods of conducting the Health and Safety Monitoring(s), as summarized above, and as further disclosed in the preferred embodiments below, for optionally monitoring, sensing, analyzing, in situ, and or transmitting to a location remote from the animal for logging, analysis, diagnosing, administration(s), treatment(s)/procedure(s), archiving, research; notifying owner(s), steward(s), veterinarian(s) and or other designate(s) in real-time, including urgent and emergency noticing, environmental/ambient conditions, locating and recovering/care/custody of missing/disoriented animals, as well as other embodiments as disclosed herein, per the Animal Safety System authorizing entity-entities.

Via programs and/or platforms, animal health and safety information optionally may be integrated, analyzed and diagnosed to optimize animal comfort and health, and address/treat/isolate/cull infectious disease transmissions to other animals and/or humans, e.g., equine Chronic Wasting Disease (CWD) and Mad Cow Disease (BSE) in cattle; the safety hackamore/halter/bridle is an infectious disease, agricultural, veterinary and public health asset and resource.

The health and safety of valued animals: Arabian, breeding, polo and racing equines, may be valuable investments, while companion animals, canines and felines, emotionally valuable, often lifetime love-bonded to their stewards, also known as "Pet-Parents." Equines, and companion animals, are also valued as lifetime-love-and enjoyment-bonded companions, often as "Furry Family Members." Thus, we find canines, equines and felines highly valued health and safety needs are simultaneously highly valued financially and/or per-enjoyment love-bonds e.g., the enjoyed, loved, and financially valuable polo-steed.

Per common, shared value and value extension then, the previously summarized disclosures as to serving the health and safety needs of equines via safety halters/harnesses/hackamores/bridles also fully applies likewise to serving companion animals health and safety capabilities and functions via harnesses . . . resulting in the capabilities and functions of safety halters/harnesses/hackamores/bridles summarized and discussed per the disclosure drawings, also fully inclusive of companion animal harness capabilities and functions, with harness and halter/hackamore/bridle disclosed capabilities and functions applying equally and fully to halters/harnesses/hackamores/bridles.

Additionally, common, shared function and use further unifies companion animal canines, equines and felines, per halters-harnesses-hackamores-bridles common, shared capabilities, functions and use—for animal guidance-control and safety—whether the bridled horse is on the racetrack, for weekend saddle riding enjoyment, or as haltered post-riding stable lead; walking the harnessed dog in city traffic; or keeping harnessed kitty safely in the car during car-door-opening road-trip gas-stops, equine harnesses being employed for animal guidance-control likewise for centuries—all common, shared functional uses for guidance-control and/or animal safety.

These and other embodiments will be explained in further detail when read in conjunction with the detailed description of the preferred embodiments and the appended drawings.

BRIEF DESCRIPTION OF THE DRAWINGS

(NOTE: In FIGS. 1A, 1B and 1J; bridle 50 in FIG. 1H, hackamore 80, FIG. 1I, and medallion 210 fixedly attached to harness 200, FIG. 1J.)

DETAILED DESCRIPTION OF THE PREFERRED EMBODIMENTS

Figure 1A:
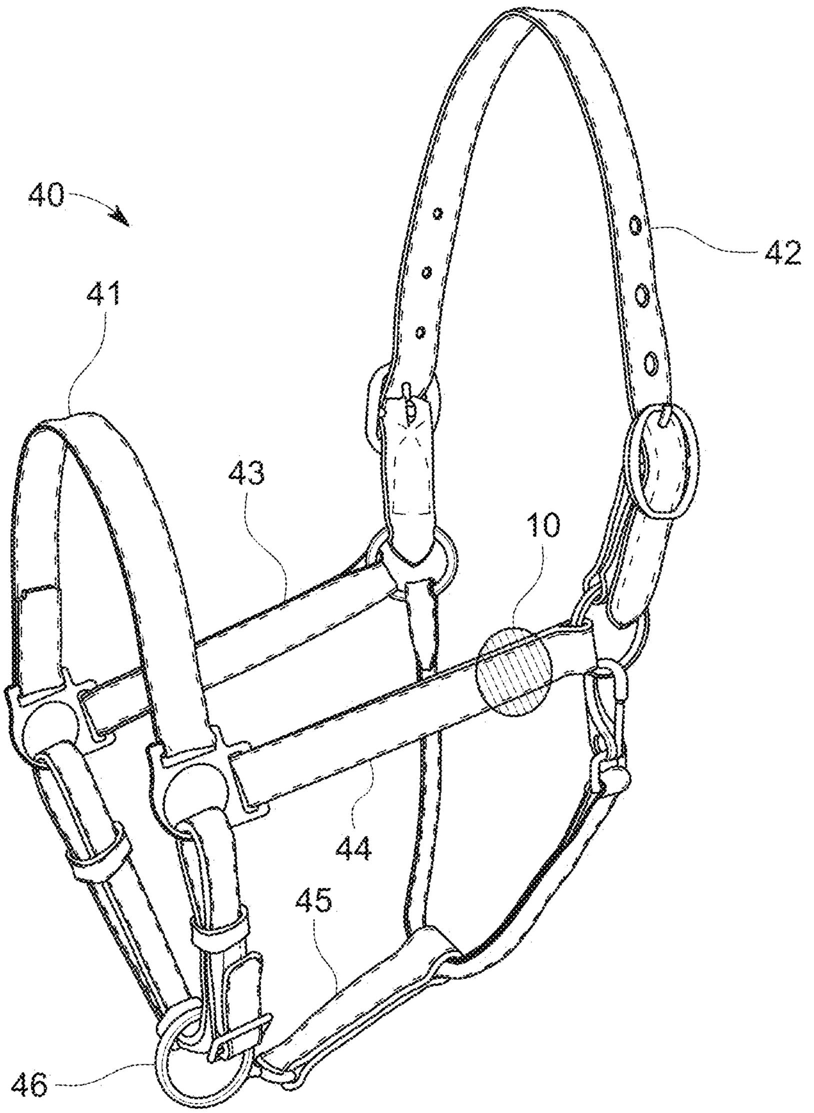
FIG. 1A is a schematic, perspective view of a halter 40 suitable for use as an equine safety halter.

Definitions: As used in this disclosure, the following definitions are provided:

"Communication(s)" Definition . . . generally, per this disclosure, the term "communication" and/or "signal" and/or "transmission" also includes . . . signal transmissions, boosted (signal-range-strength-increased) and/or non-boosted signal(s), and/or combinations thereof . . . also includes to-from-capabilities . . . including all means of communications/signals/transmissions inclusively for FIG. 1A through FIG. 9 capabilities/functions/services.

Definition—"The 99 Item Questionnaire" . . . is not limited to "99" items, can/may be more or less. Examples of questionnaire topics (e.g. not limiting) include . . . personal interests—adventures, expertise, hobbies, skills, preferences, . . . orientations—attitudes, beliefs, political, social, favorites, preferences . . . travels—places, time frames, years, experiences, suggestions, recommendations, value of currencies used, expensive/inexpensive, accommodations used, recommendations, transportation to & from & during visit, enjoyed experiences, adventures, would like to visit ______? . . . experience/work and leisure—occupation(s), time-frames, retired, favorite job, best job done, leisure time activities, sports, favorite activities, would-like-to-try ______? . . . I am most proud of ______? . . . companion animals-canine-equine-feline—favorite-companion-animal-activities? socialize-with-other-companion-animal-owners? describe-animal-size-breed, loves-to ______? . . . animal health issues . . . personal health issues . . . up-coming-medical-issues . . . what-do-you-like-most ______? . . . like least ______? . . . "what makes me happy is ______?" . . . general commentary ______, and similar questions.

Definitions: "Nextdoor"=neighborhood social media prevalent in California, USA.

Definitions: "pet-to-vet" is any type of veterinarian rewarded system for reimbursing costs/expenses incurred in caring/housing/treating lost/missing animals, once found.

Definitions: "DMSS" . . . D=Device(s) . . . M=Monitor(s) . . . S=Sensor(s) . . . S=Sources; DMS=raw granular data from DMS . . . Sources=data-driven information=e.g. NOAA Hurricane forecast, Commercial Weather forecasting animal-life-impacting unhealthful hot weather; generally, per this disclosure, DMSS may also include healthful and unhealthful data-information from other sources.

Definitions: Data=raw-granular to be system-discerned-read; Information=e.g. from Sources=raw data that has been formed into understandable information=NOAA forecasts, Commercial weather forecasts, etc. DMS-S . . . DMS provides raw data, to be system read into discernable-understandable "Information"=Source(s) . . . thus D M S S . . . .

Definition: "Halters, hackamores, harnesses, and bridles", ("HHHB") are configured and used together; equine bridles, and equine bridle-and-harness-configurations, share key characteristics, therewith disclosing a single inclusive device group by shared animal control, comfort, and safety application, function, purpose and use; FIGS. 1A, 1B, 1C, 1D, 1E, 1F, 1G, 1H, 1I and 1J.

Definition: "Harness" uses are also common to, and shared by, equines and canines/felines; as previously disclosed, sled dogs beneficially employ a horse harness, that also distributes pull-weight about the dogs' chest and shoulders, whereas dog-collar-only-usage would restrict sled-dog breathing. A sole dog collar use about an animal's neck generally risks choking and restricts healthy breathing, more so for robust animals, with possible trachea crushing damage; trachea crushing is contrary to this Non-Provisional's Health & Safety Mission. Thus, canine harnesses generally, feline harnesses too, provide "horse harness" health and safety advantages also for dogs and cats.

Figure 6:
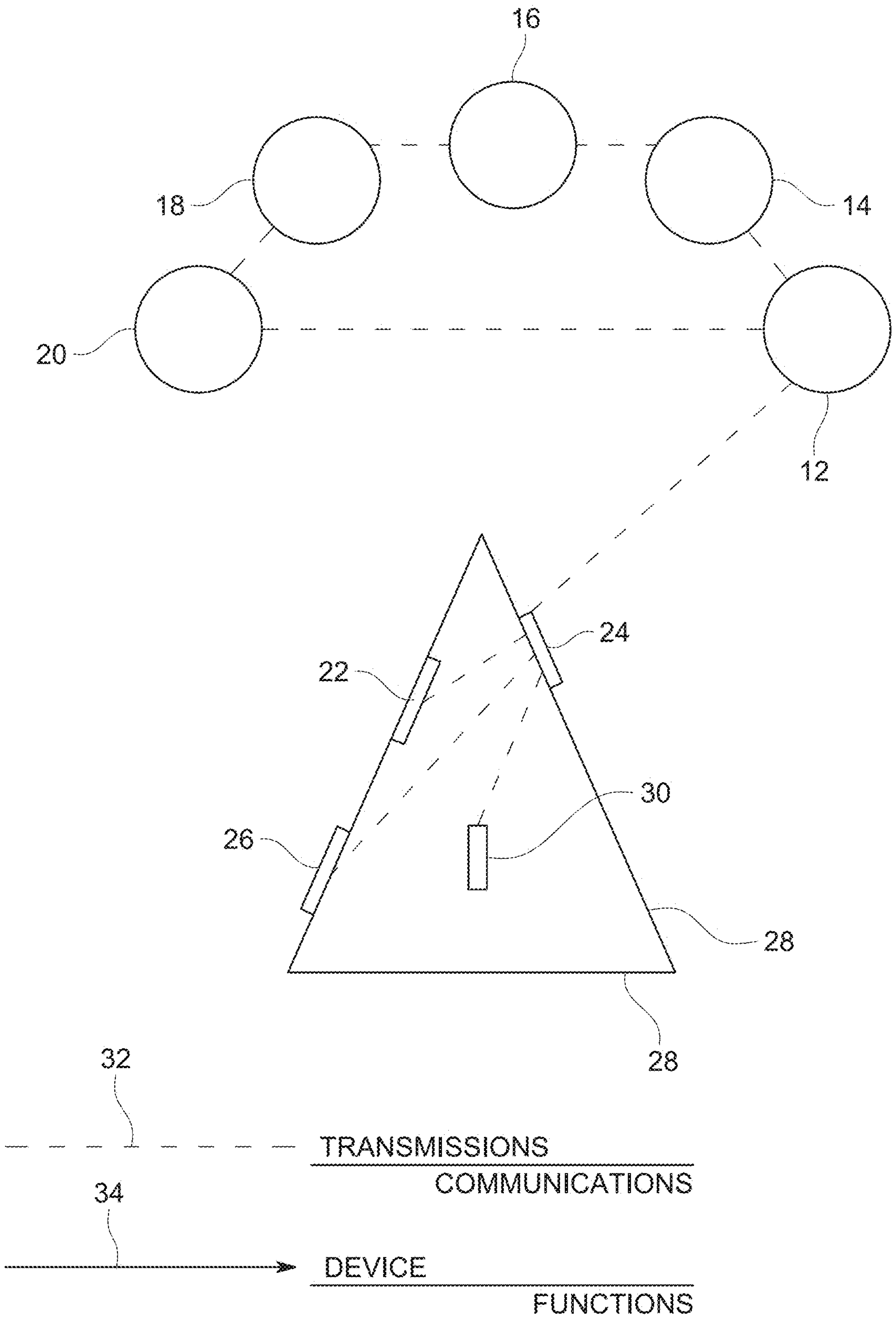
FIG. 6 is a perspective view of a series of devices/monitors/sensors/sources on the safety halter/harness/hackamore/bridle strap of FIG. 2 in combination with a communication system, with the triangle, 28, in FIG. 6-28, functioning as a schematic representation of the halter 40,—FIG. 1A and FIG. 1B; bridle 50, FIG. 1H and hackamore 80, FIG. 1I.

Additionally, within this single inclusive halter/harness/hackamore/bridle harness device group—by shared animal control application, function, lifetime health & safety purposes, and use—shared devices include: FIG. 1C, 1D, 1E, 1F, 1G, 1J—harness; FIG. 2, 3, 4—halter/harness/hackamore/bridle; FIG. 6—halter/harness/hackamore/bridle.

BENEFITS OF THE PRESENT DISCLOSURES

Public Health Benefits—by broadly employing modern monitoring, measuring, assessment, communications and transmissions devices for the Health, Safety and Well-Being of canines/felines, equines and other animals—early potential professional awareness of animal-to-human zoonotic disease transmissions is enhanced, e.g., monkeypox, mink-Covid transmissions. Personal Benefits—canines-felines, equines too, become lifetime-love-bonded furry family members, and their well-being sources enjoyment, family fun and long-term companionship. Economic Benefits—Kentucky Derby-winner Medina Spirit (later disqualified) died suddenly during a light Santa Anita workout; with modern monitoring and assessment means, Medina's health condition would have been known & treated, and the equine asset put out to stud. Sadly, for his death, and sadly for Medina Spirit, his owners/stewards, the horse was lost.

Also, mink Covid-to-human(s) transmissions, and Mad Cow Disease, are two examples of the important, and economically plus socially costly intersection of animal-human diseases—both to human health and society, and to the agricultural and general economy.

Wide use of modern Health, Safety and Well-Being monitoring and assessment means, for canines, equines and/or felines, carries enjoyment, family fun and companionship benefits . . . while providing yet another animal-human zoonotic public health resource . . . with favorable personal, family, public health, social and economic benefits.

Figure 1B:
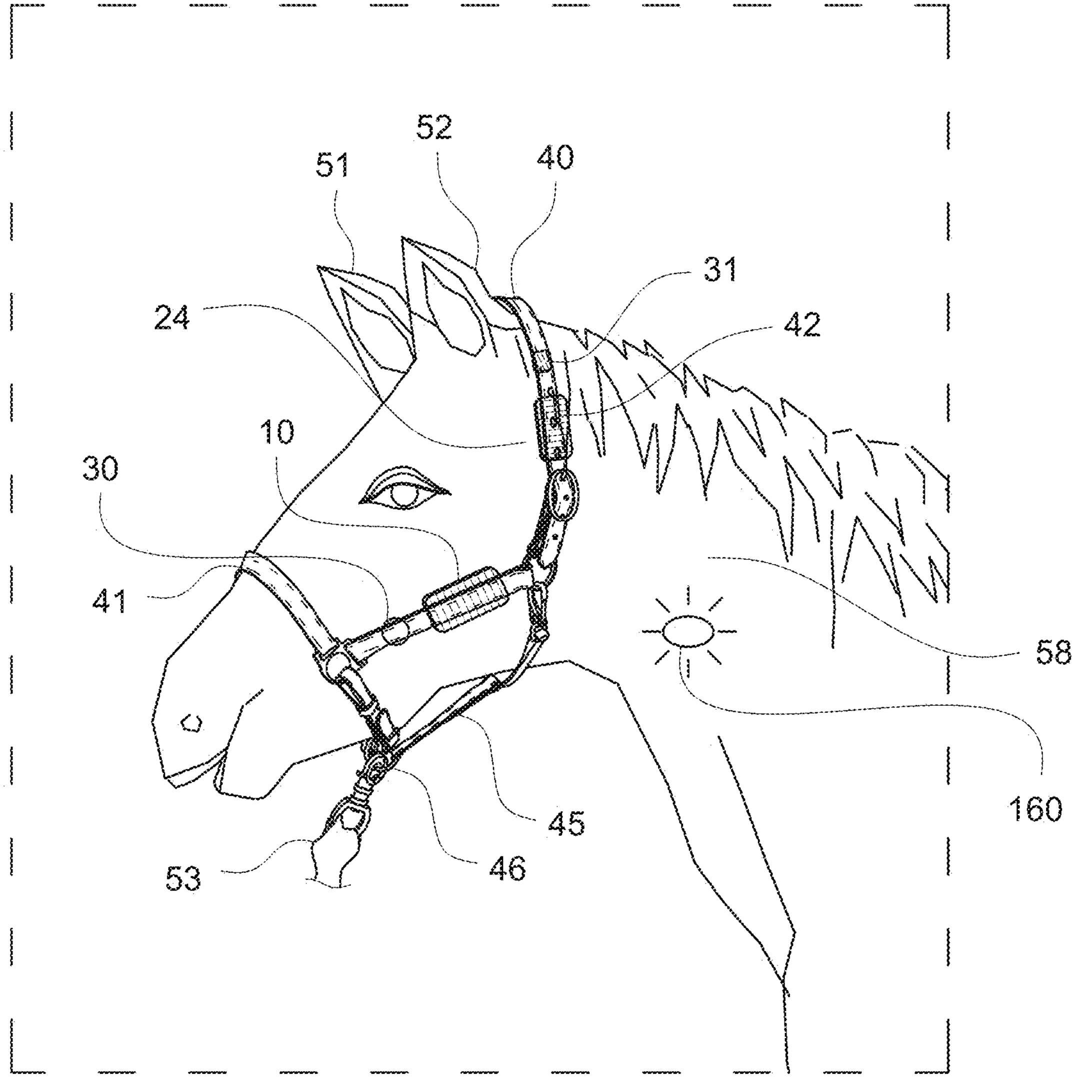
FIG. 1B is an image of an equine wearing one of various typical halter designs.
Figure 1C:
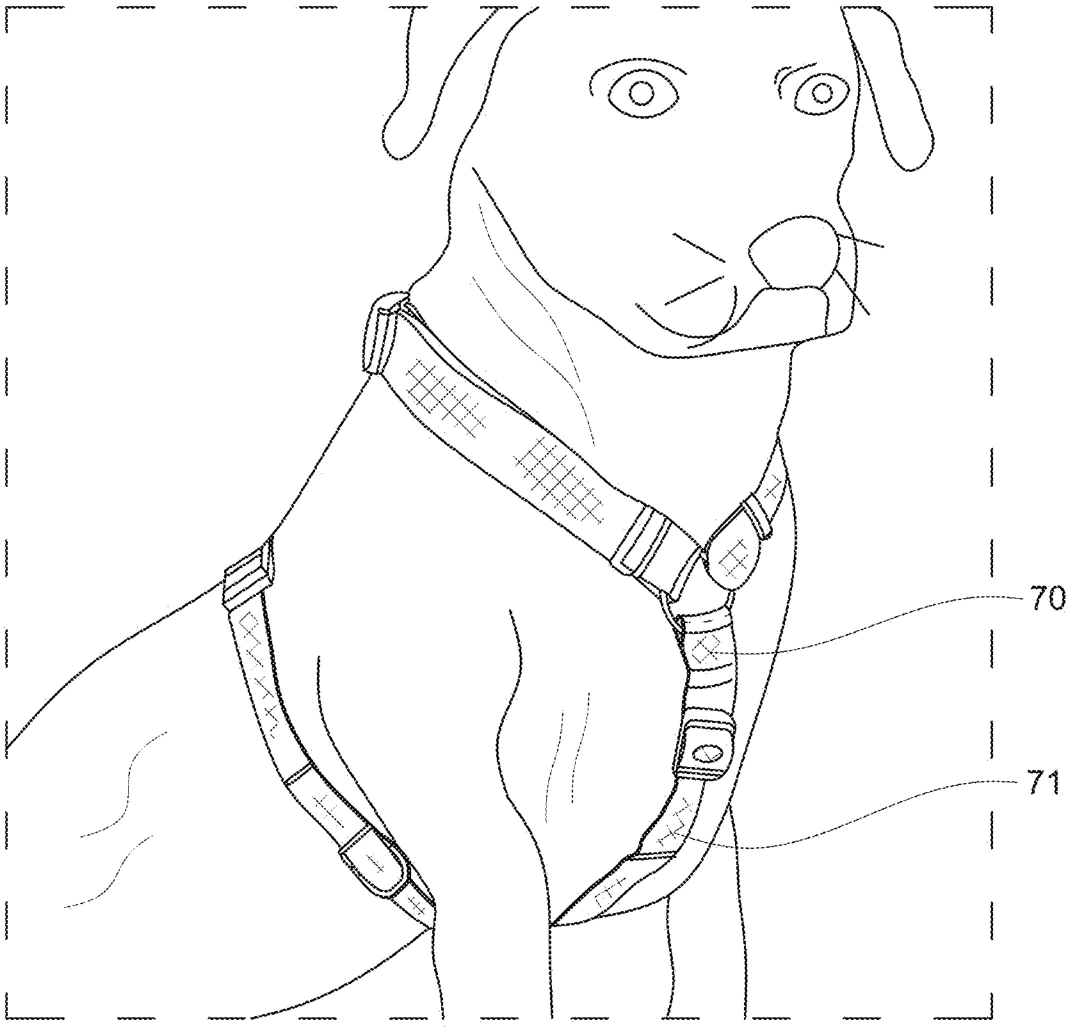
FIG. 1C is a front-image of a first canine 71 wearing a typical harness design showing strap configurations.
Figure 1D:
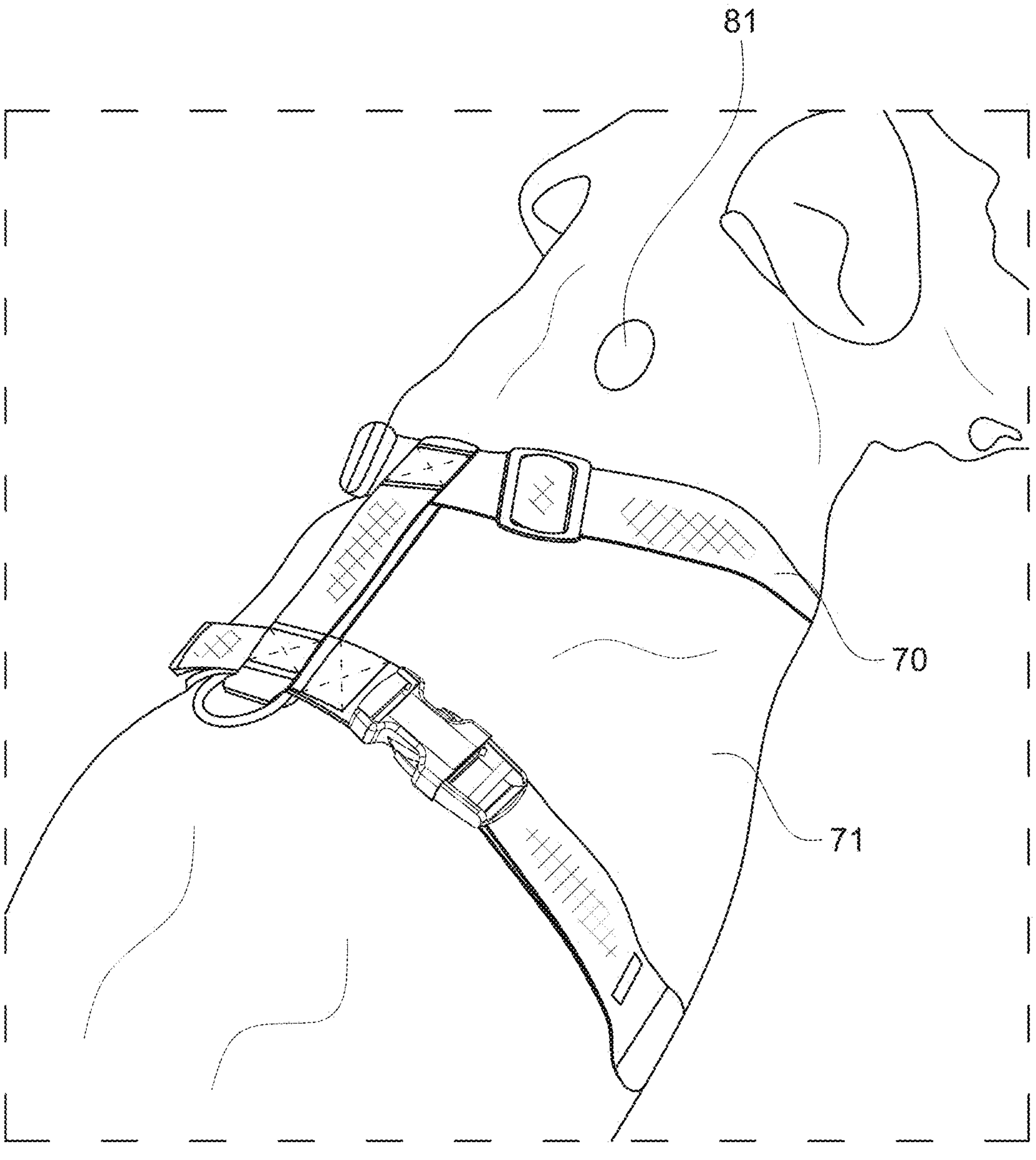
FIG. 1D is a side-back image of FIG. 1C, showing the canine 71 wearing a typical harness-strap-design.
Figure 1E:
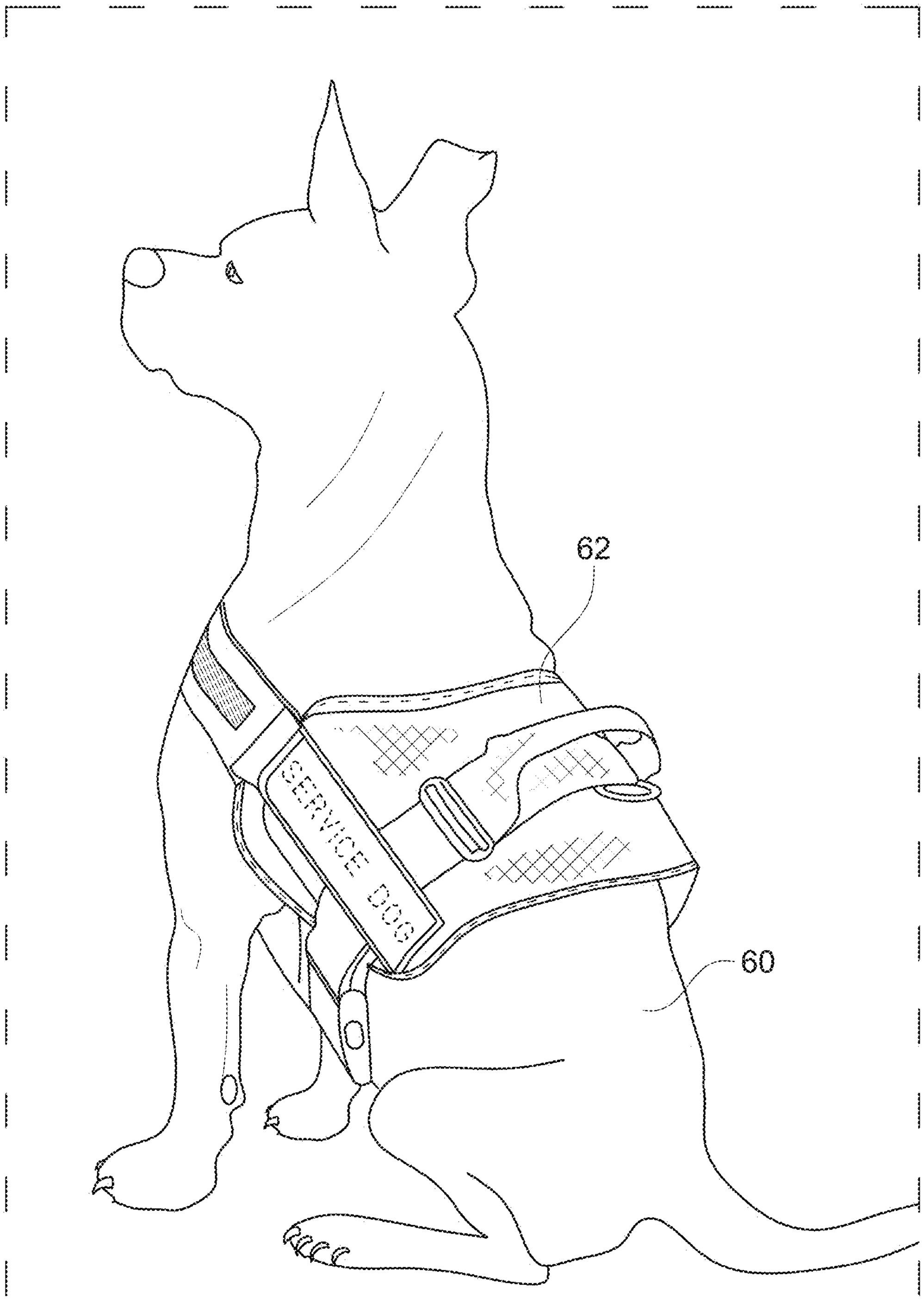
FIG. 1E is a service dog vest harness 62 image on a second canine 60.
Figure 1F:
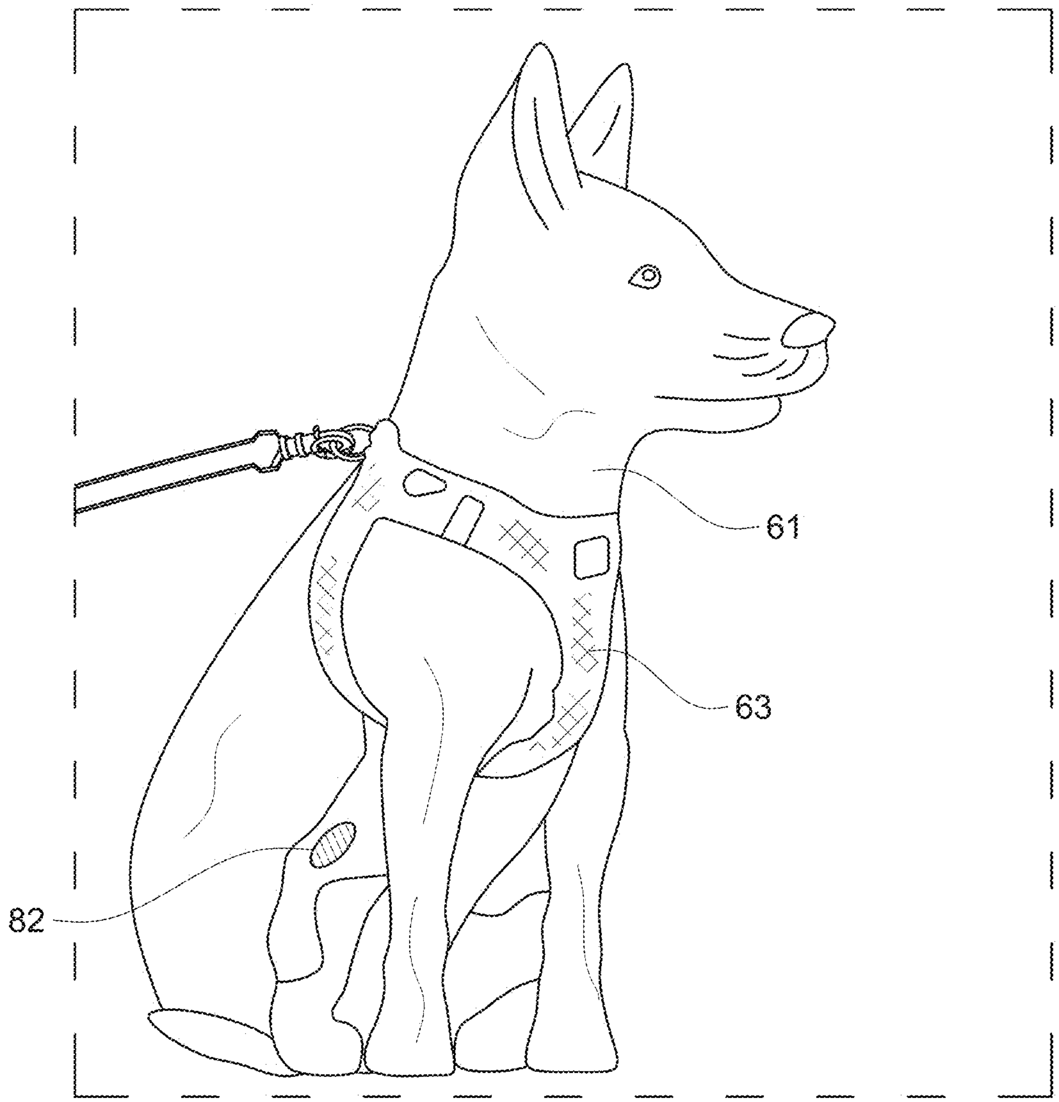
FIG. 1F is a one-piece vest harness 63 image on a third canine 61.
Figure 1G:
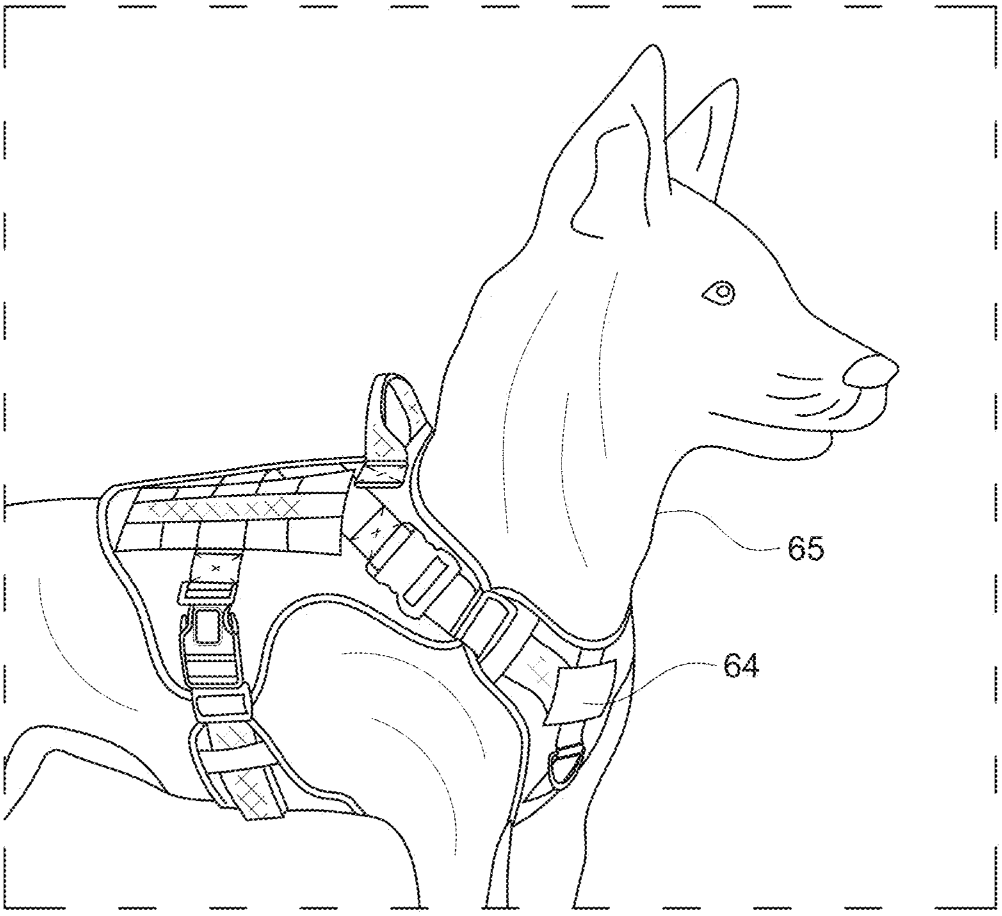
FIG. 1G is a military/tactical harness 64 image on a fourth canine 65.
Figure 1H:
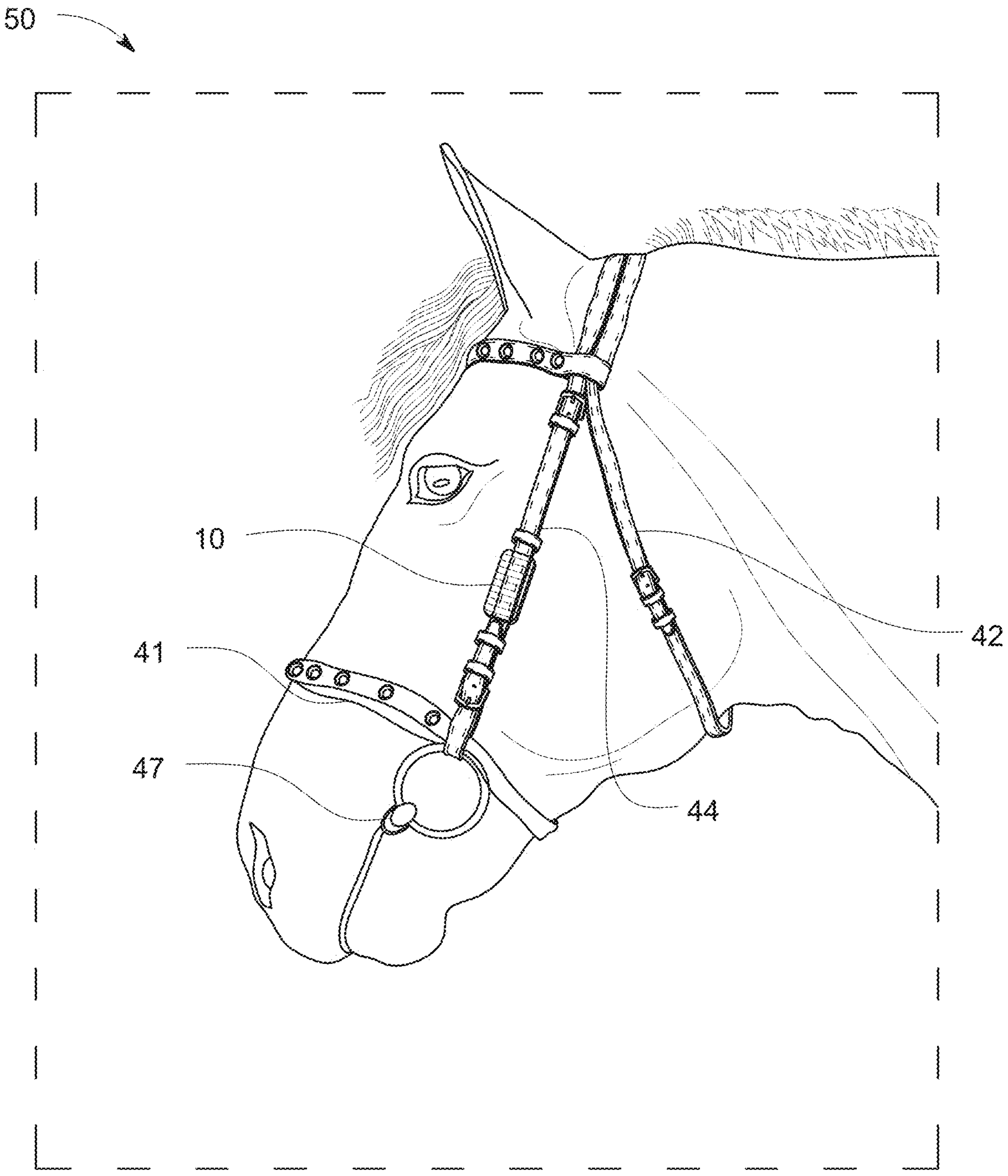
FIG. 1H bridle 50 image illustrating shared components of halter 40 and bridle 50.

Core concepts of the disclosed methods include the communications-transmissions . . . between health, safety, well-being animal monitoring-sensing devices . . . in body, and/or harness/or otherwise borne by, and/or away-remote from the animal(s) . . . such data-information being generally and specifically relevant to canine, equine, feline animal's lifetime health, safety and well-being . . . and to these animals ownership(s)-professional(s)-designate(s) . . . via smart-computer communicating-transmitting devices . . . and/or via computers-platforms-programs-archives overseeing-processing-surveying monitored-sensed data-information and communicated-transmissions . . . and optionally noticing-communicating-transmitting overseen data-information advisories-messaging to these registration(s)-defined-described animals, and archive(s) defined-described ownership(s)-steward(s)-professional(s)-designate(s) . . . such animals-ownerships-professionals-designates being archive(s)-photo-and-or-video-recorded-identified-defined, per all identification modes and methods, optionally but not limited to retina/eye, DNA/genetic and genetic breeding-lineage information, as well as any animal implanted identification chips, etc. . . . and/or optionally including animal-related-relevant, safety, well-being data-information-records, real-time data-information, including urgent and emergency noticing, and general information . . . optionally monitoring-overseeing-reviewing data-information from-animal-data-information-records . . . and/or optionally messaging-monitoring-noticing animal ownership(s)-professionals-designate(s) about such real-time, and/or animal data-information-records, conditions and situations . . . and optionally noticing-messaging animal(s) ownership(s)-professional(s)-designate(s) about health-safety-well-being related-relevant data-information from-animal-ambient advisories-conditions-information-readings-results, and from government-media-other sources.

Where possible, the same numeral is used to denote the same or similar elements in the multiple appended drawings, (e.g., halter/hackamore and bridle similarities—halter 40, FIG. 1A and elements 10, 41, 42, 44 thereof; bridle 50, FIG. 1H and elements 10, 41, 42, 44 thereof; and hackamore 80, FIG. 1-I, elements 10, 41, 42, 44 thereof). It is also to be understood that the appended drawings are schematic, and are provided as exemplary, but are not limiting, embodiments of applicant's disclosure, and placement of the elements, such as devices/monitors/sensors, Medallions, and other elements on the safety halter/hackamore/harness/bridle, as illustrated in the appended drawings, are exemplary only and not limiting of the disclosure. Moreover, it is to be expressly understood that the illustrations of the placement of devices/monitors/sensors/sources on the halter 40, FIGS. 1A, 1J and bridle 50, FIG. 1H, or hackamore 80, FIG. 1I, are for exemplary embodiments, and the exact position of the devices/monitors/sensors/sources may be varied for maximum animal comfort as determined by a veterinarian, owner, technical-specifications, and/or designated custodian of the animal to avoid sensitive or uncomfortable positions on an individual animal; to provide maximum signals/samples from the comfortable animal; and to accommodate the max-comfortable placement of multiple, diverse devices/monitors/sensors on the halter/hackamore/harness/bridle at the same time. Miniaturization allows one, two, or more medallions/devices/monitors/sensors for halter/hackamore/harness/bridle lifetime health, safety, and animal well-being, capabilities and functions.

Figure 1I:
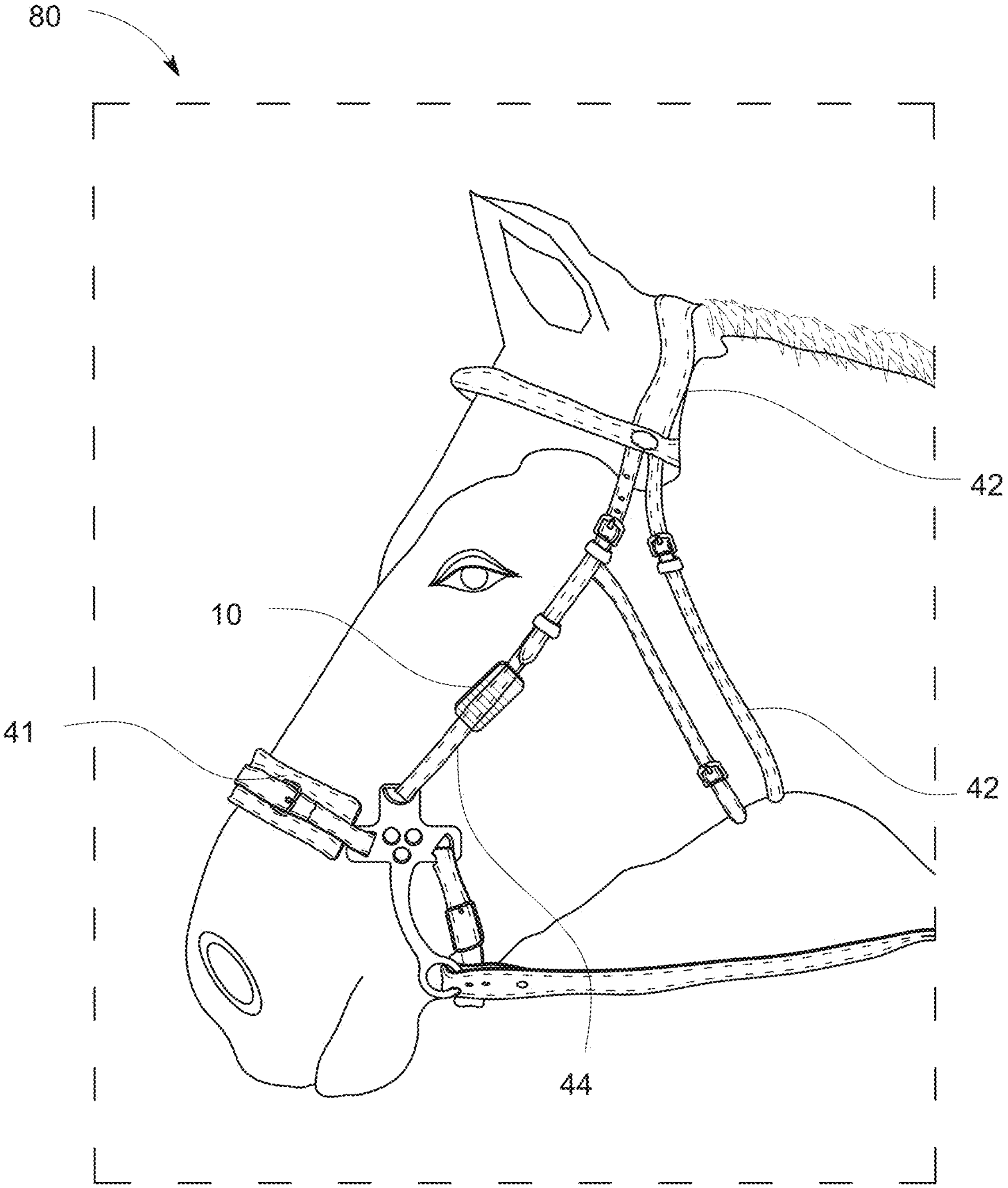
FIG. 1I hackamore 80 image illustrating shared components of halter 40 and bridle 50.

It is also contemplated that as more advanced nano-micro-bio-chem and other devices/monitors/sensors become available for canines, equines and/or felines that they can be readily incorporated into FIG. 1A halter 40-FIG. 1H—bridle 50, FIG. 1C-1D, 70, FIG. 1 E, 62, FIG. 1F 63, FIG. 1G 64, and hackamore 80, FIG. 1I—harnesses of the present disclosure.

Figure 1J:
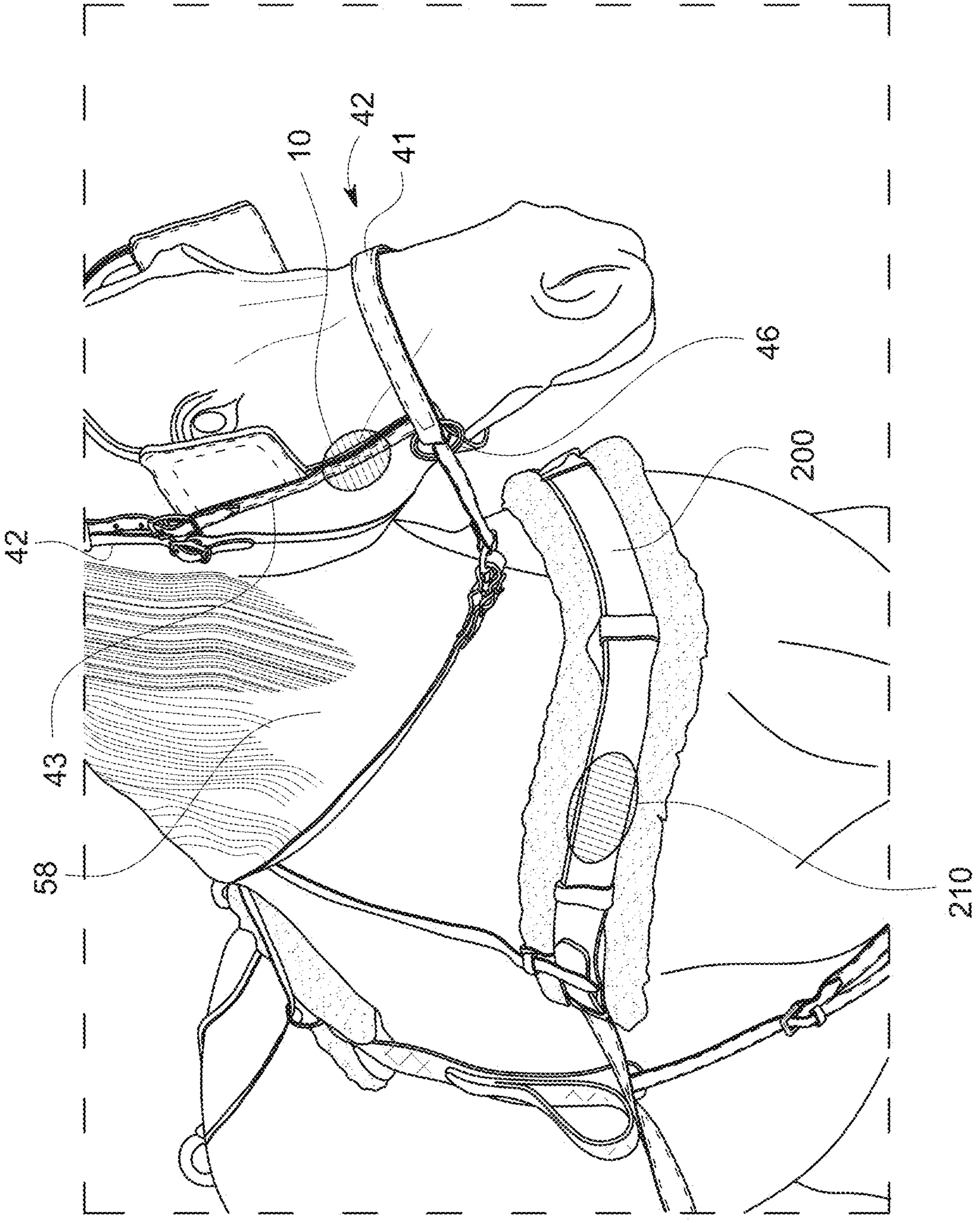
FIG. 1J is an image of an equine harness in combination with the equine wearing one of a typical halter, each fitted out with the devices/monitors/sensors/sources of the present disclosure.
Figure 2:
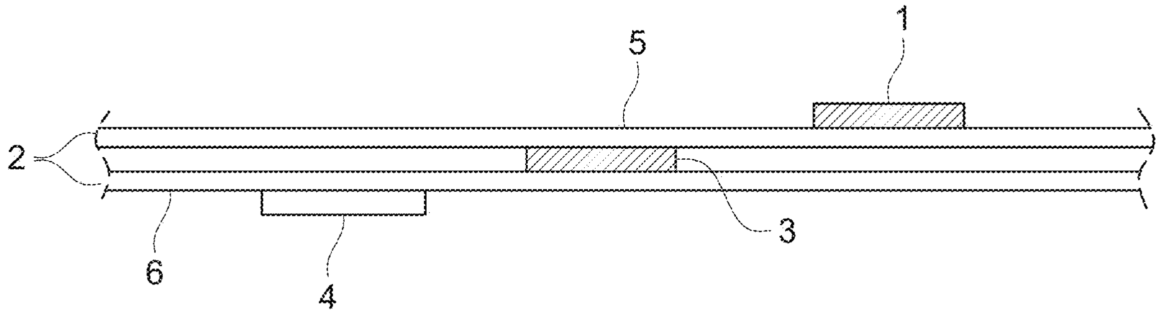
FIG. 2 is a schematic, side, partially cross-sectioned view of the double-straps of health and safety halters/harness/hackamores/bridles for equines, harnesses for canines/felines, showing devices, monitors, sources and/or sensors positioned on halter/harness/hackamore/bridle straps away from the animal, between inner and outer surfaces of the straps, and against the animal.

Further, the present disclosure of the Equine Health and Safety System disclosed herein is not limited to those types of halter, hackamore, harness or bridle as illustrated and described herein, but can be combined with any conventional trappings as known in the art, such as any body-covering (or partial-covering) trapping used, such as the harness illustrated in FIG. 1J, which is a beginner's harness due to its simplicity, but more robust harnesses for draft animals, such as horses, donkeys (including burros), mules, oxen, water buffalo, elephants and other beasts of burden pulling harnesses; and even other "tack" for such animals, such as the body-covering "horse-blanket." It should be expressly understood that the term "body covering" does not require a complete covering of the animal's body, it being sufficient that at least a portion of the animal's body is covered, such as a halter/hackamore/bridle on an equine, canine-feline harnesses too, but also includes a body covering that is supported upon an animal's back, as well as in some embodiments, even covering the animal's extremities.

As can be seen in FIG. 1A, a halter 40 is provided with a noseband 41 for fitting around the muzzle of an equine 58 (a horse as shown FIG. 1B). A headpiece 42, FIG. 1A is connected to the noseband 41, by a righthand strap 43 and a left-hand strap 44 connecting to the noseband; the headstall fits around the poll and behind both ears 51, 52 of the equine 58, as shown in FIGS. 1B and 1J. Lower strap 45, is also connected between the headpiece 42 and noseband 41. A hoop 46 is provided as the noseband 41 for connection of a lead rope 53 (shown in FIG. 1B) to halter 40, FIG. 1A, 1B, for a walking person to safely guide the equine.

Bridle 50 (FIG. 1H), including bit 47 illustrates the similarities between a bridle 50 and halter 40, FIG. 1A; 10, 41, 42 and 44 are alike components of halter 40, FIGS. 1A-1B, and bridle 50, FIG. 1H; equine halter/hackamore and bridle capabilities and functions are disclosed as equally and fully including canine harnesses, as shown, e.g., in 70, FIG. 1 C, -1D, 62, FIG. 1E, 63, FIG. 1F and 64, FIG. 1G; and feline harnesses (not shown). Hackamore 80, FIG. 1I also shares similarities with halter 40, bridle 50, and it should be understood that a structure/function/sensor/probe(s)/medallion(s) described in connection with any one of the halter 40, hackamore 80 and bridle 50 may also be shared among each of halter 40, bridle 50 and hackamore 80, likewise with harness FIGS. 1C, 1D, 1E, 1F, 1G and 1J.

The materials for the headpiece 42 are preferably natural or synthetic leather, or other suitable materials, for the purpose as will be described below. The right-hand strap 43 and the left-hand strap 44 can also be made of natural or synthetic leather, or of natural or synthetic fiber materials.

The noseband 41 and the lower strap 45 can be made of the same or different materials as the right-hand strap 43 and the left-hand strap 44. Halters 40, bridles 50, and hackamores 70 are made of a wide range of any and all materials, harnesses too, from knotted rope, often leather and/or synthetic straps, rolled materials, to finely tooled and expensively decorated leather bridles, hackamores and halters; halters/hackamores and bridles (and harnesses also) may have narrower straps, rolled materials to broad straps and cushioned/padded and/or companion animal body-covering designs, made from a vast array of suitable materials per animal comfort. Halters/hackamores are very comfortable for animals, harnesses also, as they can eat, graze and water freely. As noted, an animal halter that adds a mouth-bit is generally termed a bridle, and is expressly encompassed by the term "halter" in the appended claims. The close similarities shared by bridles-hackamores and halters-harnesses are disclosed per FIGS. 1A-1B and FIGS. 1E-1J.

As shown in the cross-sectional view of FIG. 2, an away-from-body surface 5 of halter 40 shown in FIG. 1A, or harness 200 shown in FIG. 1J, can contain external sensor 1, FIG. 2, which can be used to determine conditions external to the animal, e.g., weather, temperature, noise (e.g., sensing contagious coughing), pollution, pesticides; and can be attached to the exterior surface of halter 40, FIG. 1A, e.g., to the exterior surface of headstall 42. A sensor or other device 3, FIG. 2, can be included between the exterior surface 5 and interior surface 6 of headstall 42, FIG. 1A; finally, a near/against the body sensor 4, FIG. 2 can be included on the interior surface 6 of headstall 42, FIG. 1, or elsewhere, such as the interior surface of harness 200, FIG. 1J, to obtain vital life processes and signs directly from the animal. In FIG. 2, device 3 can be a GPS, or other location sensor, to monitor safe and unsafe areas as well as for general location tracking positioned internally between the exterior surface 5 and interior surface 6 of the halter/hackamore/bridle which prevents tampering with the GPS or other location sensing device, unlike the sensor 4, which should be located in the headpiece 42, FIG. 1A, sensor 1, FIG. 2 can be located on any of the right hand strap 43, FIG. 1A, and left hand strap 44, FIG. 1A, as well as on lower strap 45. Additionally, the halter/hackamore/bridle can comprise an electronic lock to lock the halter/hackamore/bridle upon an equine to prevent removal of the halter/hackamore/bridal from the equine. The electronic lock can be locked and/or unlocked remotely by at least one of a smart communicating device, a communicated code or a message. (FIG. 2 disclosure includes halter(s), hackamore(s), bridle(s) and harness(es) usage). Each of the sensors described herein may also contain a clock. The clock can be used to timestamp the data as collected. Sensors may also be devices and/or monitors in stable and/or ambient or remote. Such vital life processes and signs may include, without limitation, skin temperature, sweat analysis for equines (including without limitation, cell health and organ functions through use of electrolytes/other processes; immune system such as cytokines; drug interactions, such as metabolites; chlorides, lactate, urea, glucose, creatinine, alcohol, pH conditions, protein and hormone levels and presence of heavy metals) blood pressure, blood glucose readings, heart rate, cardiac rhythms/cardiograph/cardiology, breathing rate/monitoring, motion, and other vital life science patterns, processes and signs, health and safety assessed and monitored per platforms and/or programs and/or persons-professionals-entities. Therapies are also affected, such as creating skin sensations, such as vibrations, or electrical or thermal or other effects to rehabilitate and calm the animal (such as during transport, or in a cold environment), as well as the in situ or otherwise administration of drugs (e.g., pain, motion sickness, high blood pressure, diabetes, etc.). It is estimated that some 25 percent of canines are regularly walked in conditions too cold, wet, or otherwise unhealthy for the animal. The animal health and safety disclosure herein, provides for the sensing of various parameters of an animal's skin and/or core temperature, and heating elements can be provided in various types of animal body coverings, the heating elements being manually or remotely actuated in response to the transmission of the animal's skin and/or body temperature, and/or other sources of environmental and other conditions impacting animal health and safety. Thus, monitoring the temperature of the animal, and through the application of therapies, such as heat imparted by thermal effect, would aid the animal(s)' safety and well-being. Currently available bio-chem and micro/nano-technology and micro/nano-electronics, and other current and emerging technologies, combined with legacy veterinary methods, pharmacology, procedures, remedies, technologies and treatments, are dynamically joined and/or integrated to support complex animal health and safety administrations, analytics, diagnostics, functions, platforms, programs and research via the equine safety halter/hackamore/bridle and/or canine/feline companion animal harness, for the maximum enjoyment, comfort and well-being of highly financially valued and/or lifetime-love-bonded companion animals, per the Equine Health and Safety System.

In FIG. 2, device 3 can be a GPS, or other location method and/or sensor to monitor designated safe and unsafe areas as well as for general location tracking positioned internally between the exterior surface 5 and interior surface 6 that protects and prevents tampering with the GPS or other device; unlike the sensor 4, which should be located on the headpiece 42, FIGS. 1A, 1J, sensor 1, FIG. 2 can be located on any of the right hand strap 43, FIG. 1A and left hand strap 44, as well as lower strap 45, or on various portions of harness 200, FIG. 1J. FIG. 2: Single and/or multiple device(s) and/or monitors, and/or sensor(s), are optionally positioned on the halter(s)/hackamore(s)/bridle(s)/harness(es) for optimum humane animal comfort, functioning and performance, per veterinary and technical expertise, to maximize the overall lifetime comfort and well-being of animals, both individually, and as groups, per archived-registered addresses-location-information and/or zip code, county, state or region.

Figure 3:
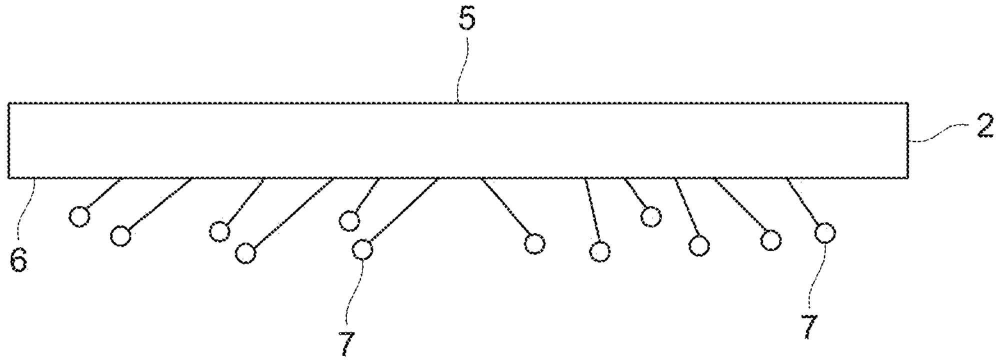
FIG. 3 is a schematic, halter/harness/hackamore/bridle strap, end, cross section view of the FIG. 2 strap, enlarged to show detail of the devices/monitors/sensors/sources (DMSS) of the health and safety halter/harness/hackamore/bridle straps of FIG. 2.

FIG. 3: Illustrates an enlarged view of the plurality of slender, small probes 7 that optionally protrude multi-directionally, via various lengths, constructions, and dimensions, from interior/against-the-animal surface 6 of headstall 42, FIG. 1A, or optionally other comforts-and-functions maximizing location(s), against and comfortably through-to-against skin of the animal's fur/hair, for through the fur/hair multiple contacts with the skin of the animal(s), from which the various device(s)/monitor(s)/sensor(s) vital life processes and signs are obtained, analyzed, communicated, diagnosed, monitored and/or recorded and/or assessed per platforms and/or programs, optionally interfaced and/or interconnected. Although a single probe is operative to obtain a single condition/measure of the animal, e.g., temperature, it is preferred to utilize multiple probes 7, even if the function of each of the probes 7 is to obtain averaged and/or confirming information on the same condition/measure. The disclosures of FIGS. 2-3 are generic to and includes halters/hackamores/bridles/harnesses as shown in FIGS. 1A-1J.

Figure 4:
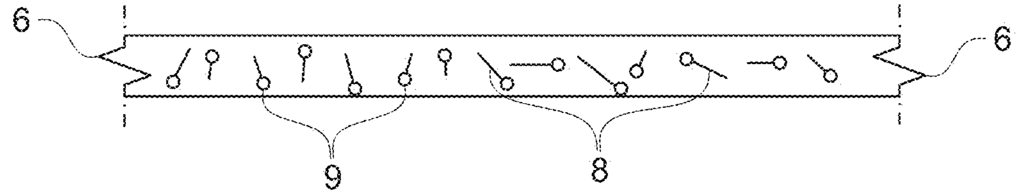
FIG. 4 is a schematic, underside view of the halter/harness/hackamore/bridle strap of FIG. 3, taken from the view with the devices/monitors/sensors/sources of FIG. 3 being against the animal.

FIG. 4: illustrates the flexible multiple probes 8 of different lengths 9, optionally of differing constructions, dimensions, functions and placements for maximum animal comfort and device functioning, directed through the fur/hair of the animal for comfortable, gentle, multiple skin contact(s). Of course, when multiple gentle probes are used, each of the individual probes 7 may be used to obtain different types of information, e.g., one type of probe 7 to obtain sweat samples and another type of probe 7 to detect cardiac rhythms. Additionally, multiple sensors may be used to obtain different types of information, e.g., a separate sensor for heart rhythms and a separate sensor for sweat samples, and/or multiple probe-measurements of the same bio-chem and/or other differing functions and measurements, for measurement confirmation and/or measurement averaging and/or other measurement capabilities and functions. Multiple comfortable probes can also be used for like functions and measurements, as noted hereinabove, for averaging, back-up, and confirmation of measurements/readings. As described hereinabove, the sensor 4, FIG. 2 works directly from the information comfortably obtained from the skin of the animal and/or an analysis of its secretions (e.g. sweat for equines), communicated directly to smart-communicating/transmitting computer devices platforms and/or programs and-or via signal-booster-transmitter 24, FIG. 6 (and/or via 10, FIG. 1A) However, sensor 4, FIG. 2 can also work in conjunction with internal sensors 30, FIG. 6 (per veterinarians, painlessly-per anesthesia surgically implanted and/or ingested and/or inserted, as will be discussed in connection with FIG. 6).

It should be understood that the single and/or multiple device(s) and/or monitors, and/or sensors/sources FIGS. 3-4, and its respective probes 7, 8, 9 can be arranged and modified for multiple uses other than monitoring/sensing. For example, in order to sooth the animal, the probes 7, 8, 9 can be used to impart relaxing electrical and/or therapeutic-mechanical care and comfort for the animal, together with sound inputs from medallions 10, FIG. 1A and 10, 24, FIG. 1B to comfort and calm the animal to preserve its well-being, especially during times of stress, as when the animal is out of its safe-zone, being transported home, etc.

Figure 5A:
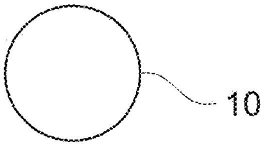
FIG. 5A is a schematic, front view of a medallion(s) 10 to be fixedly attached to the halter 40, in FIG. 5B is a schematic, side view of the medallion(s) 10 of FIG. 5A; medallion(s) are positioned-first per maximum animal comfort, and second-per veterinary assessment, and/or technical requirements.
Figure 5B:
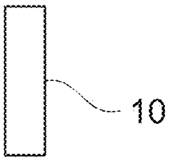

FIG. 5A: illustrates a schematic, front view of a medallion 10, FIG. 5B illustrates the medallion 10 of FIG. 5A in a side view (also 10 in FIGS. 1A and 1B). The medallion 10, FIG. 1A, is preferably permanently mounted on one of the right-hand straps 43, FIG. 1A and/or left-hand straps 44, FIG. 1A by permanent fasteners, such as rivets (not shown) in order to prevent removal thereof from the halter 40. Although we have illustrated the medallion 10 as a single device, with multiple functions, it is also within the scope of this disclosure to use two, or more than two, devices to perform the functions attributed to medallion(s) 10, 24, 210 and multiple other nexus functions. Each of the medallions 10, 24, 210 can also include a clock to record receipt of the data from any of the devices/monitors/sensors sources disclosed herein and time stamp data collected, data transmitted, data received, or any other use of medallion(s) 10, 24, 210, such as if/when the code(s) on the medallion were accessed and/or read. For example, the communication(s) which are carried out to communicate data can be achieved by a separate communication(s) device which can be a transmitter, a receiver, and/or a transceiver, any of which can be a function of the medallion(s) 10, 24 and/or 210. Additionally, signal(s) from the various sensor(s), monitor(s), reader(s), or other data gathering devices, may individually, or collectively, be subject to signal processing to transform or convert the data/information. For example, signal processing may include the steps of amplification, filtering, compression, integration, and delay, continuous and discrete time signal processing, and other analog and/or digital signal processing known in the art and may be included as part of the medallion functions. The signal processing can be performed by a digital circuit, a computer, or other technology. A second medallion 24 in FIG. 6, 210 in FIG. 1J, and 10 in FIG. 1J can be used together on the same halter/harness/hackamore/bridle; the medallions 10, 24, and 210 can carry and communicate and receive indicia, such as a bar code, or smartphone/device readable QR code, or other smart communicating/computer device readable codes and/or voice/text messages and/or other sent/received communications or codes or technologies. The indicia may provide the smart-device reader/entity of such indicia and/or place the reader/entity directly into contact by-all-communications/frequencies/microwaves, etc. transmission devices with authorized veterinarian(s)-professional(s) entities or the owner(s), stable and/or authorized/designated aid and custody custodian(s), trainer(s), or care-center(s) authorizing/locating/recovering/remunerations for out-of-GPS safe-zones/lost animals, and other animal urgencies/emergencies, including per computer-telephony, etc. Further, the medallions 10, 24 or 210 may be connected, via various communication(s) and transmissions, such as wired and/or wireless networks, satellite, cell tower, and other/all signal processing equipment-communicated to smart computing and/or communicating smart devices, which when activated by a simple gesture (e.g., pressing a button, and/or touching smart device keys/screens, and/or scanning/typing a smart-device code/message/number/text or per other indicia and/or instrumentalities) connects to a veterinarian, owner, and/or designated authorized and care-lost-missing-recovery-custody-custodians and/or via computer-telephony and/or persons/entities, etc. Alternatively, the medallion(s) 10, 24, 210, can also contain a memory component, preferably an upgradeable memory, and/or other capabilities in which numerous types of communication information can be time stamped, received/included/stored/transmitted, the medallion(s) 10, 24, 210 functioning also as a smart communicating-and-sending/receiving device nexus for enjoyment, health, and safety, connecting to a specific ownership(s) or animal(s) archived identity(s), for Animal Health and Safety System authorized care, custody/transport information and instructions for the animal(s), when in an urgent/emergency/unsafe situation, and/or other optionally real-time animal health and safety communications, and/or animal-specific and/or general veterinary information, and/or other stored information and/or records relevant to the animal(s) ownership(s)/custodian(s)/designate(s). The medallions 10, 24 can include information for the animal if lost/missing when found, and/or located in a designated-unsafe/lost GPS locations, and/or other real time animal health and safety communications and/or animal-specific and/or general veterinary information and/or other archived information and/or records relevant to the animal ownership/custodian. Furthermore, the medallions 10, 24, 210 can be used to control ambient video and/or other visual images, also controlling a light or series of lights 30, 31 FIG. 1B, on the halter/hackamore/bridle/harness, preferably light emitting diodes than can function as visible forward facing and/or overhead illuminating light(s), device(s)/sensor(s) optimally positioned optionally per the max-comfort and well-being of the animal, breed and species, such that the animal can be located by search from the ground or air (e.g., by aircraft and/or drones); and/or warning/signaling lights and/or for all herein disclosed functions/operations a smart computing/ communicating optionally wearable halter/harness/hackamore/bridle device(s), and/or controlling flashing and/or warning lights when dusk falls, and/or may comprise a speaker to emit auditory sounds, such as beeping, and/or voice messages generally, and/or when the animal is surrounded by brush, or otherwise out of sight, to assist in locating/recovering the out-of-GPS, and other location technology, safe-zones missing animal(s) and/or other animals in urgent/emergency and/or unsafe conditions and/or situations, and/or other functions, purposes and services.

Medallion(s) 10, 24, 210 can act as senders and/or receivers of signals to perform any function on the animal, such as turning on the lights or speaker, energizing the thermal, vibratory, or medicament administering device in contact with the animal (including topical, transdermal, subcutaneous, or internal of the animal pharmaceutical, hormone, antihistamine, or other pharmaceutical and/or medicament, and/or other actions, procedures, treatments). The medallion(s) 10, 24, 210 can also act in conjunction with the GPS in multiple ways, including to illuminate the harness lights, video, or initiate other action on the animal, whenever the animal strays from its electronically/otherwise designated "safe location," and/or a smart communicating device may activate halter/harness/hackamore/bridle lights. A read/write/re-programmable memory within the medallion(s) 10, 24, FIG. 1A, 10, 210, FIG. 1J, can be updated upon change of circumstances (e.g., new veterinarian(s) or designated authorized care/custody/recovery/custodian(s)/entity(s), and/or a new authorized care-center(s) is designated, calling for new communication and/or transmission arrangements). The medallion(s) 10, 24, 210 may also be programmed to change the contact communication sending/receiving information, (e.g., telephone, email address, per all communication antenna, equipment, devices, frequencies, (e.g., microwaves) and modes, both specifically and generally for this disclosure, etc.) of the authorized and authorizing care/custody custodian(s) and/or contact entity(s), as well as function as a human/animal enjoyment, health and safety communications and monitoring per real-time, and an animal-ownership-designate information and records archived nexus to maximize the comfort and well-being of the animal. While we have illustrated one medallion 210 on harness 200, and up to two medallions 10, 24 on the same halter 40, there may be multiple medallions on a single animal, especially where the trappings/tack for equines, and/or the harness(es) for canines/felines, provides additional points of attachment for multiple medallions on animal control and restraining equipment, trappings/tack, as shown in FIG. 1J. Alternatively, as described above, the functions of a single medallion 10, or the functions of multiple medallion(s) 10, 24, 210 may be separately carried out by multiple devices, without departing from the scope of the instant disclosure.

When linked with a two-way smart computerized-communicating device(s), preferably a smart phone/tablet/laptop/computer and/or personal wearable device and/or assessing/analyzing platform(s) and/or program(s), the medallion(s) 10, 24 FIG. 1A, also 24, FIG. 6, 210, FIG. 1J, can be activated to enable two-way voice/email, SMS or other communication(s)/transmission(s) devices/modes with a designated/archived and/or real-time contact(s) with persons or entities. A two-way technology medallion communication device, optionally in addition to the medallion(s), may be attached to the halter/hackamore/bridle/harness or carried by the animal, and/or that may be at a position(s) remote from the halter/hackamore/bridle/harness animal and/or medallion(s) 10, 24, FIG. 1A and 24, FIG. 6, 10, 210 FIG. 1J, and can be included in all halter/hackamore/bridle/harness embodiments and usages.

The thickness of the medallion(s) 10, FIG. 1A, (and/or 24, FIG. 1B) also as shown in FIG. 5B, and 24, FIG. 6, 210, FIG. 1J, may be made variable to house all the multiple possible power source(s) (e.g., battery(s), etc., or other power sources) and micro/nano-and-other circuitry, such as signal processing, other technologies necessary to permit all of the medallion's enjoyment, health and safety real-time and stored-recorded communication(s)/transmission(s) nexus tech-capabilities/functions; the medallion 10, FIG. 1A is preferably permanently mounted on one of the right hand straps 43, FIG. 1A and-or left hand straps 44 by permanent fasteners, such as rivets (not shown) or in other positions such as 10, 210 on harness 200 FIG. 1J, per the maximum comfort of the animal, and/or veterinary assessment, in order to prevent removal thereof from the halter 40 or harness 200; medallion(s) may be positioned optionally per veterinary science, functions, and the lifetime well-being of the individual animal(s), breed(s) and species. Alternatively, the possible power sources for the medallions 10, 24, 210, as well as the GPS, lights, video, speakers and other functions described herein may be separated from the medallion itself (or the GPS, lights, etc.) and be provided as one or more independent element(s) connected to the medallions 10, 24, 210 (or the GPS, lights, etc.) to provide any required or supplemental power to facilitate the functions described herein. A central processing unit (CPU) can also be provided to monitor/regulate/and control power sage for the functions described herein. It is also within the scope of the present disclosure to permit artificial intelligence (AI) to monitor/regulate and control power usage and other capabilities, functions, purposes, services for the medallions 10, 24, 210 or other power requirements of the elements using varied power sources as disclosed herein. Artificial Intelligence ("AI")-programming manages-monitors-orchestrates all energy and-or power usage from all energy sources . . . solar, battery, charging, plug-in, animal-movement-sourced/pendulum, gas generator, solar panels, etc.; location(s) of AI unit(s) on/in/borne/remote/close to animal.

Self-correcting systems have feed-back-loops for self-correction, e.g., the basic thermostat-controlled home-heating unit corrects too-hot and/or too-cold to the pre-purposed-temperature-range. The Vet's kidney-ailment "hypothesis" (discussed below) was a system-self-corrected (per human and/or AI pre-programming) to the heart-ailment analysis, per-DMS-data system-read; the correction was from a (human) veterinarian diagnosed kidney-ailment, found not to be a kidney ailment by the disclosed system and repurposed/reprogrammed to a correct diagnosis of heart-ailment. Thus, the system converted raw-granular DMS-bodily-processes-data . . . discerned to heart-ailment information . . . un-understandable data system-discerned to understandable information. Thus, a NOAA hurricane warning is raw-granular-weather-data=discerned to an understandable hurricane communication. Each system-self-correcting-feed-back-loop has a purpose . . . the home-heating-system is purposed to maintain temperature . . . the DMS(S) System is purposed to maintain health, therewith to sustain life, discerned per veterinary-medical-scientific knowledge.

DMS provides data_for discernment per DMS-Sources . . . thus DMSS . . . Sourced from NOAA=potentially life-impacting-(terminating=unhealthy)-hurricanes . . . to life-impacting-sustaining veterinary-medical-scientific knowledge-applied. Thus the system's purpose generally . . . health-purposed . . . per life-impacting-sustaining-practices, that avoid and/or delay life-terminations; per our system re-purposed hot-truck-cab-animal-rescue (discussed below) . . . the All-A-OK cool morning pivoted to a hot-cab-animal-rescue, and the system re-purposed likewise . . . from All-A-OK-System-well-being mode . . . to urgently organizing and implementing an animal-rescue . . . by the System blanketing via communications locations-and-interests-relevant Care-ful entities . . . per emails, phones, registrants, rewarded-rescuers, smart-wearables, texts, volunteers, etc. . . . thereby turning the life-impacting-terminating-hot-truck-cab . . . to life-sustaining animal-rescue to cooler situations.

The purpose of the animal-in-hot-cab system-example is likewise maintaining-sustaining animal health; the system re-purposed=self-correction-pivoted=from All-A-OK-health-wise on a cool morning . . . to an urgent hot-day hot-cab animal-life-impacting-threatening situation, the System blanketing location-relevant and Care-ful-relevant animal-rescue-entities, per pet-rewarded-rescue protocols.

FIG. 6: Away-from-animal communications, functions, recipients 12, 14, 16, 18 and 20;

[28/triangle-schematic representation of safety halter/harness/hackamore/bridle device(s), functions, and/or sensor(s) halter/harness/hackamore/bridle optional per maximum animal comfort attachment locations];

12—all data/information communications by all modes to all devices and recipients.

14—to/from computer(s)/platform(s)/program(s), cloud computers, computerized archives, and/or smart portable and/or worn personal and/or animal borne/monitoring device(s);

16—stall/housing and-or shelter mounted/located devices, monitors and-or sensors, e.g., audio, (contagious coughing), visual/video imaging and/or behavior-pattern-monitoring, above, about and/or ambient to the animal;

18—real-time and/or records-sourced communication(s)/transmission(s) to/from animal owners, animal devices, veterinarians', professionals' and designates' computers and portable and/or sending/receiving/communicating borne and/or worn smart devices, per analytics, platform(s) and program(s);

20—satellite, GPS or other location technologies, monitoring, safe and unsafe GPS location(s)/zone(s) per electronic/other tech-boundary designations, and health, safety and activity analytics, alerts, notification zones, and/or other away-from-animal health, enjoyment, safety, photo, video, and/or sensor device(s), monitoring domestic and/or non-domesticated fur-bearing, game and/or nuisance animal(s) via balloons, drone(s), airplane(s) and/or aerial and/or other units, and/or non-domesticated fur-bearing, game animal(s) safety from poachers, and/or other monitoring.

FIG. 6 numbered elements: animal(s) body/health and safety halter/harness/hackamore/bridle device(s) and/or device(s)/monitor(s)/sensor(s)/sources sourced from painlessly-per-veterinarians-anesthesia inserted/ingested/implanted-in-animal-body, on-animal body, ambient-to-animal-body(ies) communications 22, 24, 26, 30;

22—against animal fur-hair-skin safety halter/harness/hackamore/bridle device(s)/monitor(s)/sensor(s)/sources (also FIGS. 2-4), communicating external-to-animal health and safety vital signs and processes sustaining/terminating information, to signal-booster-transmitter(s) 24 and-or directly to 12 and-or 14, 16, 18, 20 platform(s)/program(s) analytics/computers/device(s), human wearables, communicating sending/receiving/archive/smart devices;

24—singular and-or aggregating signal-booster-transmitter(s), communicating-monitoring sensing vital processes and signs device(s) and-or sensor(s), functioning per 22 above;

26—away-from-animal-facing safety halter/harness/hackamore/bridle device(s), monitors and/or sensor(s) and/or sources (also FIG. 2-5) functioning per 22 above;

28—triangle-schematic representation of on-animal safety halter/hackamore/bridle/harness device(s) and/or sensor(s) at optional-for-optimal halter/hackamore/bridle/harness equipment/trappings/tack attachment locations;

30—internal-to-animal-body device(s), monitor(s) and/or sensor(s) and/or sources surgically implanted painlessly per anesthesia, and/or inserted, and/or swallowed, functioning per 22 above;

32—dashes (- -) indicate lines of data/information communication(s) and/or transmission(s);

34—arrows indicate device, monitor and/or sensor functions.

FIG. 6—All devices/monitors/sensors 22, 26, 30, FIG. 6 communicate directly, and/or via signal-booster-transmitter 24, to/from remote-from-animal devices/wearables/computers/archives/smart portable devices/programs/platforms/persons/entities 12, 14, 16, 18, and/or 20.

Figure 7:
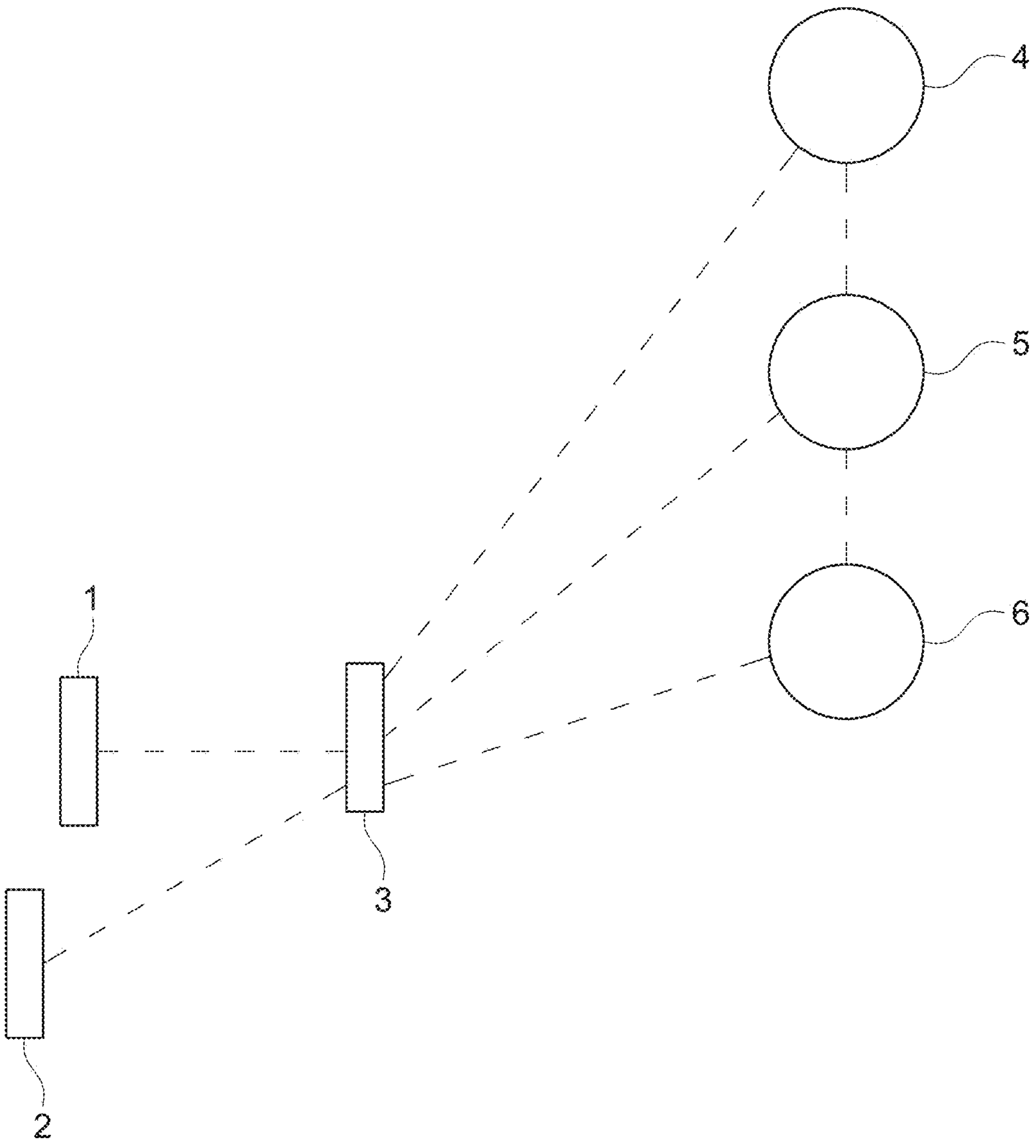
FIG. 7 is a schematic safety system illustration including components implantable devices/microchips or other monitors/sensors/sources 1, and on-animal devices/microchips or other monitors/sensors/sources 2, an optional communication(s)-signal-booster 3; a GPS or other location technologies unit 4; an archive(s) 5; and a network of smart devices (linked communications via computer(s), laptop(s), tablets, phone(s) and wearable(s)) 6, plus additional capabilities, functions, sources and services, disclosure following.

FIG. 7: U.S. Pet Parents Reciprocal Health And Computer-Recorded ID Support Method—sourced capabilities and services, per Animal Safety System authorizations: Implanted 1, and/or out-of-animal body 2 borne animal/ownership/custody ID-identification microchip(s)/device(s) 81 and 82 (FIGS. 1D, 1F)—also monitoring internal animal life-impacting, sustaining and/or terminating vital conditions/signs—also monitoring internal and/or ambient and/or external to the animal body(ies) conditions per optional communication-signal-processor 3 FIG. 7, 113 FIG. 8; including GPS location/other technologies service(s), safe and unsafe zone(s) technologies/missing alerts-communications, and authorized animal search-location-recovery-custody-care-reunion-transport-remuneration per licensed professionals/persons/entities. (4) for databased recorded animal(s) and/or ownership(s) and/or designates identification(s)-communication(s), transmission(s), optionally including animal health history, information and instructions, via all devices/modes, for database included/recorded animal(s) and ownership(s)-designate(s) 5; specifically and generally for this disclosure, also including smart device(s) defined as communication(s)/transmission(s) by all modes and devices—computers, laptops, tablets, phones and wearables 6, multiple different capabilities and functions optionally combined into a single device/monitor/sensor, optionally using booster-communication(s)/transmission(s).

FIG. 7: Optional additional FIG. 7 capabilities, functions, services and technologies: a no-fee and/or for-fee computer-registered animal care service(s), containing comprehensive animal and/or ownership-stewardship-designates information, optionally by an implantable and/or borne microchip 1, 2 per FIG. 7, and/or optionally other in-body and/or out-of-body animal borne identification means, identification specifically for each databased individual animal and its complete ownership identification information, including databased animal and/or optionally real-time communicated veterinary-health-history-safety information. Also optionally, bond may be posted and/or authorized by the ID Archive owning-sponsoring entity(s) and/or authorized by Animal Safety Databases System Principals, for lost/missing ID-archived animals authorized location-recovery-custody-care-reunion-undertakings. Optionally, services for ID-archived animals-ownerships may also include, yet are not limited to, optional GPS and/or other technology animal safe zones, locations and non-safe-lost/missing communications/publications/social media, optional Animal Safety Database System authorized professional/volunteer animal care-custody-recovery and ownership reunion undertakings, including, but not limited to providing a bond for compensating the informing-persons, reporting unlawful actions, and/or threats thereof, taken against the archived identities of, and information about ID-archived, animals-ownerships-designates included/recorded in the archive(s) and optionally the private and/or police investigation of such unlawful acts and/or threats. Other services for ID-archived animals may include optional lifetime animal care and/or endowment therefor, optional Animal Safety Database System sponsored animal ownerships-sourced pooled-dollar-resources for veterinary care cost-sharing for archive database-recorded animals/ownerships, and optionally pre-authorized professional animal-ownership care-custody-identification-location-transport-recovery-remuneration-reunion per Animal Health and Safety Database System authorization(s)—as enabled per disclosures and FIGS. 1A, 1B, 1C, 1D, 1E, 1F, 1G, 1H, 1J, 2,3,4, 5A, 5B, 6, 7, 8 and 9 capabilities, functions, services and optional technologies/platforms/programs/interfaced/integrated.

FIGS. 1 through 6, as disclosed, via halter/harness/hackamore/bridle-borne comprehensive health and safety services, protects financially and/or emotionally valuable equines-ungulates, canines and felines, and other animals.

Summary Intro: Summary Example #1 A "Pet Parents" Animal Care and Enjoyment-Support and Reciprocity; companion animal(s) enjoyment also involves much care-and-effort, thus companion animal owners'-stewards' duties-and-enjoyments sharing-and-reciprocity per no fee or fee. The Pet Parents' Careful Computer-Generated alignments and screenings identifies, and per privacy protocols and screenings, confidentially accesses fellow animal-owner's-steward's and their companion animals, optionally via photos of companion animals/owners. The ID Registry includes zip codes, and contact, and optionally descriptive, information for owners/animals, and optionally includes volunteer availability/interest in assisting-sharing-supporting other companion animal owners duties and enjoyments, e.g. walking the by-zip-code-neighbor's dog when said dog owner is recovering from knee surgery, or cat-sitting when the cat owner is away on business, or per screening, "Corgi Owner A" welcomes "Corgi B dog" into "A's home", and inversely has "Corgi B's Owner" likewise take care of "Corgi A dog" reciprocally into Corgi B's home, per any companion animal species/breed, etc.; such reciprocal companion animal owner-steward support-sharing greatly aids animals' well-being, being fully consistent with the animal-health and well-being-intent of these disclosures, e.g., as optionally companion-animal-members-of-the-family are reciprocally in companion-animal-friendly-residences, at home with other fellow-furry-family-members, plus human attention and care, or out walking, etc., rather than starkly-less-friendly harsh kennel-boarding cages. Joint neighborhood companion-animal-walking and enjoyment and reciprocity is heartily beneficial for owners and animals alike. Such owner-steward-socialization is evident in animal-friendly-parks, where owners happily socialize and companions robustly romp; Pet Parents comprehensive ID Registry, by providing information for mutual and reciprocal sharing of companion animal duties and enjoyments, builds strong socially-bonded friendship-dynamics, substantially benefitting both companion-parents and furry companions, both physically, (e.g., walking), and mentally (e.g., companionship); such ID Archive sponsorship of caring-connections, maximizing owners reciprocal and shared companion animal enjoyment, wellness activities, and support sharing, is yet another aspect of, and fully mission-consistent with, enhancing the lifetime well-being of canines and felines . . . likewise with Animal Safety System computer-recorded owners' equine care sharing, socialization and support too, per companion animal disclosures, including equines.

Summary Example #2A The "Care-ful System Component": "The Internally Self-Correcting Re-Programmable Communicating Animal Health, Safety and Well-Being Computer System" . . . aka "The Re-Programmable System"—is more fully detailed in this Disclosure below. Please note, the System-includes its "Care-ful Component," disclosed by this Intro, and the following paragraphs; "The Care-ful Component" fully benefits from "The Re-Programmable System"; please also note that "The Care-ful Component" is generated by The Re-Programmable System's/AI/Programming/Self-Correction/Re-Programming; the System's self-correction capabilities are purposed to assess and align animal care-givers' backgrounds and experience-skill-sets with Animal Owners-Stewards Care-Designates. To accomplish this, the "99-item Questionnaire", characteristics and interests' profile, of each Care-ful Registered Pet Parent and their Companion Animal, and prospective care-givers, veterinarians to animal-loving-volunteers, per their System Registration.

In summary, the Re-Programmable System A) fully monitors the health and safety of Pet Parent's Companion Animals; B) per (voluntary) Pet Parent background-checks, incorporates big-data information and insights, plus additional person-animal information, and C) dynamically combines the System-sourced animal health information, and the animal and Parent background, and big-data info, and other information, including real-time health, safety and well-being data—plus System self-generated relevant-aligned-resources—per privacy protocols and permissions.

The Internally Self-Correcting Re-Programmable Communicating Animal Health, Safety and Well-Being Computer System, of itself, correlates and compiles Care-ful background, health data, characteristics, and orientations, of interest and value to Pet Parents and their Companion Animals and communicates the composite correlating the personally aligned information to Pet Parents, both personally aligned-relevant and animal-aligned-relevant.

Summary Example #1 AA—Care-ful Computer System Component-Self-Correcting-Re-Purposing; The animal health and safety monitoring Computer System self-senses the Companion Animal has strayed from its GPS defined safe-zone; immediately the Self-Correcting-Self-Purposing Computer System purposes, self-issuing an email-blast that Ol' Rover has slipped his backyard, to relevant neighborhoods, also Care-ful Registrants, "Nextdoor", Animal Control Officers, and all other location-relevant pet caring parties-organizations—that the Self-Purposing-Computer-System has researched and action-archived, relevant to Care-ful Component Pet Parents . . . the Computer System's reunion-reward is announced-communicated for Rover's return-reunion to the owner, and-or payment to any veterinarian for holding Rover 'till owner-reunion, plus palliative care, as necessary; all veterinarians in the relevant zip-code-area are also notified, per the Computer Systems purposed=aka self-collected email resources . . . plus all location-relevant Care-ful Registered Pet Parents smart-communicating-devices are notified . . . as well as the Pet Parent, of course. The result: Instantly all area-relevant pet caring entities are in-the-search for Ol' Rover . . . found via Nextdoor in the 'hood, owner-reunion forthcoming forthwith.

Summary Example #2 AA—Care-ful Computer System Component-Self-Correcting-Re-Purposing: The animal and owner-steward's health and safety monitoring Computer System "knows" of the owners upcoming knee surgery, as "health background & issues" is one of The 99 Background, Characteristics and Interests category-options owners may provide, per privacy protocols. Thus, our Self-Correcting Re-Purposing Computer System "self-corrects" from #1=straying-Rover's owner-reunion . . . and multi-re-purposes to researching-archiving location-relevant Care-ful Registrants whose "99 Profiles" tell of willingness "to dog-walk during owner-ailments". Also, our computer's big-data-access has screened owners per like interests and orientations . . . The Simpatico Score. Thus, when the time comes for knee surgery, our owner is presented with the Computer System's alignment of "99 Dog-Walking Info" per big-data Simpatico alignments=interests and orientations . . . for the owner to select a walker; the most convenient closest-location "care-ful-walker" does not have an optional Computer System background report on file . . . so our knee surgery owner, in need of dog-walking, selects an almost-as-convenient care-ful-walker, with a background-report. All information is selectively provided per privacy permissions, procedures and protocols.

Summary Example #3 AA—Care-ful Computer System-Self-Correcting-Re-Purposing: The Pet Parent's Companion Animal becomes lethargic, slow-moving. The veterinarian suspects a kidney ailment, and painlessly-via-anesthesia inserts a blood monitoring-device. Per Disclosure #7 & #8, the short-range-communications of the implant are gathered per #1 & #2 communications, to the entire Computer System #1 through #33+Intro+Notes . . . and per #6 nano-computer-devices, including smart communicating devices and aggregated computer-banks-clouds. The implant includes a nano-tech-computer, that to-from communicates with the functionally integrated communicating System—and its nano-micro-mini communicating devices—and its smart communicating portable devices—and its computers, individual and banked/clouds. The to-from communicating nano-computerized-monitor-implant—functionally to-from-communications-System-integrated—nano also including large-sized computers and computer-cloud-aggregations-integrations—as well as computerized communication portables . . . all operating in functionally integrated unison. The implant reads nano-device-sourced granular data . . . seeking via blood-monitoring the veterinarian-sought kidney functions profile. The granular-data-read, per the implants functionally-System-integrated nano-computer-to-computers-data-source, reads kidney-blood-analytics-data—also sensing heart-rate-pulse-pressure anomalies; the functionally-integrated-System multi-re-programs/re-purposes to kidney-health-ailment-analysis and to heart-health-ailment-analysis—from a granular-raw-data-read—also per data to profiling the animal's heart ailment-disease analysis—and the animals data driven kidney analysis (as healthy). Thus, our owner-steward of her Companion Canine, now knows slow-moving-lethargy is heart-ailment-caused, rather than kidney-disease-based . . . all subject to further analyses of archived granular data . . . and the integrated nano-to-banked-cloud-computer-programs that profiled heart-ailment-disease, rather than kidney-ailment-disease. The symptoms the veterinarian observed rightly suggested kidney disease; yet the nano-computer-bearing implant-sourced-data, per the functionally-communicating-integrated AI and-or programmed System analyses . . . discovered healthy kidneys, yet an ailing heart. (Additionally—the Re-Purposed-Integrated-Computers self-select—veterinarians by-heart expertise-breed-body-type-size-location—also big-data-internet info on dog heart health, etc., all information per as extensively as Registered Care-ful Dog-Animal Owner-Steward requests of Computer System/AI/Programming.)

Discussion—Notes for Summary Example: #4 AA) The Care-ful-included Re-Programmable System, nano-to-banked-cloud computer(s), maintains a computer-constructed aligned assemblage of articles, information, research publications, etc. per real-time and-or archived animal health, safety, ailment-disease-info, that also aligns from internet, big-data, other sources per Registered Owners' "99-Profile" . . . also including computer System assessed individuals capable and experienced in equine care, custody and tasks. The experience of equine care-givers is summarized and categorized by the Computer System—including the breed of equine—and the care-tasks performed, both by duties conducted, and the time-spans involved, e.g. Santa Anita Racetrack Stables—thoroughbred grooming, three race seasons (e.g. example not limiting). Thus, these summaries may vary from "daily feeding, exercise, brush-down of friend's quarter-horse—one summer" . . . to . . . "nine years—experienced in all aspects of stable management—multiple Arabians" . . . all analyzed, assessed, compiled, matched, sorted by the Computer System per Registrants "99-Profile", internet alignments, big-data relevancies, and other information. (Professionals and persons offering equine expertise and-or services are likewise "scrubbed" by the Computer System.) Individuals who are Computer selected by the System for Registered-Owners, and there-following Computer System selections-per-Owner-profile-alignments, are interviewed by equine owners/care-principals to confirm a good Computer-driven "99+ Simpatico" fit, both personally and as to both duties and horse(s) involved. Computer System alignments also screen all manner of equine aficionados, from professionals to horse-loving-volunteers, including those seeking others with whom to ride. All information, per privacy principles-protocols, can and may include complete contacts and locations information-addresses-zip codes-private and-or published phone-text numbers-internet, email, texting connections-websites-social media-all other connection-location-social-media relevant personal information formats-means—to assist convenient communications and-or meetings and-or joint-group activities—Computer System assembled per alignments and associations, by contacts and connections.

Summary Example #5 AA) The option of background-checks is also offered; also, care-participants can and may be evaluated—"experienced rider with great attitude" . . . (or otherwise). The Equine Care-ful Self-Correcting Computer System thus sums to assessing and screening a full variety of horse lovers . . . from volunteers . . . riders seeking fellow riders . . . to equine-professionals; all manner of care-tasks and equine-activities are included. Tasks may be equally exchanged reciprocally and-or remunerated, and costs may be defrayed and-or reimbursed, per the parties agreed arrangements; all-in-all the Computer generated System, for-fee and-or no-fee, provides access to the full range of horse lovers . . . from experienced stable managers—to those seeking riding companions . . . from mucking-out-for-rides volunteers—to for-fee groomers—and equine-expert-veterinarians and professionals. All animal-owner-designate relevant information is Computer compiled. (Singulars can and may be plurals and-or combinations thereof.) The Equine Care-ful Computer Systems summary result—happier-and-healthier horses-and-humans . . . cats and dogs too!

Summary Example #6 AA) Animal Care and Enjoyment—Support and Reciprocity: Companion Animal(s) enjoyment—canines, equines, and-or felines—also includes much care-and-effort—thus companion animal owners-stewards-designates duties-and-enjoyments are better shared, as well as reciprocated; volunteered assistance-pro bono services-care and maintenance duties exchanged for riding, walking, animal-sitting—per no-fee and-or for-fee reciprocities, remunerations, reimbursements—such friendly-neighborly-accommodations are vastly better for animals' well-being, than boarding cages, often with highly limited exercise—plus owners-stewards-designates away-from-pet-abandonment-issues bonded to truly-kind-care concerns. The Care-ful Included Self-Correcting Re-Purposing Computer(s) System identifies, and per privacy protocols (and optional and-or not optional gradations of background screenings), assesses fellow animal-care-givers and-or animal-owner-stewards and their companion animals; animal, owner, care-giver, volunteer, etc. information and experience levels—plus addresses, contacts, locations, references, social media, phone-text-numbers, laptops, tablets, wearables aka smart-computerized communicating-devices, as disclosed throughout this document, and other relevant information, optionally including images, photos, videos of, and-or voice-written narratives from-about companion animals-owners and-or care-providers and-or other entities.

Summary Example #7 AA—The Care-ful Computer-maintained System is inclusive of all owner-animal-designate attentions, caring, duties and responsibilities, per-privacy-permissions-protocols and options, also includes addresses, and the full range of complete contact and-or location information inclusively, from social media to very private personal phone numbers, while not limited thereto; optionally, all System included parties descriptive assessment-information about, and-or for, owners-animals-designates, can and may/may-not be provided to System included-parties. Such may include (while not limited to) volunteer and-or for-fee availabilities, interest and experience in assisting-sharing-supporting companion animal owners duties and enjoyments—e.g. walking the by-zip-code-neighbor's dog when said dog owner is recovering from knee surgery—cat-sitting when the cat owner is away on business—regular caring, feeding, grooming and exercise for very-busy get-home-too-late-therefor Pet Parents Summary Example #8 AA—Reciprocity: Per gradations of Pet Parent-care-provider background screening options, "Corgi Owner A" may welcome "Corgi B dog" into "A's home"—and inversely has "Corgi B's Owner" likewise take care of "Corgi A dog" reciprocally in Corgi B's home, (unrestricted to animal breed-type, etc.); such reciprocal companion animal owner-steward-designate support-sharing greatly aids animals' well-being, and is fully consistent with the animal-health and human well-being-intent of these disclosures; e.g., as companion-animal-members-of-the-family are reciprocally in companion-animal-friendly-residences and-or equine friendly facilities, at home with other fellow-furry-family-members, plus human attention and care, or out walking, riding, etc., rather than often starkly-less-friendly harsh kennel-stable boarding cages-stalls. Such reciprocity likely initiates via joint dog-walking, riding, therewith finding simpatico personalities and animals—with reciprocities evolving.

Summary Example #9 AA—Support: Joint neighborly-collegial companion-animal-walking-riding and Care-ful enjoyment and caring-reciprocity relationships are heartily beneficial for owners and animals alike. Such owner-steward-designate-socialization is evident in animal-friendly-parks, at communal stables, where owners happily socialize and companions robustly romp-n-ride; Pet Parents' Computer Driven Comprehensive Care-ful Self-Correcting Health and Safety System, by providing information for mutual and reciprocal sharing of companions duties and enjoyments, builds strong socially-bonded friendship-dynamics, substantially benefitting both companion-parents and furry companions, both physically, (e.g., riding, walking), and mentally (e.g., animal and human often-grouped dog-walking horse-riding cat-sitting reciprocal companionships); such System for-fee and-or no-fee sponsorship of caring-connections, maximizing owners reciprocal and shared companion animal enjoyment, wellness activities, support and reciprocity, is yet another aspect of, and fully mission-consistent with, enhancing the lifetime well-being of both animal owners-stewards and their furry pals-n-steeds Summary Example #10AA—Registrations: Equine Owners-Stewards and their equines register . . . providing profiles, photos and-or comprehensive information, as disclosed throughout this document . . . as well as non-owners, care-offering-persons, and-or volunteers, for differing fee-structure-options and differing System accesses. Disclosures #1AA, Intro through Summary, are also completely-fully applicable to canine, equine and feline System participants and entities registered therein, including comprehensive information provided, as itemized throughout this disclosure; likewise, The Canine-Equine-Feline Care-ful Self-Correcting Re-Programming System-Component includes veterinary personnel, and-or other professionals, care-fully selected as expert and experienced in their animal-specialty. The health, safety, and well-being capabilities, functions and services disclosed following in this Provisional Disclosure; the Computer-Composed Care-ful Component is fully System integrated with the Re-Purposing Self-Correcting Health & Safety System . . . yet may also be deployed separately.

Summary Example #11AA—System Information: Accessible by System Registered Entities to-from communication means, smart devices, wearables, and-or per fee and-or System Sponsor licensed permissions; computers-platforms-processors-programs-servers, including artificial intelligence, combine in dynamic union to serve System included entities care, custody, functions, needs, sharing, reciprocity, remuneration, etc.

Summary example #12 AA—Resources: Animal care may be expensive; per Registered Owners, designates, other entities in and-or not-in Registered System Participation—pooling of funds can and may be employed—to address, defray, lower, monetize, share—animal care costs, as defined by System Sponsors Executed Documents—and-or the Receipt-for-Animal-Inclusion—and-or the Receipt for Funds Provided—per applicable government law, policy and practice.

Summary Example #13 AA—Lifetimes: Lifetime-love-bonded Companion Animals . . . canines-equines-felines . . . can and may often outlive their Owners-Stewards-Families; lifetime care for Companion Animals, after the death of the Companion Animal('s') Owner/Steward, can and may be funded, by Will or other Document, and the Companion Animal lifetime-cared-for, as defined in System Sponsors Executed Documents, and-or the Receipt-for-Funds Document, for Registered and non-Registered Animal Owners-Designates per applicable government law, policy and practice.

Summary Example #14 AA—Care-ful entities—and-or Registrants per Sponsors concurrence—can and may post Bonds favoring persons reporting to authorities unlawful acts against animals—and-or Bonds for locating-returning lost Care-ful System Registered owners' animals, per the Executed System Sponsors Bond Concurrence Document.

Summary Example #15 AA—Summary: Animal care-and-healthful-stewardship entails much joy in tandem with many tasks; the System and Method at once cares-n-shares care-ful tasks-n-joys—sponsoring greater health and happiness for both animals and humans. Lifetime well-being of animals may continue past Pet Parent Stewards' lifetimes, as well as may prove expensive. Such Lifetime well-being may include A) posthumous pet care, B) pooled funds to reduce major pet care costs, C) bond postings against unlawful actions per System Registration included animals/ownerships, D) likewise bond-postings for lost animal(s)' location-return-reunion. Result: In healthful union—animal-and-human life-improving Comprehensive Canine-Equine-Feline Care-Sharing-Socialization-and Support.

FIG. 7: Pet Parents Animal Safety ID Registry—optionally provides all ID registered animals and owners-designates with archived and real-time comprehensive identification, health, safety, missing-animal information, GPS/other technologies safe zone-unsafe zone communications, and aid/care/custody authorizations to archived animals/ownership via computer/telephony and/or personal operator(s), smart-device accessed and optionally operated-serviced-sponsored separately, in part, and/or wholly-from halter/harness/hackamore/bridle-borne comprehensive health and safety registries, operations and service FIG. 7 is fully safety-mission-consistent with and complementary to the health and safety of highly valued animals, both financially valuable and-or life-long love-bonded emotionally valuable animal companions, and is a method for implanted/not implanted identification (hereinafter "ID") microchip identification, and/or other animal-borne comprehensive registered identification, in combination with GPS, or other location and/or tracking services and/or safe-zone/unsafe-zone location technologies, and optionally owner-designate noticing via all communication means, and licensed professional care-custody-transport authorizations, plus health vital signs monitoring, sensing and communicating, via all devices, and associated animal health and safety services, and their ID registered ownership(s), steward(s), designates(s), via smart-computerized-communicating-devices-wearables platform-program interfaced/integrated. The Animal-Safety ID System and Method is not halter/hackamore/bridle/harness dependent; thus, disclosure of the single and-or optionally multiple implantable and/or animal-borne microchips-devices-monitors-sensors, for identification-monitoring-reporting to owner(s)-designate(s), with at least three disclosure iterations, optionally all of the following separate, singular capabilities, functions and services disclosure iterations, as itemized within subparagraphs below, for computer-recorded animals-ownerships-designates.

1) Heart health-signs, and/or . . .
2) safe-unsafe GPS locations reporting, and/or
3) other health and safety monitoring(s) of archived animal(s), communicated-reported to ownership(s)-stewardship(s), and-or designate(s), and/or
4) smart communicating device(s), wearables alert(s) and/or notifications communicated to ownership(s), and/or entity(s), and/or veterinarians, and/or animal professionals via comprehensive text/images, and/or social media publications
5) medically-coded-archived-large and-or-small-animal-health-information, and/or
6) functions and monitoring(s) readable by a smart communicating device(s), wearable(s) for registered animal/ownership identification, and/or
7) animal-veterinary records, and/or
8) via chip-sourced direct connections and/or communications to a smart device(s) per 6 and 7 preceding, also 22, 26, 30 FIG. 6, via medallion and/or signal booster—24 to 12, 14, 16, 18, 29 via 32, FIG. 6—1, 2, 3, 4, 5, and 6, FIG. 7 capabilities and function for real-time communicated veterinary history/information, and/or
9) missing animal notice communications/publications/news-social media, and/or
10) Animal Safety ID System and ownership authorized media notices, general communications for lost/missing professional/volunteer animal/recovery, and/or
11) Ownership(s), designate(s) lost-missing animal care/custody and recovery authorizations, and/or
12) real time and/or computer-recorded GPS services location(s) information, and/or all communications via all devices/technologies, per smart communicating computerized devices-wearables, platforms-programs, and/or
13) smart communicating device(s)/wearables alert(s) and-or notification(s) to ownership(s), and/or entity(s), and/or veterinarian(s), and/or animal professional(s), and/or designate(s), —and/or
14) monitoring of external-to-animal-body, and/or environmental, and/or
15) internal-to-animal-body, and/or other vital life sign(s) impacting, and/or life sustaining, and/or life terminating variable(s), e.g., ambient in-automobile temperature, and/or internal breathing-pulmonary rate, and/or—
16) functions and monitoring(s) readable by a smart computerized-communicating device(s)/wearable(s), and/or
17) painlessly per veterinarian-anesthesia animal body implanted, and/or
18) otherwise, animal-borne-worn microchip readable information,
19) communicated to a smart device(s), computer(s), tablet(s), laptop(s)-phone(s) and/or wearable(s), and/or
20) via chip-sourced direct connection and-or communication to a smart device(s) per 6, 7 and 8 preceding, also 22, 26, 30, FIGS. 6, and/or
21) via medallion 10, 24-signal-processor 3, FIG. 7, 113, FIG. 8, to 12, 14, 16, 18, 20 via 32, FIG. 6—1, 2, 3, 4, 5 and 6, FIG. 7 capabilities and functions, and/or
22) ID microchip, borne, or implanted painlessly via anesthesia and/or
23) Medallion(s) 10, 24, 210-signal-processors(s), affixed to any animal-borne animal, e.g., canine, equine or other ungulates, and/or feline control-safety-restraining device(s)-trapping(s)-tack, and/or
24) computer-stored information is accessed via smart devices, per paragraphs 6, 7 and 8 preceding, via access codes and/or other privacy protocols, with responses to ownership(s)-designate(s) authorized inquiries enabled via all communication/transmission modes, including, yet not limited to, computer, telephony and/or authorized personal operators and/or veterinary and/or other professionals and/or designates and/or entities, and-or . . .

25) via a smart device-microchip-reader and/or items 1 through 25 preceding, and other animal-owner-relevant information including, yet not limited to, archived recorded aid-care-custody-transport authorization(s) to, and/or by, animal-professional(s)-veterinarians-person(s)-entity(s) for Animal Safety System Registered ownerships-designates, per FIGS. 1A, 1B, 1C, 1D, 1E, 1F, 1G, 1H, 1I, 1J, 2, 3, 4, 5A and 5B, 6, 7 and 8 capabilities and functions.

Lifetime well-being of animals may continue past Pet Parent Stewards' lifetimes, as well as may prove expensive. Such Lifetime well-being may include A) posthumous pet care, B) pooled funds for pet care, C) bond against unlawful actions per system registry included animals/ownership, D) authorized custody-care-location-rescue-reunion-remuneration for Companions per Ownership'-Designates' Companions in unhealthy-unsafe situations, comprehensively identified in the System, and E) Comprehensive computer assembled-aligned-AI-generated equine, feline and/or canine Companion Care, Socialization, Support and Reciprocity.

Discussion: Vital signs monitoring is of internal and/or ambient-environmental animal-life-impacting, sustaining and-or terminating condition(s), e.g., surrounding temperature and-or hurricanes, and/or heart rate, and/or cardiology-cardiograph. Health and safety information communications and/or notices/alerts originate from the singular implanted microchip(s)-device(s), and/or not implanted animal borne/worn devices/medallions/indicia, communicated to ownership(s)-designate(s) and-or archives-monitors-platforms-programs, either directly and/or via an animal worn signal-processor 113, FIG. 8, from monitors/sensors 22, 24, 26, FIGS. 6, and 1, 2, 3, 4, 5, 6, FIG. 7, to designated sending/receiving communicating smart devices-computers-laptops-tablets-phones and/or wearable devices, and/or analytic platforms and programs/interfaced and/or integrated, remote from the animal(s) and-or animal-ownership(s). The Animal-Ownership-ID-Archive and medallion(s) function as a sending-receiving-communicating nexus for persons/entities involved in animal-ownership-designate-relevant health and safety occurrences, and other events, optionally including history, information, instructions, and records.

FIGS. 1 through 7, as disclosed, via halter-hackamore-bridle- and harness-borne comprehensive health and safety functions and services, protects financially and/or emotionally valuable equines-ungulates-canines and felines.

Also, per Pet Parents' Safety System computer-assessed-records, the recorded ownerships and/or their animals bear computer-accessed archived-recorded-identification-indicia, via implant and/or animal borne restraint and control devices/trappings/tack, regardless of halter/bridle/hackamore/harness usage.

Figure reference numerals guide in drawings:

FIG. 1A:10, 40, 41, 42, 43, 44, 45, 46;

FIG. 1B: 10, 24, 40, 41, 42, 45, 46, 50, 51, 52, 53, 58, 160;

FIG. 1C: 70, 71;

FIG. 1D: 70, 71, 81;

FIG. 1E: 60, 62;

FIG. 1F: 61, 63;

FIG. 1G: 64, 65;

FIG. 1H: 10, 41, 42, 44, 47, 50;

FIG. 1I: 10, 41, 42, 44, 80;

FIG. 1J: 10, 40, 41, 42, 43,46, 58, 200, 210;

FIG. 2: 1, 2, 3, 4, 5 and 6;

FIG. 3: 2, 5, 6 and 7;

FIG. 4: 2, 6, 8 and 9;

FIG. 5A and FIG. 5B:10;

FIG. 6: 12, 14, 16, 18, 20, 22, 24, 26, 28, 30, 32, and 34 illustrate, disclose and enable halter/hackamore and bridle and harness smart communicating computer(s)-tablet(s)-laptop(s)-smart phone(s)-wearable(s) archived information, authorizations and real-time comprehensive animal health and safety capabilities and functions between animals-animal owners-stewards-designates-persons-entities for animal comfort, enjoyment, health, safety and well-being, plus ambient conditions, and safe-unsafe-missing animal GPS and otherwise-designated location(s).

Discussion of communications systems: As shown in FIG. 6, external sensors 1 and 3, FIG. 2 and other animal-relevant information from sensor 4, FIG. 2 can be transmitted (wirelessly or hard wired) to the communication devices(s), and the data obtained from the animal's vital life process and signs can then be communicated (remote of the animal) via all communication devices/modes 12, 14, 16, 18, 20, 22, 24, 26, 30, FIG. 6, optionally directly to analytical/monitoring/sensing devices/platform(s)/program(s) interfaced and/or integrated, cloud computing devices and/or smart computing devices, and/or optionally to on-animal-worn-in-situ-device(s) optional treatment(s)/administration(s), FIG. 6, via a halter-hackamore-bridle and/or harness borne devices per instruction(s), with information via signal-booster-transmitter(s) medallion(s) 24 (FIG. 6), optionally aggregating internal-animal-body sensor(s) 30 transmission(s), on-animal-body-external-sensor(s) transmission(s) 4, FIG. 2, and away/distant-from-animal information 1, FIG. 2, (such as, but not limited to, external temperature and/or weather), and/or satellite, drone, airplane, or other device(s)/monitor(s)/sensor(s) and/or communication(s)/transmission(s)/antenna/equipment/transponder(s)/transceiver(s)/frequencies (e.g., microwaves)/modes, including radio frequency identification ("RFID"), IOTA, (an open sourced distributed ledger and cryptocurrency designed for the Internet of Things ("IoT") having a higher scalability than blockchain based distributed ledgers and supporting both value and data transfers), MIOTA ("MegaIOTA")/ID, blockchain/including other archive-accessing-technologies—also including between-straps device(s) 3, FIG. 2. Aggregated animal and/or owner(s) or associate(s) relevant information is optionally further signal processed before being-transmitted, via all communication(s)/transmission(s) devices FIG. 2. Aggregated animal(s) and/or owner(s) and/or associate(s)/designate(s) relevant information, is optionally further signal processed before being transmitted via all communication devices FIG. 6 to smart human communicating/computing electronic devices and/or persons/entities—such as, but not limited to, computer(s), smart communication devices, and wearable smart devices—together as 12, 14, 16, 18, 20 and medallion 24, FIG. 6; (also medallion 10 on halter 40, FIGS. 1A, 1J; medallion 10 on bridle 50, FIG. 1H; and/or medallion 10 on hackamore 80, FIG. 1I, medallions 10 and 210 on harness 200, FIG. 1J) communications and transmissions capabilities, as now-available and developing/perfecting bio-chem and/or other electro/micro/nano-miniaturizations allow dual and/or multiple halter-bridle-harness-hackamore archived and-or real time communicating nexus medallions 10, 24, 210 and/or likewise innovated capabilities-devices-mechanisms-platforms-programs. The animal(s) schematic strap-drawings illustrate strap-halter-hackamore-bridle-harness-attachments 1 away-from-animal, and against-animal 4, FIG. 2, and/or optionally between-straps enclosed units 3; the Comprehensive Halter-Harness-Hackamore-Bridle Health and Safety System also includes legacy veterinarian device(s), monitoring(s), practice(s), procedure(s), treatment(s) and sensor(s), in dynamic union with currently available and innovated micro/nano-bio-chem-tech and other device(s), monitor(s) and sensor(s). External animal monitor(s) sensor(s) and/or device(s) FIG. 2 1, 3 and 4 are operationally configured optimally and optionally, as all FIGs. disclosed, per the maximum comfort and well-being of the animal(s), and-or breed(s), and/or species, as are internal-animal-body-sensor(s) and/or devices FIG. 6/30; Internal-and external-to-animal-body devices, monitors and-or sensors are also operationally, optionally and optimally configured to maximize the overall maximum comfort and lifetime well-being of animal(s), breed(s) and species, according to veterinary science, and technical expertise, instructions and animal comfort protocols.

Information is optionally transmitted to, and monitored by, veterinarians, animal owners-stewards, designated associates, care/custody/identification/location/recovery/transport authorized custodians, professionals and/or programs/persons, including research institutions. It is contemplated that veterinarians, or other qualified professionals, optionally may custom-fit the strapped halter-bridle-harness-hackamore borne sensing, monitoring and communicating halters-bridles-harnesses, and other similar halter/hackamore/bridle/harness animal control and restraint device(s) per FIGS. 1A, 1B, 1C, 1D, 1E, 1F, 1G, 1H, 1I and 1J as herein repeatedly emphasized; the functional components of the Pet Parents enjoyment, health, safety and support systems are operationally and optimally configured optionally per the maximum comfort and well-being of the companion animal(s), breed(s), and species, and generally comfortably configured likewise via manufacturing protocols, and/or specifically comfortably configured via bespoke fittings. The functional components of the enjoyment, health safety and support systems devices, monitors, and/or sensors communicate vital information, data, markers, processes, and signs to smart devices, platforms and/or programs, for communication, enjoyment, location, logging, health and safety purposes, plus reporting, information storage and general animal-relevant comfort and well-being maximization, and owner-steward and-or designate-relevant usage.

The halters, and similar halter-like hackamores, bridle-and-harness health and safety monitoring animal control and restraint devices/trappings/tack, as disclosed are relevant to the health and safety of personally valuable, family-member animal companions, and/or economically valuable trophy animals, e.g., Arabian, breeding, polo, quarter horse and thoroughbred racing and other equines.

However, having primarily directed the foregoing disclosure to trophy equines used in the sports of racing, polo, and/or the breeding of equines, this disclosure is not to be unduly limited by reference to the foregoing extensive disclosure to such animals. It will readily be appreciated by those having ordinary skill in the art, upon reading the foregoing disclosure, that the teachings contained herein can be readily extended to include other animals and/or breeds and/or species without the exercise of invention and that it is not the intent to be limited to application only to equine halters/harnesses/hackamores and bridles, but also has generally applicability to other types of human companion species, such as felines and/or canines and their harnesses, without undue experimentation by the ordinary worker skilled in the art Canines have also acquired multiple roles as socially valuable animals to their owners and breeders, irrespective if they are trained as—show dogs, guard dogs, war/military dogs, emotional support dogs, police dogs, service dogs, rescue dogs, sled dogs, "seeing-eye" dogs, comfort dogs, and-or lifelong-loved companion animals to their wellness overseeing owners-stewards, as "Furry Family Members" of their households; felines also qualify as lifetime-loved emotional comfort, enjoyment, and support companion animals, also as "Full Furry Members of the Family Household."

It is readily within the scope of the appended claims that harnesses (as distinguished from a collar fitting only about the neck of the animal), for these companion animals, e.g., canine and feline, is also within the scope of the invention. The fundamental strap and design FIGS. 1C, 1D, 1E, 1F and 1G, and functions of an animal harness for companion animal control and restraint, is comfortably similar to a halter/harness/hackamore/bridle as used with equines. Harness: The around-the-neck strap(s) FIGS. 1C and 1D, for companion animal canines (shown), and felines (not shown), is also around-the-neck behind-the-ears, as with the equine halter headpiece 42, FIG. 1A; however, with the harness, the behind-the-front-legs/under-the-chest-harness-strap-connects to the animals around-the-neck-harness-strap, connecting to the neck strap on each side of the chest, either connecting directly (not shown)—or per FIG. 1D—(shown) connecting via the short-between-the-shoulders strap, that connects collar-to-around-the-chest strap; the between-the-front-legs-harness-strap FIG. 1C—connects the around-the-neck-harness-strap—to the under-the-chest-harness-strap—including non-strapped harnesses/one piece harnesses, FIG. 1F, strapped tactical-military harness, FIG. 1G, and body-covering harness FIG. 1E. Body-covering harnesses optionally provide animal body warming capabilities, as disclosed below. Examples of such harnesses are used in the environment of sulky-seated drivers, in the environment of the so-called "harness racing," typically between pacers and trotters, in the professional racing environment, in training therefor, and, in general outdoor recreation, when used as an alternative to riding an equine by mounting it. Another example of a body covering for an equine is commonly known as a "horse-blanket." Such body covering harnesses and/or blankets may not only be provided with the various devices/monitors/sensors/sources (DMSS) described above but may also include heating elements to warm the body of the equine.

Per FIGS. 1C, 1D, 1 E, 1F and 1G—generally similar companion animal harness components come in a variety of adaptations. FIGS. 1C, 1D, 1E is an image are illustrations of a canine service dogs 60 (71 also) with a vest harness 62, (63 also) (similar to the equine harness 200, FIG. 1J), FIG. 1F is an image of another canine 61, with a one-piece harness 63; and FIG. 1G displays images of the military/tactical harness 64 on yet another breed of canine 65; FIG. 1G-type harnesses may cover much, most, or in some cases all of the animal body. Vest harnesses cover much of the animal's chest and in some cases, cover some (e.g., most, or all) of the animal's back and body; one-piece harnesses are often made of soft, flexible, rugged, material, optionally with a buckle-strap(s) for a snug fit. Military-type tactical canine harnesses have one neck and one chest strap, vest body coverage, and optionally a second anterior stomach strap: tactical-military/vest FIG. 1G/body covering FIG. 1E/one-piece FIG. 1F harnesses provide the combined-integrated design disclosure premises for "companion animal warming harnesses," that cover much of/all of the animal body, and per Energy/Power Sources (disclosed herein), provide animal-borne-worn heat-retaining materials and/or animal body warming-heating elements-devices fully integrated with body covering harness materials; equine body-warming-heating trappings provide the design premise for disclosing (also energy/power sourced per below) "companion animal warming harness" disclosures are fully inclusive of, and readily and fully extended to include equine body-warming-heating trappings disclosures.

Companion animal harnesses optionally have handles, in addition to front, back, mid and/or multiple clips, for lead/leash attachment . . . the leash optionally alarming/signaling personal smart devices when the leash is disconnected by unauthorized persons . . . animal-kidnappers beware! These companion animal harnesses can also have GPR (or other location sensing devices) and mapping.

Thus, configurations of a companion animal harness-strap-fits across-the-chest, behind the front-legs shoulders; and, the "across-the-chest-strap" may connect via a between-the-front-legs-strap, connecting with an around-the-neck strap, and/or an across-the-shoulders-strap connected by the-between-front-legs-strap to the chest-strap, as shown for example, in FIG. 1G. Harness configurations shown in FIG. 1G and/or 1E, indeed 1F too, may also be incrementally configured to cover much of, and/or most of, and/or all of, the whole animal's body for body warming/heating, and/or other purposes, with per-design adaptations-portals for animal bodily eliminations.

Harnesses, as halters/hackamores/bridles, maximize animal comfort; whereas collars often uncomfortably choke energetic companion animals, and may cause trachea damage and crushing—while some collars are designed to painfully restrain-via-choking; the comfortable design and careful-flexible fit of the harness does not choke nor hurt an animal, rather comforts the animal, as the animal's forward energy is gently distributed about the chest and shoulders, plus balanced via the front legs; thus sled-dogs wear harnesses, fundamentally similar to FIG. 1J, as collars would choke, restricting their harness sled-pulling movement.

Nor is the invention limited to halters/harnesses/hackamores/bridles for equines, as the halter/harness/hackamore/bridle may also be applicable to other animals, such as ungulates, other than equines, as well. Other beasts of burden, such as reindeer, are also economically valuable animals for which this invention is directly applicable.

It should be understood by those skilled in the art that the various DMSS described in use with equines of FIGS. 1A, 1B and 1H, can also be included in any of the various harnesses shown in FIGS. 1C, 1D, 1E, 1F and 1G in analogous fashion.

Energy Power Sources: It is to be understood that device(s) and/or sensor(s) power sources are optionally exterior-to-animal-body batteries; and/or battery powered painlessly-per-anesthesia-surgically implanted and/or swallowed/inserted units; and/or wireless and/or wired electrically charged and/or re-charged external and/or internal-to-animal-body units; and/or motion-generating energy units, e.g., pendulum-generator, etc. units; and/or strap/tack/trappings borne solar-sourced units (not shown); and/or internally self-powered internal-and-or-external-to-animal-body devices, monitors and sensors; external power sources, configured per units 1, 3 and 4, FIG. 2 are optionally affixed on, or enclosed by animal-worn halter-hackamore-bridle-harness-type straps/materials; internal animal body power sources/monitors/devices are painlessly-through-anesthesia-surgically installed and/or inserted/swallowed within the animal per FIG. 6, element 30, also 22, 24, 26.

When batteries are the source of power to the devices/monitor(s)/sensor(s)/source(s) (DMSS), plus self-powered units, communicating-transmitting devices, etc. as disclosed herein, it is preferred to utilize high power-to-weight batteries, or other energy sources. Especially useful are rechargeable secondary batteries, such as lithium-ion batteries and/or other battery and/or other power source technologies. The batteries may be mounted in the devices themselves, such as within the device/monitor/sensor, GPS or other technologies, medallion, transmitting device, etc., or may be wirelessly or wired thereto, as disclosed above, in order to supply the power for the intended function of the sensor(s)/monitor(s), etc. The various battery(ies) may be recharged while on/in or borne by the animal, or remote from the animal. Any suitable recharging apparatus can be used as the power for recharging the rechargeable battery(ies) such as provided by electric energy from the electric grid, solar, wind, or other power source, including self-generating and/or internal power sources, including power generated by movement of the animal. Implants, and on-body borne units, include units that self-generate power sources. Of particular interest is the use of solar power, where the solar power cells are mounted upon the harness/hackamore/bridle/tack, or otherwise animal borne, to maintain the charge of the batteries during sun-daylight conditions, and/or the solar cell source is mounted on the animal's housing or otherwise mounted/sourced. The external sensor 1, in FIGS. 2-3 may also be multiple function devices, including batteries or solar cell powered. Of course, it is within the scope of this disclosure to separate (or combine) multi-function elements into single-function elements and vice-versa. FIG. 2 illustrates unit locations with HHHB-devices having multiple unit location options.

In Summary—internal animal devices, monitors, sensors, sources (DMSS) within the animal(s) body, optionally are painlessly per veterinarian-anesthesia surgically implanted, and/or inserted, and/or swallowed; and internal and/or external body devices/monitors/sensors/sources communicate directly with external computers and/or multiple smart devices/entities/persons as disclosed, optionally personal wearables, and-or via a borne-by-animal-halter-hackamore-bridle-harness communications signal booster per FIG. 6/12, 14, 16, 18, 20, 22, medallion-24, 26, and 30, 210 FIG. 1J (also optionally FIGS. 1A, 1B, 1H, 1I and 1J medallion-10; thus, it is also to be understood that functional system devices, monitors, and sensing/sourcing components: are optionally within the animal(s) body, e.g. internal devices/sensors; on the animal(s) body, e.g. external body devices/sensors; and/or distant from the animal(s) body, optionally e.g. GPS and/or satellite and/or other technologies, and/or drone, and/or airplane, and/or stall and/or shelter mounted monitoring devices and/or sensors above and/or around and/or about the animal(s) for audio monitoring e.g. contagious-coughing, and/or visual-video imaging of behavior(s), and/or other enjoyment, health and safety animal device(s) and/or animal sensor(s) monitoring. Monitored animal(s) enjoyment, health and safety communications and information is logged, analyzed, archived, diagnosed, and/or researched, via programs and platforms, interfaced and/or integrated per privacy protocols, for commercial uses, and/or animal-human-disease control and non-profit activities and research, that includes veterinary, medical and public health benefits, and purposes.

Devices and/or sensors and/or platforms/programs as disclosed herein are designed to serve and advise, alert, analyze, archive, communicate, diagnose, evaluate, film, log, monitor, photograph, record, research, store, video, transmit and/or otherwise communicate and/or process via platforms and programs animal(s) comfort, enjoyment, health, safety and lifelong well-being information for diagnostics, procedures, treatments, science, research and/or via veterinarian, medical and public health institutions; such serves animal health and human health via disease contagion, knowledge, and prevention, also serving principal animal owners and/or allied veterinary and other professionals and designated associates, for commercial and/or nonprofit use.

Intro: The following 53 animal bodily processes and systems, practices and procedures are examples of the animal health conditions and situations the "Internally Self-Correcting Re-Programmable Communicating Health and Safety Computer System" analyzes, assesses and profiles per ailments and diseases, 53 items as disclosed hereinabove (and is not restricted to only bridle-halter-harness-hackamore uses). The system functionally integrates nano-micro-mini computers—with full-sized computers and integrated-cloud-configurations of multiple computers—including smart computerized-communicating devices/portables/wearables; human programmers, and-or programmers-artificial-intelligence, can and may also re-program/re-purpose all of the self-correcting, reprogrammable components of the computer system—from device-monitor-sensor-sources nano-micro-mini-computers, also functionally including smart computerized-communicating devices, also functionally including full sized computers, including cloud aggregations thereof; smaller nano-micro-mini computing devices can and may be included with smaller devices-monitors-sensors-sources as animal implants-ingests-inserts, and-or borne by animals, while larger communicating-computing devices are remote functionally integrated System elements. Conceptually the nano-to-cloud size-sequence of system component-units are correctly conceptualized as a single (and singular) communicating-computing self-correcting and-or re-programmable single system; one focus of the integrated-communicating-unit includes any and all conditions and situations impacting animal health and safety, from-in-body ingested, inserted, implanted devices, monitors, sensors, to likewise body-borne units, to health-safety impacting sources remote from the animal, e.g. NOAA source/deadly hurricanes-health-impact . . . media source/extreme deadly cold-heat-impact . . . NWS source/deadly tornadoes impact . . . therewith self-correcting re-programmable integrated communicating devices-monitors-sensors-sources self-correcting and-or re-programming/re-focusing/re-purposing per granular data-information monitor-sensor-read and/or source-received and-or analyzed/assessed/evaluated optionally communicated to animal-ownership-stewardship, veterinarians, designates.

#1] The computer system includes all communications capabilities/devices, including smart and wearable . . . (singulars can and may be plurals and-or combinations thereof) . . .

#2] . . . via all communication means, media, methods, modes, e.g. signal flags to internet, analog to digital, wire to optical, etc. . . .

#3] . . . to/from all human and/or animal devices-monitors-sensors . . .

#4] . . . and System computers-platforms-processors-programs-servers nano-to-cloud . . .

#5] . . . and human-owners-stewards/designates of animals, and owners-animals' health-centric Computer System maintained archives-registries . . .

#6] . . . via computers, (nanotechnologies) nano/micro/mini/full-sized/integrated-clouds and smart computerized communicating devices, laptops, phones, tablets, wearables, and communication technologies . . .

#7] . . . including (yet not limited to) short range communications-signals and-or long-range communications-signals . . .

#8] . . . short range gathered and range-boosted to long range communications per #2 means as expedient-necessary . . .

#9] . . . communications regarding all life sustaining-threatening-terminating animal health, functions, processes . . .

#10] . . . and animal ailments, diseases, their markers, profiles, symptoms and administrations-procedures-treatments . . .

#11] . . . per animal healthy/unhealthy behaviors, chemistries, indices, markers, profiles, processes, protocols, symptoms and-or other Computer System-included ailment-disease index-markers, per devices-monitors-sensors-capabilities within-System sourced, and-or remotely from System sourced animal health-impacting data-information, e.g. NOAA—hurricanes . . . examples throughout not limiting capabilities, options, responses and treatments . . . sources, please see Introduction, e.g. NOAA etc. . . . ,

#12] . . . systemically inclusive of devices-monitors-sensors in-animal/implant/ingest/insert, and-or on-animal-bridle-collar-garment-halter-harness-hackamore-gear-tack-trappings-borne—and/or from sources via #2 (e.g. archives, media, NOAA, yet not limited thereto) remote from the animal . . .

#13] . . . with the devices-monitors-sensors-sources and associated-communications functionally integrated . . .

#14] . . . on-and-or-in-animal per #12, and-or remote from animal, computers, devices, and/or on/in-animal-body smart-nano-micro-mini to-from-communicating computers-devices-monitors-sensors-sources capabilities . . .

#15] . . . being non-remotely and-or remotely configured and re-configured/programed and-or re-programed/platformed and-or re-platformed/enabled and-or re-enabled/focused and-or re-focused/purposed and-or re-purposed/tasked and-or re-tasked . . .

#16] . . . per the health, safety, ailment, disease, life sustaining/threatening/terminating, and-or other animal functions-impacts-results 36-B

#17] . . . for which devices-monitors-sensors-sources healthful-unhealthful-gradations-thereof data-information is sought . . . e.g. blood-glucose markers and-or sepsis symptoms sought, etc., not blood-limited . . .

#18] . . . either not-remotely and/or remotely—per to-from communications re-programed/re-purposed to kidney functions sought—and/or system-self-corrected per data by monitor-sensor-read—re-programmed to heart-ailment analysis/ailment profile/treatment protocols—heart ailment assessed per life impacting/life threatening sensed-data-indicators, e.g., to cite a likely initial kidney-functions animal-blood-monitoring-purpose—System self-corrected/re-programed re-purposed, per-System-data-read, to heart ailment-condition-treatment analysis—while not by-example-limiting . . .

#19] . . . the device-monitor-sensor-source data-information being reported to a computer-aligned-archive of animal owners/veterinarians/designates and-or individual-single entities—and-or alarm-noticed-per-data-read-assessment to animal-owner-steward/veterinarian/care-principal . . .

#20] . . . System-self-correction per monitor-sensor-data-read—being per computer-program-platform—by self-correction-per-data-read—is configured/re-configured, focused/refocused, purposed/re-purposed—self-corrected-per #20* and/or granular data from kidney-inquiry to heart analysis-assessment—and/or internet-information-per-data-read—and/or medical-veterinary information, and/or . . . and/or . . . per depth-kind of information/supplemental information sought by Registered-System-Included owner-veterinary-care-principal-inquiring-person; *System(s) can and may internally self-correct/self-re-purpose/self-re-program per AI and-or per internal program(s) . . . and-or can and may do likewise per external AI sourced input, and-or per human programmers external input . . .

#21] . . . per the healthy-and-or-not-healthy-ailments-diseases-profiles-indices-markers-symptoms for which vital animal health-status data-information is purposed/re-purposed, sought/re-sought

#22] . . . the System-self-correcting/purposed/re-purposed data-information sought being computer-program-platform-processor-server artificial-intelligence (“AI”) processed/re-processed, programed/re-programed, profiled/re-profiled per vital animal life sustaining/threatening/terminating/and-or other assessments-gradations-processes-purposes of health data-information sensor-sought+read-+self-corrected . . .

#23] . . . and optionally alarmed-noticed-reported to Self-Correcting-In-System-Registered owners-veterinarians-designates, per ailment-disease life-threatening human-programmed/AI assessment

#24] . . . and/or human-to-animal-applied medical-to-veterinary assessments, ailments, conditions, diseases, indices, markers, treatments

#25] . . . and/or programed/re-programed, purposed and/or re-purposed assessments-conditions-profiles via AI solely system-internally of itself

#26] . . . and/or AI therewith human-programmers, and-or by human-programmers-solely-of-themselves

#27] . . . as device-monitor-sensor-data-information-read may discern, e.g. a heart-ailment-profile-inquiry, and re-program/re-purpose the device-monitor-sensor and-or all-of-System-therefor-thereby

#28] . . . therewith self-correcting the initial program/re-program, purpose/re-purpose of kidney-functions-ailments-profiles sought

#29] . . . per AI—and-or per human programmers-programming—assessment per device-monitor-sensor-data-read—as a heart-ailment-profile rather than a kidney ailment profile . . . 36-C

#30] . . . thereby System-self-correction re-purposing System assessment programming, per device-monitor-sensor-source data-information system, thereby self-correcting feedback, to a heart-ailment-profile

#31] . . . multiple System-self-correction outcomes being possible, e.g. kidney and heart ailments

#32] . . . archived-reported granular device-monitor-sensor-source data-information allowing veterinary assessments/re-assessments/confirmations

#33] . . . the proven-on-animals System being applicable to humans as advisory subject to MD-Specialist oversight . . . .

Notes and Discussion: What is this disclosures intention? In summary—a within-System sourced, re-programmable veterinary-medically relevant data-information system—assessing-processing-reading-reporting multi-bio-chem/and/or other-ailment-health-indices-markers; AI, in functional tandem with other programs, monitors/sensors reads-sends-receives health-safety animal data-information—within-System, and/or from input from without System, re-programs/re-purposes device-monitor-sensor+source and System capabilities—per System foci-functions-purposes, per data-information read-received-sent—e.g. re-purposing/re-focusing in-system-self-correcting capabilities—from sensing kidney health-disease markers/profiles . . . to sepsis health-disease markers/profiles . . . to glucose health-disease markers/profiles . . . to heart ailment markers-profiles, per #1 through #33, above, and Introduction, and following notes . . . all in dynamic union with reporting the computer-platform-program-AI-processed granular, and/or meaningfully-assessed-interpreted, monitor-sensor-sourced-read-received data-information, in real time and/or by time-intervals, and/or monitor-sensor-sourced data-based system-self-correction System alarms to System Registered entities; such is reported to the animal owner/veterinarian/designate/System computer-generated-resource-archive; the purposed ailment-disease healthy/not-healthy data-information-ailment-disease-profile, is assessed-evaluated as to normal-vital-life-sustaining and-or threatening and/or terminating assessments, and/or other information-outcomes-purposes . . . communicates the program-platform-artificial-intelligence-processed granular-data-information, and/or meaningfully-program-AI-assessed ailment-disease-indices-markers profiled—and/or ailment re-profiled system-self-corrected results per #1 through #33—to-from communicated to the animal owner/veterinarian/designate. Such is accomplished through nano-micro-mini-device-monitors-sensors implanted-ingested-inserted, and/or on-body-borne components-computers, in dynamic functional union with remote communicating computer units and banks, and smart communicating devices . . . and sources, e.g. please see Introduction: NOAA Thus, we know computers range by size from the (nanotechnologies) nano-micro-mini-implantable-wearable computer to vast computer-complexes, aka “clouds” (not to be confused with the type of clouds known as cumulonimbus). Nano-micro-mini-computers-circuits-chips, also include power-sourced and passive GPS-chips and/or other location technologies for Companion Animals. Therewith, nano-micro-mini . . . the implanted/inserted/ingested programmable/re-programmable monitoring-sensing-device components and/or functions-unified-System . . . and/or animal borne device-monitor-sensor . . . and/or remotely-from-animal sourced device(s) (please see introduction to—NOAA) . . . and/or functional integrations/component combinations thereof. All inclusively entail functionally unified communicating computers-devices, nano-micro-mini-portable-wearable size-ranging to (cloud) archive-and-dynamic-functionally-computerized-communicating-integrations-records . . . and/or various combinations singular and/or plural thereof. Therewith, all system components include integrated elements #1 through #33, and introduction, and following notes as system aspects, capabilities, functions, and/or services . . . with the unique essence of the disclosed system shading toward all-components-elements self-correcting, programmable/re-programmable/re-purposed capabilities . . . in-animal-body, on-animal-body . . . and/or remotely sourced from the animal. Self-correction is caused both from within the system, and caused from without the system, e.g., without=government (NOAA), and/or media, and/or other health-relevant data-information sourced per introduction, such as recent covid communications and mandates, Summary: The programmable/re-programmable dynamic includes implants-to-clouds, and/or in-system and/or out-of-system animal health related data-information-functions-services—#1 through #33+introduction(s) and note(s) . . . also including full ailment-disease assessments-indices-markers-profiles, including self-correcting/re-purposing/re-profiling, per system-external-source-inputs, and/or system-internal per data-information processed-read within the system. Also, per clarification . . . nano-micro-mini-computer-computerized smart to/from-communicating-devices-monitors-sensors-sources, and/or the self-correcting and/or re-programmable/re-purposed system(s) and components described in this application include computerized to/from-communicating computerized portables and/or wearables remote-from-animal, and/or larger-sized remote-from-animal computers and/or functionally integrated computer aggregations and/or clouds.

Figure 9:
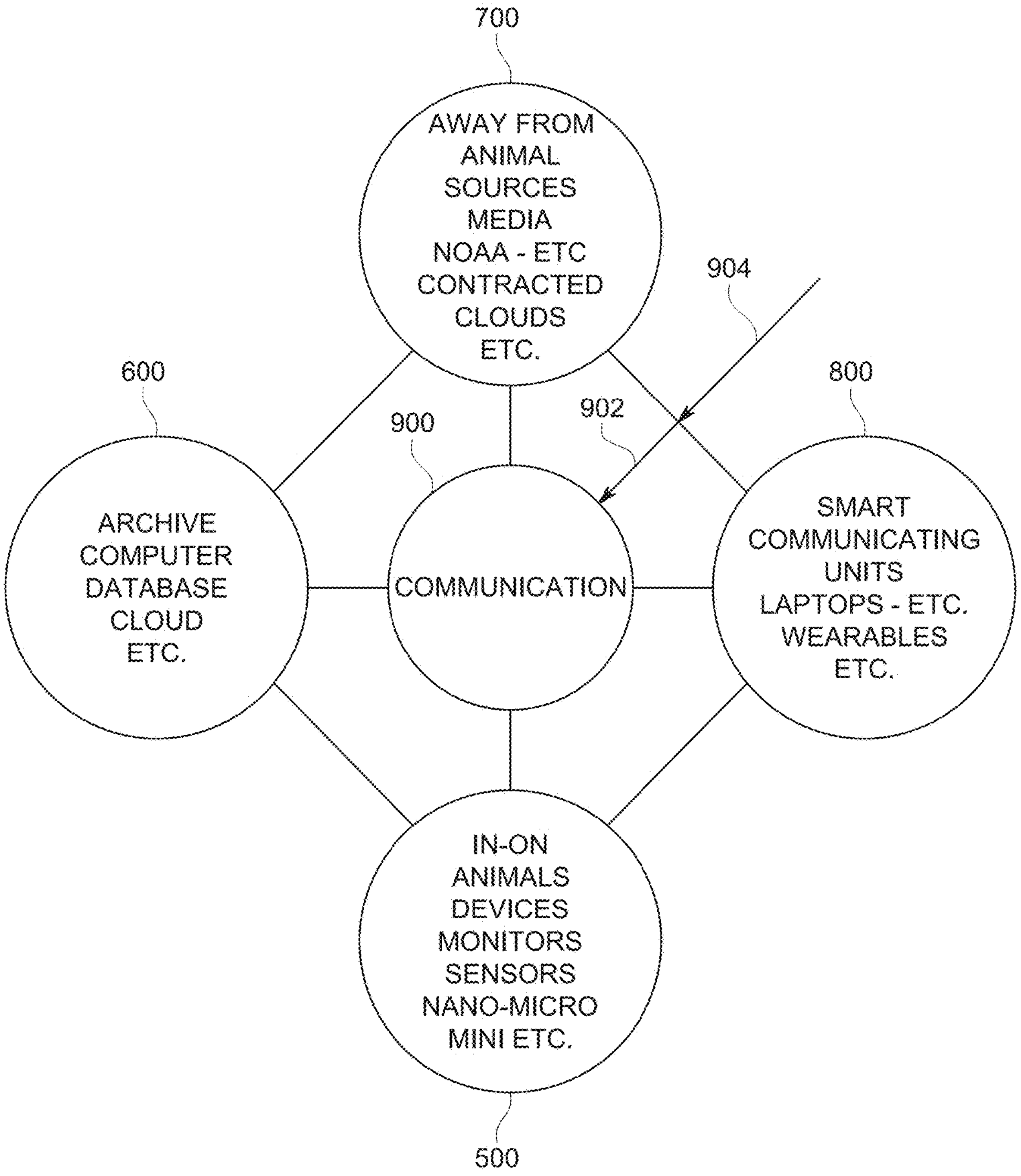
FIG. 9 is a schematic diagram of a Self-Correcting Re-Purposing/Re-Programmable Computer System for use in connection with an animal health and safety system and method according to the present disclosure.

Notes—Re Schematic drawing FIG. 9: All functional elements of The Re-Programmable/Re-Purposed/Re-Focused Computerized-Communicating Animal Health Monitoring, Sensing & Reporting System include to/from communicating computers and/or devices; indeed, an entire functioning computer can and may now be operational within a single-nanotechnology-chip, also micro-and-mini-chips; this physically and/or operationally integrates nano-micro-mini-computer(s) with implanted-inserted-ingested devices-monitors-sensors, as remotely re-programmable/re-purposed-nano-micro-mini sized communicating-computers—the result being, system-combined and functionally-integrated implanted-ingested-inserted devices-monitors-sensors, and/or on/borne by the animal(s), and/or otherwise system deployed and/or functionally integrated—self-correcting/self-focusing re-focusing an initially-intended ailment profile, per-the-actual-read-data-information-profile, per-data-read self-corrected to a non-intended ailment-condition assessment/profile, and-or other outcome-result—in the context of archived system registered animal owners-stewards, veterinarians, designates, and/or human-medical-knowledge applied-to-animals . . . all being examples but not limiting this disclosure thereto.

KEY SENTENCE: The preceding system disclosure is suitable for one, more than one, or a plurality of simultaneous monitoring and sensing capabilities and/or devices for the following animal bodily processes and systems, practices and procedures, while not limited to the following supplemental examples, e.g., 1) microfluidics . . . 2) photo-video image detection techniques . . . 3) sound analytics (coughing—contagion) . . . 4) sweat and salivary sensing . . . 5) wearable technologies . . . 6) nano-biosensors . . . 7) serodiagnosis . . . 8) infectious disease detection . . . 9) communicating devices, monitors and sensors/sources . . . 10) molecular biology diagnostics . . . 11) biochem sensors . . . 12) internal body temperature and/or ambient temperature measurement, logging and notification . . . 13) metabolites monitoring . . . 14) breath-breathing analysis/monitoring . . . 15) implanted, ingested & inserted devices, monitors and sensors . . . 16) medication patches . . . 17) tracking/location programs . . . 18) behavior and movement monitoring . . . 19) pH detection . . . 20) stress detection . . . 21) sound analytics . . . 22) analytes detection . . . 23) virus-pathogen detection . . . 24) contagion detection & prevention—culling diseased animals . . . 25) solar powered health monitors transmitting data to computer-archives . . . 26) ear attached bio-sensing devices measuring body temperature/other signs . . . 27) iontophoretic drug delivery . . . 28) patched and under-skin devices, treatments . . . 29) antibiotic biosensor detection of sub-therapeutic usage causing antibiotic resistance preventing enteric and respiratory disease treatments . . . 30) Maximum Residue Limits biosensors for pharmacologically active antibiotic substances and metabolites . . . 31) integrated data measurements and data acquisition systems via biosensors and monitors producing real-time-rapid health and treatment solutions, and rapid responses to animal-human contagion, including in situ . . . 32) rapid detection of the presence or absence of biomarkers and specific chemicals of life-death importance, e.g. the monitoring of glucose or protein or enzymes or sepsis in the bloodstream . . . 33) bio-nanotechnology and microelectronics make possible the fabrication of transistors smaller than 100 nm & integrating several hundred 100 nm transistors into functional program-platform analytic circuitry via micro-chips . . . 34) microfluidics technology for the rapid detection of analytes . . . 35) thermoplastic and paper based chips have revolutionized disease diagnostic platforms and programs . . . 36) integration of microfluidics and florescent label ensures minimum sample volume and enhancement of sensitivity . . . 37) microfluidics—allows spatial and temporal resolution plus differentiation between non-hybridizing and hybridizing oligomers of DNA . . . 38) surface plasmon resonance—multiple SFR platforms now operational . . . 39) portable SPR device detects antibiotics . . . 40) very accurate screening achieved via digital microfluidics and SPR . . . 41) non-invasive sweat analytics—monitors sodium, potassium, lactate, glucose and skin temperature—blue tooth integrated plus other technologies, communications and analytics . . . 42) diagnosis of diabetic ketoacidosis . . . 43) radio-frequency identification tracking of health related behaviors . . . 44) total quality health management principles substantially benefit animal well-being . . . 45) sweat analytics—pH, CL, Na, glucose, ethanol, lactate, ammonium, electrolytes—sodium, potassium ions, zinc, ions—($Na+$, $CL-$, K=, $NH4+$), cortisol, urea, peptides—neuropeptides & cytokines, calcium . . . 46) pathogen detection—biosensor-based imaging ellipsometry . . . 47) wasting disease detection requires 24 hour audio-video monitoring—cough-sound detected via audio analysis and motion detection . . . 48) temperature—body core & major organs temperature monitored by rectal, vaginal, vascular and digestive-tract monitors and sensors . . . 49) mid-peripheral temperature—monitored by intra-muscular chips . . . 50) peripheral-skin temperature—monitored by skin-embedded micro-chips and through fur-hair skin-contacting multiple sensor probes . . . 51) saliva analytics—as breath and sweat-non-invasive . . . 52) electro-chemical and bio-metric devices, monitors and sensors communicate analytic health data to computer programs and/or platforms integrated and/or interfaced . . . 53) animal-to-human contagion—real-time device, monitor and sensor detection of zoonotic diseases speeds public health contagion and veterinary-medical treatment protocols.

Administration(s) of chemical(s), especially pharmaceuticals, in response to a sensor(s)'/monitor(s)' readings from the animal is also within the scope of this disclosure. The sensor(s)/monitor(s) of the Equine Health and Safety System as herein disclosed can take the readings of the animal's blood sugar, for use in evaluating this condition, which is then addressed by administering insulin. With reference to FIG. 1B, a medicament/pharmaceutical dispensing device 160 may be attached directly to an equine's skin, by locally shaving the hair from the animal (equine, canine, feline, or other animal as disclosed herein), and attaching the dispensing device 160 directly to the shaved portion of the skin of the animal. The medicament/pharmaceutical dispensing device 160, may dispense topical, transdermal, subcutaneous, or intramuscular medicament/pharmaceuticals, such as hormone(s), tranquilizer(s), insulin, or other pharma-treatment substances, in response to a data communication from medallion(s) 10, 24, 210.

As an example, readings indicating that the animal has an abnormal high blood sugar (diabetes) can be used to actuate an insulin device (such as 160, FIG. 1B) attached to the animal.

The actuation can either take the route of sensing/monitoring the animal's blood glucose content, transmitting the readings to a location remote from the animal (e.g., to a designated veterinarian/owner/steward or other designate), who then makes a decision as to whether, and how much, insulin is to be administered to the animal and a communication to the insulin source is actuated to administer the prescribed dose of insulin. As an alternative, where the animal suffers from persistent high blood glucose, the readings from the sensor(s)/monitor(s) of the Health and Safety harness/halters/hackamores/bridle, or other gear, trappings and tack, can be used directly to actuate the administration of insulin to the animal on a one-dose basis; or on a periodic basis, while continuously or intermittently sensing/monitoring the animal's blood sugar. Of course, in both cases, the Animal Health and Safety System can be used to transmit the act of administration to a database/owner(s)/veterinarian(s)/stewards or other designate(s), which is logged and archived into computer-accessed-records, to provide a real-time record of the animal's health; such administrations can and may be undertaken for any, and all, medical/veterinary conditions and/or treatments.

Similarly, the animal's vital life signs, such as cardiac rhythm, cardiograph, cardiology can be sensed/monitored using the Health and Safety System disclosed herein to monitor animal vital life signs, transmit the vital life signs to a location remote from the animal, such as to the designated steward(s)/veterinarian(s), owners(s) or other designates, archive, or for the determination if life-preserving drugs need to be administered in real-time, even though the animal may be disoriented/missing, or in an unsafe location remote from the actual location of the designated steward(s)/veterinarian(s), owners(s) or other designates. Once a determination of the type and dosage of a pharmaceutical to be administered is made, it can be administered directly to the animal by human intervention, i.e., by a local veterinarian; or it can be administered from a local source of the pharmaceutical attached to the body of the animal. Also, similar to the administration of insulin in the previous example, the administration of a cardiac drug can be affected directly on the animal, in response to the sensed/monitored readings, without human intervention, and/or direct-indirect human intervention.

Figure 8:
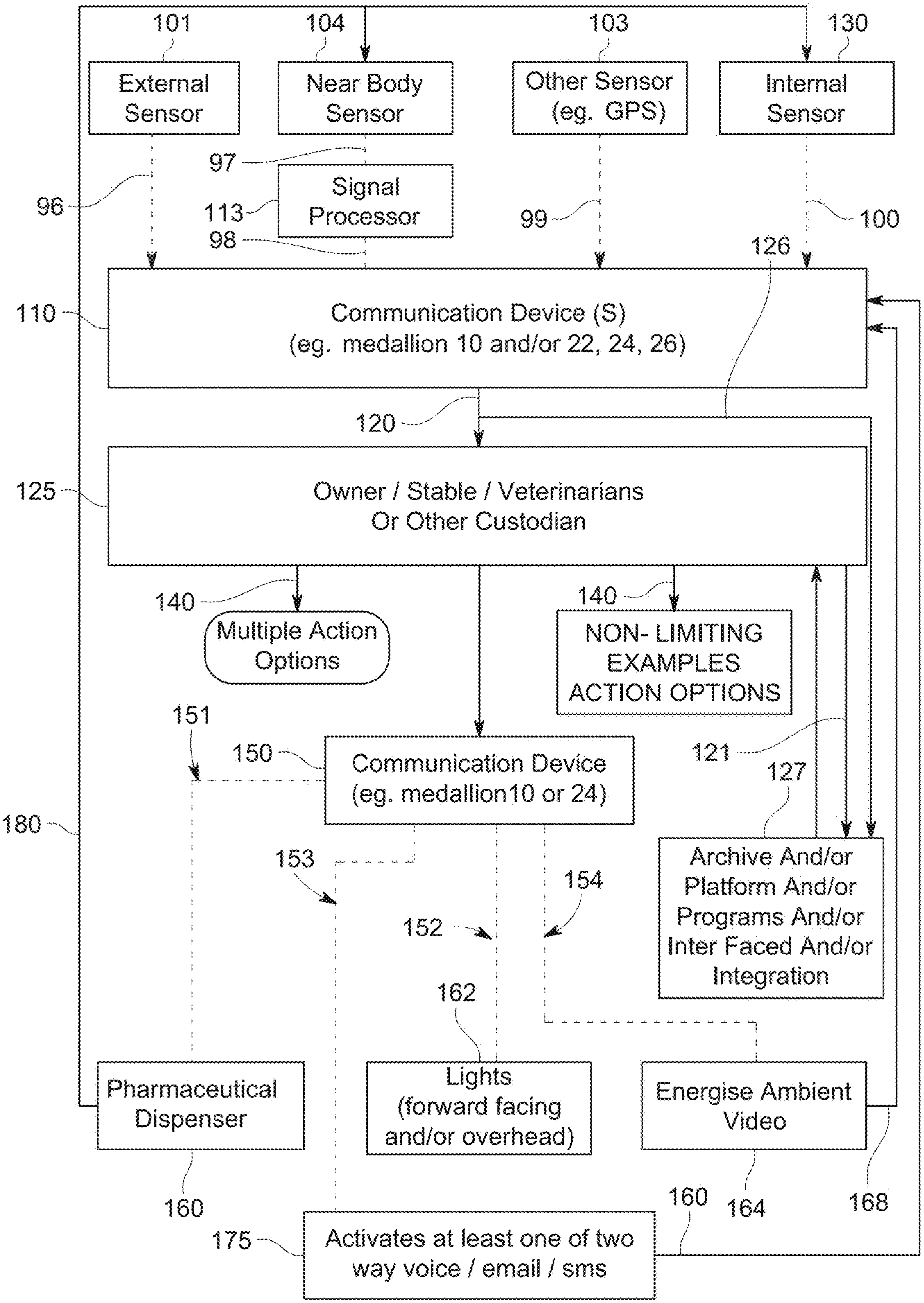
FIG. 8 is illustrative of a flow diagram for implementing the disclosure of the Animal Health and Safety System disclosed herein.

FIG. 8 is illustrative of a flow diagram as a method/process for implementing the disclosure of the Animal Health and Safety System disclosed herein. In the method of FIG. 8, the process begins when at least one of external device/monitor/sensor/source 101, near body device/monitor/sensor/source 104, other sensor 103 (which could be a GPS or other type of technology, sensor) or internal/implanted device/monitor/sensor/source 130 that generates data.

Data can be signal processed before being communicated to communication device 110. For ease of illustration, only one signal processor 113 is shown. However, it is to be understood that more than, or less than, one signal processing can be performed before the data from external device/monitor/sensor/source 101 is communicated to communication device 110, and all, or only some, of the data from near body device/monitor/sensor/source 104 is communicated, via communication link 98; other sensor 103 communicated via communication link 99 and/or internal sensor 130 is communicated via communication link 100. As disclosed herein, communication links 96, 97, 98, 99 and/or 100 can be of any type, such as wireless or wired (including optical, or other technology) links. Communication device 110 (which may be medallion(s) 10, 24, 210 or a separate device, will accept the raw and/or signal processed data and communicate the data to a site remote from the animal via link 120. This remote site could be an owner, a stable or other authorized custodian. It could also be linked directly to an archive 127, and/or interfaced and/or integrated per platform(s) and/or program(s) via communication link 126. The recipient 125 of the communicated data may act, per link 121, on the data, and/or archive the data for later study via communications per link 121. If the recipient 125 of the communicated data wishes to act, the action can be in any of multiple action options 140. For example, aided by the GPS, or other technologies, of other device/monitor/sensor/source 103, the owner/veterinarian or other authorized custodian could be guided to the location of the animal. Alternatively, the action of recipient 125 could take the form of a further communication via communication link 140 to the communication device 150, which could be, but is not necessarily required to be the medallion 10, 24, 210. Such action of recipient 125 could be to enable a pharmaceutical dispenser 160 on the animal to dispense medicament to the animal, or other intervention-procedure-treatment. In such a case, new data, in response to the dispensing, may occur via communication link 180, which new data will then be generated by at least one of near body devices/monitor/sensors/source 104 or internal device/monitor/sensor/source 130. Alternatively, or simultaneous with energization of the pharmaceutical dispenser 160, other functions of the animal health and safety system could be enabled, such as lights 162, video 164 and/or activation of two-way voice/email/SMS/other technologies 170 via communication links 152, 154 and 153, respectively, or other communication systems.

The FIG. 9—System comprises a communications network 900, which can be utilized to re-purpose into a self-correcting, re-programmable computer system and method for optionally organizing a pet-rescue; and/or optionally FIG. 9 re-purposes a (human) veterinarian's kidney-inquiry to a heart-ailment-profile; and optionally further FIG. 9 re-purposes "interests-and-orientations registrant simpatico profiles" per a 99 Item (Optional) Questionnaire . . . via 700 contractual access to "big-data-sources", social-media, etc.

The FIG. 9 system and method 500 relies upon in and/or on animal devices, monitors, sensors which (devices/monitors/sensors) can be of nano-micro-mini configuration. An archive 600 (FIG. 9) can include not only the archive but a computer, database, cloud or other platform, hardware, firmware and combinations thereof to provide real time medical information on an animal, including medical history, images, medications, procedures and other animal specific information. FIG. 9, element 700 includes away from animal sensors, such as sources, media, NOAA and other government or privately sourced information on the environment, etc., including contracted cloud-sourced information. FIG. 9, element 800 comprises smart-communicating units/devices, such as smartphones, laptops, wearables, etc. Each of 500, 600, 700 and 800 can optionally be in communication with each other, but are all in communication with communications network 900 to achieve the goal of a repurposing, self-correcting, re-programmable system and method for animals.

Introduction and Discussion: Animal bodily processes and systems, and (human) veterinary practices and procedures, are the animal health conditions and situations in which the FIG. 9—system and method analyzes, assesses and profiles per ailments and diseases/indices and markers, (and is inclusive of, yet not restricted to, only bridle-collar-halter-harness-hackamore uses, including all forms of animal borne tack and trappings, bespoke fittings, and/or manufactured-multiple-same-design uses-productions). The FIG. 9 system functionally integrates nano-micro-mini-computers—with full-sized computers and integrated-cloud-configurations of multiple computers—including smart computerized-to-from-communicating devices/portables/wearables.

The FIG. 9 system, of itself, per internally initiated purposing/multi-re-purposing, re-focusing may be achieved solely by human programmers . . . but optionally, can and may re-purpose/re-program the self-correcting, re-programmable components of the FIG. 9 system—from device-monitor-sensor-sources (hereinafter "DMSS") comprising nano-micro-mini-computers, borne and-or implanted-ingested-inserted . . . in-animal and/or externally-borne-by-animal and/or remotely-sourced from animal . . . functionally including smart computerized-to/from communicating devices . . . to functionally including full sized computers/cloud aggregations thereof, operated by Artificial Intelligence (AI) which can perform (human) veterinarian diagnosis and treatment, but at a very high rate of speed utilizing the data obtained from DMSS in either FIG. 9 system 600 computer(s) cloud(s), and/or remote-from-system 700 contractual computer(s)/cloud(s).

System elements can include Two types . . . #1=living and #2=human made. Living systems, genetically based, self-modifying per genetic-change per environment, see generally, Darwin; human-made=basic model, home thermostat-heating system, self-correcting condition=temperature=feedback loop self-corrects, maintaining temperature-range.

System Self-Correction: The human-made systems can self-correct as noted above . . . but the kidney-to-heart-ailment example pivoted=re-purposed=self-corrected per DMS-data from the (human) veterinarian's kidney-ailment-inquiry . . . to the correct heart-ailment assessment, per DMS-system-data-read . . . the purpose of the system being correct/confirm (human) veterinary readings of DMS-data per maintaining-sustaining animal health.

Smaller nano-micro-mini computing devices can and may be included with smaller devices-monitors-sensors-sources, as animal implants-ingests-inserts, as noted, and-or borne by animals, while larger to-from-communicating-computing devices are more remote, functionally integrated FIG. 9—System elements per 900 FIG. 9—System integrating to-from communications. Conceptually the nano-to-cloud size-sequence of System component(s)-unit(s) are correctly conceptualized as a single (and singular) sui generis communicating-computing, purposed/internally initiated/multi-re-purposed/self-correcting/System-self re-purposing/re-programming, and-or per human purposing/multi-repurposing/programming/re-programming functionally-per-900-to-from-communications integrated-unitary single and singular FIG. 9—System, (also reprogramming/reprogrammable/reprograms).

The purpose of the integrated-communicating system/method of FIG. 9 is analyzing and assessing health and safety conditions/situations data-information impacting animal health and safety . . . from-in-body ingested-inserted-implanted devices-monitors-sensors . . . to likewise body-borne devices . . . to health-safety impacting sources remote from the animal . . . (together "DMSS") . . . e.g. source(s)—NOAA sourced/deadly hurricane(s)-Animal-health-safety-impact(s), and-or Commercial Media source(s)/extreme deadly cold-heat-impact(s) . . . together device(s)-monitor(s)-sensor(s)-source(s)="DMSS" as a key FIG. 9—System-data-information-driving functionality. Per FIG. 9—System-unitary-functionality . . . purposed for animal-health-and-safety . . . DMSS-data-information also re-purposes/re-programs per location-relevant NOAA hurricane information, urgently-optionally advising Animal Owners-Stewards smart-communicating-units of deadly hurricane, other health-safety dangers, so Animal Owner health-and-safety interventions can-may-are undertaken; in recent USA hurricanes, thousands of Animals died. Likewise for Commercial Media DMS-S=Sourced extreme heat forecast-interventions, saving hundreds of Animals from too-hot weather/cabs/cars/stables, etc.

Following is a discussion of DMSS-driven System-self-initiated re-purposing from kidney to heart analytics, also discussion of lethally-hot-truck-cab System-self-initiated animal-rescue.

Subsequently to such analyzing/assessing, registered animal owners/custodians/designates are system-advised of those animal breeds and/or animal body types and/or medically predisposed animals that are prone to heat-deaths, e.g. the French Bulldog breed, which has a short snout and a small-diameter trachea; in hot weather, canines cool their bodies by breathing, mostly because they have no sweat (feet only) glands. Thus, we see dogs-when-hot panting, with open mouths and extended (cooling) tongues . . . the canine month-tongue-breathing-lungs comprising functionality somewhat analogous to an auto-radiator.

Consider the following case history—On a 100+F degree day, though shaded and watered, our hot-outside-back-yard French Bulldog, overheated and even though it was urgently brought to a veterinarian clinic once discovered to be overheated and unconscious . . . could pass away . . . a companion dog so very-lifetime-loved, whereby the bereaved owner could suffer debilitating depression for the loss, a death that would have been prevented by timely intervention in removing the French Bulldog from the hot environment. Such companions truly are Our Furry Family Members, and indeed the Other Family Doctor is the Family Veterinarian. In such a situation, the system and method of FIG. 9, implemented and/or aided by artificial intelligence ("AI") could, upon receipt of away from animal sources/analyzing 700 indicating an extreme heat environment, comb the archive 600 to locate other animals in the archive/database of registered at risk animals by breed and/or medical history and/or other predisposition to an extreme heat environment, identified from within the archive/database of registered animals, whereby an alert can be sent to the owner/custodian/designate of a single/some/all at-risk animals via 800, FIG. 9, to advise of timely intervention by the owner/custodian/designate to avoid the unnecessary succumbing of the animal(s) to an extreme heat environment.

The FIG. 9 system and method is driven by analyzing-assessing data-information sets; the first set, registered animal bodily functions data and/or information, is sourced from analyzing-assessing-perfecting and/or refining on-and/or-in-and/or-about-and/or-distant-from animal health and safety granular device-monitor-sensor-source(s) (DMSS) provided data/information, e.g. sources/NOAA/Commercial Media Weather Forecasts. The second dataset is comprised of information, and is optionally, including internet/big-data/other (out of FIG. 9=700 contractual system sources), also including, per the 99-item-interest-alignment-optional-questionnaire, experience-interests and/or-orientation(s)/other-information . . . regarding animal owner/stewards/designates backgrounds. The third data-information set is comprised of owners/stewards/designates care and/or custody needs for their registered animals, from animal-care-providers and/or reciprocal-animal-care, for fee, reimbursement, reciprocal, and/or animal-love-volunteer(s). A fourth data-information set includes animal-care-providers, therewith including animal care and/or custody providers background info and/or other information. A fifth data-information set provides registered animal(s) profiles, including animals' care-health-safety & ID-security needs and information . . . not limited to canines, equines and/or felines.

Registered animal(s) bodily functions data-information . . . the first data-information-set . . . is optionally real-time analytically assessed and/or-optionally archived per life-impacting and/or life-sustaining and/or life-terminating assessments-analytics/potential outcomes, and/or animal health and safety gradations thereof, such health-conditions optionally noticed to owners/stewards/custodians/principal-designates. The FIG. 9 system and method serves animal needs and owner health and safety animal-care-assistance-and-support-needs, benefitting the nature and scope of beneficial human-animal-care-support-and assistance outcomes, and animal health and safety outcomes.

Aspects of The FIG. 9 System and Method: Would Corgi Dog Owner "A" appreciate knowing Corgi Dog Owner "B" lives close by, e.g., 2 blocks away . . . likely yes, optionally . . . and that per their (optional) shared Bonded Animal Registry's "99 Item Questionnaire" . . . that purposes and re-purposes via various 600 System and/or out-of-system 700 contractual sources . . . perfecting and aligning owner(s)/animal(s) registrants' animal-care-needs, interests, orientations, and/or life-styles . . . including reciprocally boarding & walking Corgi "B" when B's Owner travels, likewise for Corgi "A". Thus, . . . an intro-glimpse into "System-Simpatico-Care-And-Interests-Alignments"; the purposing/re-purposing bonded animal registry Archive "A" & "B" Corgi Owners (optionally) share, and all registered-bonded-animals-owners/stewards/custodians/designates (optionally) share, sourced from many sources, with privacy protocols . . . System-self-initiates, and/or per human programming, aligns registrants interests, orientations, etc.

The outcome result=purposed and/or re-purposed beneficial refinement of both owner/stewards/custodians/designates and their animals Care-ful enjoyments and interests. Two questions introduce "simpatico"; first, are A & B's Corgis better walked, better cared for, better socialized . . . happier! . . . together in A's or B's home v. mostly alone in boarding cages, when owners A & B travel? Secondly, are owners A & B better-health-walked, better-mental-health-socialized . . . big city safer! . . . happier! . . . walking and-or caring for their A & B Corgis, knowing B is in-a-home, likewise reciprocally for when owner A is traveling?

All data on Pets proffers . . . people with Pets, most often canines & felines, equines too, are physically and mentally healthier; yet Pets also entail many duties and tasks, with the joys. FIG. 9's Bonded Care-ful Owner-Stewards & Animals Registry supports both the Animal Owners Care-ful Health and Safety Animal-care-assistance-needs . . . and . . . likewise for their Bonded-Registered Furry-Family Household Members health and safety care needs.

Bonds are often to assure that the pet-to-vet protocols . . . when a lost pet is brought to any veterinary office by a rewarded rescuer . . . is fully paid for "palliative care", as in relieve suffering, stabilize, and await instructions from the owner [=no new Pet-hips Registry-authorized, unless signed-off by the owner].

Often palliative care will cost between $1000 and $2000, baring Beverly Hills pricing, depending on the palliative care. The rescued pet requires a life-sustaining outcome and owner reunion; posted and/or typical area-pricing prevents price-looting, the condition of the pet's injuries governs the palliative care cost; likely, most rescuer-brought pet-to-vet animals are thirsty, hungry and in need of a bath . . . healthy too.

As Owner-Registrants of Pets, upon Registration, are required to provide two credit cards, one as back-up, assuring Registry-authorized as-needed palliative care, for pet-to-vet delivered strayed-away Pets . . . plus a bond . . . the no-pay-risk to the Veterinarian is minimal, and typically also-assured by the Registry Principals . . . as the pet-to-vet reputation is for perfect, timely pay-out of money.

Purposing—Re-Purposing(s)—Introduction and Discussion: Please consider the veterinarian; a lethargic Companion Animal is brought to the Clinic. The veterinarian suspects kidney disease from legacy experience, and non-painfully per anesthesia, surgically [per FIG. 9—500] inserts into the animal a nano-micro-mini-technology communicating-computerized-device-monitor-sensor that monitors-senses-reads and receives-transmits kidney/biological-chemical-physiological-bodily organ functions and indices . . . including likewise for heart-blood-circulatory health and ailment patterns and profiles, including likewise for ocular, neural, brain, pulmonary, and-or other organ(s)/bodily functions/processes/healthy and non-healthy analyses/data/ailment-disease-profiles, likewise for digestive and reproductive functions, likewise for muscular and skeletal functions including attachments, including skin-fur-hair, per 53 (e.g. not-limiting) iterated analyses and assessments, also including other bodily functions, for potential and actual life-sustaining, life-threatening and life-terminating outcomes and gradations thereof.

FIG. 9—500—implanted-inserted-ingested devices, also on-animal devices, also remotely sourced . . . analytically assessing monitoring, sensing, receiving-transmitting animal life sustaining-threatening-terminating potential and/or actual outcomes; transmitted to 600 archive-computer-cloud* database, if short-range signal via transmission booster 900, transmissions via 900, otherwise directly transmitted to 600 [*generally disclosed—singles can-may be plurals and/or combinations thereof]—DMSS data-information to/from-transmissions optionally-to-800-devices reported real-time purposed/re-purposed/programmed/re-programmed device-monitored-sensed-sourced by 600.

FIG. 9—600—archive-computer-cloud per purpose/re-purposed program analytically assesses DMSS granular data-information-readings and-or assessed information—optionally per veterinarian and/or optionally per Owner Instructions transmits data and/or assessments to 800 veterinarian and/or 800 owner per life-sustaining-threatening-terminating actual-potential health-safety-assessment(s)-outcome(s).

FIG. 9—600—computer-cloud-system-program analytically assesses kidney data—but finding no kidney ailment analytics—the system spontaneously re-purposes, and initiates profile analytics and other analytic assessments of transmitted data-information . . . newly assessing bodily-data-information, including yet-not-limited-to heart data per ailment profiles and/or other analytic assessments; heart ailment analytics and no kidney ailment analytics are communicated via 900 to 800 owner's and/or 800 veterinarian's smart devices, and optionally real-time archived; veterinarian and/or owner initiate-authorize appropriate veterinary animal health interventions.

FIG. 9—the previous example of spontaneous system re-purposing was veterinarian initiated, purposed for kidney ailment analytics and outcomes, and per 500 transmitted data-information, via 900 transmission-booster, as implant transmissions are typically very short range . . . then FIG. 9—System re-purposed per 600 computer analytics, etc. to other ailment-disease-profiles, e.g. a heart ailment profile . . . and/or re-purposed to another ailment(s)-disease(s)-profile. FIG. 9—900: Conceptually and actually 900 includes FIG. 9 System and Method-integrating-send-receive-communications-capabilities, also-including-DMSS . . . including 500 implant boosted-send-receive-communications . . . including 500 on-animal transmission boosters . . . including 600 computer etc. communications . . . including 800 smart-devices . . . including 700 away-from-animal sourced contractual-computer(s)-cloud(s)-communications, e.g. NOAA hurricane information, Commercial Media weather information; 900 boost-send-receive-communications-capabilities-devices dynamically-operationally integrate the sui generis FIG. 9—System and Method as one operationally-single-singular-unit . . . serving Companion Animal Owners-Stewards and their Furry Family Members' Households, their Other Family Doctor being the Family Veterinarian, and Animal-care-providers . . . 900-boosted-non-boosted send-receive-transmissions-integrating FIG. 9—500/600/700 and 800.

FIG. 9—800 . . . includes to-from-people communicating smart devices; wearables, phones, laptops, portable computers, smart-pads, other smart to-from-communicating devices, per 900 FIG. 9—System integration FIG. 9—700 . . . includes away-from-animal contractual sources; e.g. NOAA hurricane information and alerts, Commercial Media weather information and alerts, and System-serving-contractual-computer(s)-cloud(s); 700 is the FIG. 9—System internet and-or other external-to-FIG. 9—System interface(s), e.g. Social Media, big-data-sources, Apple, Google, etc.

FIG. 9—600 . . . includes FIG. 9—System archived-computer(s)-cloud(s) information and services; Care-ful databases may include the following—all Bonded Patented Registered Owners-Stewards information-per-privacy-protocols, personal-photos-optional, personal videos-optional, and contact information-per-privacy-protocols . . . and Registrants' Animals' descriptive-photo-video-information, identifying retina-DNA-breeding-lineage-optional-information, other-Animal and-or Owner-Registrant information; for-fee/no-fee/reimbursement/reciprocal assistance-persons and experience and evaluation information; for-fee animal care professionals, credentials, experience, evaluation information; location-contact-information per privacy protocols; background-checks-optional-information; Simpatico 99-Item Interests-Orientations-Information-optional; internet, big-data, other sourced simpatico-interests-alignment information-optional-via-contractual-700; Pet-Owner related beneficial offers and specials, e.g., the likes of Purina; other Owner-Animal relevant information; fee structures vary per information-services provided, e.g. (not limiting) DMSS-Veterinary-data-information-archive, etc.

FIG. 9—500 . . . DMSS-data-information as to Animals' life-impacting-sustaining-threatening-terminating outcomes/gradations thereof, and-or human-to-Animal-health-sustaining interventions, Veterinary-Medical-indices-markers-ailment-disease-profiles-summaries . . . in-and-on Animals devices-monitors-sensors-sources [sources, e.g. (not limiting) NOAA, Commercial Media weather information], including inserts-ingests, painless-implants-per-anesthesia, and nano-micro-mini-sized-to-computer-cloud computerized-to-from-communicating units via 900 System and-or to 800 persons, internally-systemically-spontaneously DMSS [500—continued] FIG. 9—System read, per DMSS-data-information, re-read and-or newly read, thereby-therefrom systemically re-purposing-analytics-capable, self-correcting-capable, re-programing capable, per to-from-transmissions 500-600-700-800-via-900-enabled . . . Animal borne, blanket, carried, fitted, garment, used, worn, bridle, collar, lead, halter, harness, hackamore, tack and-or trapping, bespoke and-or manufactured-multiples . . . and-or internally ingested, inserted, and-or painlessly-per-anesthesia-surgically-implanted . . . are included in the 500 discussion and disclosure.

The Sui Generis Single-Unit-Units Integrated Functioning of FIG. 9—500/600/700/800/900, aka How It Works: The smart computerized and-or computer devices-monitors-sensors-sources [DMSS] are enabled-purposed-programed, per analytically-assessing bodily-functions-organs-parts-structures, per ailment-disease-indices-markers-profiles, and-or healthful bodily-organ-processes-indices-markers-profiles, bones being bodily structures, skin, hair/fur, hooves, claws being integumentary body-parts, for canines, equines and felines, the Animal-purposed/re-purposed/multi-re-purposed analytic-health-assessing-foci of the FIG. 9—System and Method. Currently nano-computers and-or computerized-nano-devices, can and may be implanted bodily, and-or Animal borne, and-or assessed per data-information otherwise sourced, (sourced, e.g. NOAA, etc. not-limiting, cited), e.g. per kidney inquiry System-self-re-purposed to heart ailment monitoring-assessment-profile, (e.g. not limiting), and-or other bodily-functions-organs-processes-analytic-assessment-readings, via to-from-communicating-DMSS-driven-health-ailment-assessment-analytics 500, 600, contractually 700, and-or to-from 800 units, communicated per FIG. 9—System 900 integrating-unifying to-from-transmissions, either transmitted directly to archives-computers-clouds 600, to to-from 700 contractual sources, and-or to to-from 800 smart communicating-computer(s)-computerized device(s), per 900 non-boosted-non-enhanced and-or boosted-enhanced to-from-transmissions, per 900 enabled send-receive-transmission capabilities to-from FIG. 9—System components.

Please note: FIG. 9—500/600/700/800 capability-components are each 900 send-receive-communications-transmissions capably-enabled, an important characteristic of the singularly-functioning FIG. 9 System and Method per 900-integrated-dynamic; FIG. 9—System 900 DMSS-data-information communications can and may drive System-self-purposing/self-re-purposing/multi-self-re-purposing per analytic-assessment(s) . . . and-or programming/re-programming/multi-re-programming . . . per human programming input . . . and-or FIG. 9—System and Method self-initiated re-purposed/re-programmed DMSS-driving-data-information input, and-or other sourced input.

Thus all computer(s)-computerized FIG. 9—System and Method functional-components are 900-to-from-communication-and-or-transmission-capable, thus enabling re-purposing, e.g. (not-limiting) kidney-to-heart-ailment-re-purposing/re-programming analytic-assessment-example, re-purposed programming per DMSS-data-information, either human re-purposing-programming and-or FIG. 9—System-internally-self-initiated re-purposing/programming.

Data-information from FIG. 9—500/600/700/800 to-from-communicated-transmitted via 900 . . . sourced from System and Method DMSS . . . can and may be real-time and-or archive analyzed, assessed, ailment profiled, and-or otherwise discerned, per life-sustaining-threatening-terminating likely Registered Animal outcomes and-or gradations thereof . . . with urgent-intervention-needs-results optionally noticed to Owner(s)-Steward(s) and-or Owner-Principal-Designates and-or Veterinarian/veterinary personnel, for Care-ful Database Registered Animals; DMSS sourced fees charged Owners-Stewards may differ per analytics-information-notices-services provided to Registered Animal Owners-Stewards and-or their Animal(s).

Purpose applied—purpose, the cause(s), function(s), goal(s), profile(s), rationale(s) and/or result(s) sought; re-purpose—to alter and/or re-alter seeking an initial analysis, condition, definition, function, goal, intent, orientation, profile, rationale and/or result . . . per conditions, data, discoveries, facts, information and/or situations newly discovered and/or newly encountered . . . resulting in a data-information-driven outcome(s) other than initially sought . . . yet caused by/sourced from the initial purpose(s) . . . re-purposing resulting in a single and/or multiple data-information-based assessment(s)/outcome(s)/result(s). FIG. 9—System purpose and/or re-purposing foci concern DMSS-driven canine, equine, and/or feline ailment-disease analytic assessments per animal-healthful and/or animal-safe outcomes.

Veterinarian summary—Veterinarian purpose of inquiry, confirming kidney-ailment profile per system-provided DMSS-data-information . . . FIG. 9—System analytics discern healthful indices-markers per kidney analytics summing to no ailment-profile . . . System-self-initiates re-purposing, analytically continuing per DMSS-data-information assessments per indices-markers read . . . re-purposes to heart ailment-profile-per-analytic indices-markers read. System self-initiated analytics can-may proceed in re-purposed-mode, performing multi-re-purposed-analytics, seeking ailment-profiles per bodily indices-markers read, per DMSS-data-information System-provided.

Please consider . . . DMSS data-information as systemic-input that may also provide, e.g., cancer-indices-ailment-profiles, and system-initiated ailment profile re-purposing per cancer-inclusive-analytics. Please also consider DMSS units, borne and/or implanted, that provide data-information for the, say, 5, 10, 20 most common canine, equine and/or feline indices-markers summing to ailment-profiles. Such is the . . . capabilities-skill-set-interplay of technologies-and-innovations . . . innovation enabling-expanding re-purposing analytic-capabilities, functions, options, and possibilities . . . and devices-monitors-sensors-sources ("DMSS") tech-advancements-and-innovations now unfolding.

Likewise with the System and Method; anchored in technology . . . per FIGS. 1A-9's—500/600/700/800/900 technologies, both proprietary and acquired . . . functioning together as a single-and-singular sui generis animal health unit and owner supporting Care-ful Registry . . . will likewise be pulled forward in tech-time via the inherent advancement of FIG. 9's 500/600/700/800 & 900-integrated device-monitor-sensor-sourced/DMSS technologies . . . a System that also supports not only animals; the FIG. 9—system and method also supports animals' registered owners/custodian/stewards/designates, in their animal-cares-and-joys tasks.

The FIG. 9—900 send-receive-communications-transmissions can and may re-purpose and/or multi-re-purpose computers-clouds/networks/computerized-devices . . . from tiny 500 nano-computers/computerized devices, animal borne and/or no-pain-per-anesthesia-surgically-implanted and/or inserted-ingested units . . . to 600 full-sized computers and 600-700 cloud-aggregations thereof. Persons-entities 800 computer-computerized communicating-transmitting units can and may also be re-purposed . . . re-seeking ailment profiles for healthful outcomes. Also, other commercial and/or non-profit and/or governmental units, of various characteristics, functions and/or types, can and may be included in FIG. 9—System 700 functions.

Health, Location, Safety and Other Services: GPS Animal location services, and/or other location technologies, e.g. Starlink, etc., can and may, either in a single-functions-combined-FIG. 9 proffered unit . . . and/or per multiple FIG. 9 System 500/600/700/800/900 functions, locations, operations, and/or services-units . . . via multiple units optionally in multiple on-animal and-or away-from-animal locations . . . provide Registered Animals location services-information to Registered Animal Owners-Stewards-Principal-Designates . . . per single-and-or-multiple safe-zones and-or non-safe-zones per Animals . . . real-time safe-unsafe-locations-zones, noticed to, and-or archived for, Owners-Stewards being an option . . . also optionally including ailment and-or health conditions/archiving/monitoring/reporting, /location-tracking, and-or other capabilities and-or services sourced per this disclosure.

Such analytics, functions and services may be combined in single units, and-or multiple on-animal and-or away from-animal(s) units . . . in combination therewith also providing DMSS-sourced health and safety analytics, and/or location, and/or safe-zone(s) analytics and information . . . providing health and safety healthful and/or safe assessments-information, and/or ailments-profiles-analytics-information per DMSS life-sustaining-threatening-terminating animal and/or situational conditions, and gradations thereof; real-time noticing to owners/custodians/stewards/designates of some, partial and/or all services is also a commercial option. Users of locations safe-unsafe-zones/health and safety data-information/other services can and may receive use-differing analytic, data and information combinations and information-data sets, per differing fee structures. commercial combination of . . . identification, health monitoring, and/or location data . . . and/or other capabilities and/or services per this disclosure; can-may be individually, partially and-or in combinations proffered.

Discussion: Device-monitor-sensor can and may be an ingestible and/or an inserted 500 unit, and/or (painlessly per anesthesia by veterinary-professional) a 500 implanted unit; a functionally likewise 500 unit can-may be out-of-body-borne by the animal; 900 data-information is received and/or to/from-900-communicated throughout the FIG. 9 System, to the appropriate nano-to-cloud-computer(s) to be read, as to data-information impacting animal life-sustaining and/or life-threatening and/or life-terminating conditions and/or situations, and gradations thereof . . . and/or other such relevant information. DMSS data-information includes devices, monitors, sensors, sources, e.g. (not-limiting), the deadly animal-implication(s) of a NOAA-sourced-forecasted hurricane is self-evident, as are commercial media sourced warnings of deadly environmental-heat and/or cold conditions for animals. Such threats are FIG. 9—System-900-communicated/optionally noticed and/or optionally urgently noticed, to 800 animal-care-principals via 900-system-integrating send-receive-transmission capabilities.

Less evident are the 500-DMSS functions per a veterinarian implanted monitoring-sensing device, e.g. for kidney functions, sending both raw-data and per-ailment-disease-profiled-assessments via 900, to 800 Smart Units, and/or to 600 archive(s), cloud(s); archived DMSS-data-information is also real-time assessed per life sustaining-threatening-terminating, and/or outcome gradations thereof, and when analytically assessed as urgent, optionally noticed to 800 owners/stewards/principal designate(s) ("OSPD") smart-units via 900 communications-transmissions.

The DMSS-monitor-sensor unit, both via 900 granular-raw-data transmitted, and/or per System 600 ailment-symptomatic-computer-computerized-analytic-assessment-profile(s), (and/or per out-of-System 700 commercial contract(s)/and/or non-profit contract(s)), is purposed-re-purposed/programmed/re-programmed per FIG. 9 System purposed-analytic assessments; per this example, the FIG. 9 System internally analytically-assesses-reads no kidney ailment; the FIG. 9 System, finding no kidney-ailment-indices-profile(s), system-internally re-purpose(s)/re-program(s) DMSS-data-information-indices read/analytically-assessed, and discerns per DMSS-data-information an animal heart ailment . . . and/or the System continues to re-purpose . . . multi-discerning per ailment indices/profiles DMSS data-information, optionally noticed to OSPD per 900, optionally 600 archived for OSPD/veterinarians.

Most Respectfully, Please Note: 900-send-receive-transmission(s) 500/600/800 capabilities, contractually 700 also . . . enable the smallest nano-micro-mini-computer-computerized-device(s), to the largest computer(s)-cloud(s), and/or intermediate device(s)-unit(s) . . . to engage in smart-computer-computerized analytic-assessments, purposing/re-purposing/re-re-purposing, programming, re-programming, multi-re-programming, processing data-information, from DMSS=Sources . . . be they "big-data", and/or internet, and/or archive(s), and/or OSPD, and/or other Registry-sources, etc. The FIG. 9 System and Method computer(s)-computerized-smart-device(s), internally system-self-initiate-purposing/re-purposing/programing/re-programing of assessment-analytics. (It is to be expressly noted, throughout this document, e.g. examples, are not limited thereto, but rather are generally illustrative of the disclosure).

Thus, the all-communicating integrated computerized FIG. 9 system, nano-micro-mini-to-fully-sized-computers and banks/clouds thereof, per programming . . . and/or human-program-intervention(s) . . . self-re-purpose/re-program(s) nano and-or micro-and-or-mini-to-cloud-computer-configuration-purposes, from DMS-to-S=Sources=DMSS. In the veterinary example, implant-system-nano-computer(s) raw-granular-data . . . is re-purposed/re-programmed to heart-ailment assessment-discernment-ailment-disease-profiling. Thus, the FIG. 9 system of itself, initiates/re-purposes/re-programs its analytics . . . from the veterinarian-intended-experienced-(kidney)-ailment-"hypothesis"-purposed-inquiry-assessment . . . to the ailment-assessment per the raw-granular-data-monitor-sensor reads . . . communicating-noticing such via FIG. 9 via 900, optionally to 800 animal-care-principals; also raw-data, per system-ailment-disease-discernment, is optionally archived per FIG. 9—600 computers-computerized-devices.

Please also consider . . . an out-of-animal on-body monitor-sensor borne by the animal; e.g. the borne-sensor real-time detects no life-threatening-terminating condition-situation; all is A-OK per animal-well-being . . . 'tis a cool early morning, a quick errand . . . all A-OK to leave her canine, Ol' Rover, windows down a bit in the pickup-truck-cab . . . in a hurry, nasty pothole, hop over, edge crumbles . . . all A-OK until the canine-owner sprains her ankle . . . is now unable walk . . . cannot quickly return to her truck-cab with dog therein. Her all-well-being A-OK quick-errand-situation . . . is becoming animal-life-threatening-terminating in mere minutes . . . e.g., 'tis Carson City, summer temperatures rising to 100F+; every day, cool mornings quickly turn into hot days.

Our FIG. 9—500 borne dog-collar-harness-sensor(s)-trappings-tack/animal-borne-gear, FIG. 9—System-self-activates and self-re-purposes the All-A-OK-animal-well-being integrated system . . . re-purposed to emergency-life-threatening-potentially-terminating urgency . . . and the system, of-itself via the internet or other communications network, e.g., cloud, reads-smartly-per-location, texting police, sheriff, Animal Control, location-relevant veterinarians, registry-rescue-volunteers (plus other-location-relevant-big-data-options) . . . notifies animal control=life or death dog-in-life-threatening-hot-cab . . . per GPS/Starlink/other location technologies/as the FIG. 9 System knows the dog's location . . . notifies local police and sheriff . . . notifies all in-area-veterinarians . . . and per the System 600 archive-registry, includes all bonded-Care-ful-Registry-rescue-volunteers in-the-relevant-area, next-door, etc. . . . plus FIG. 9—600 area-relevant registry-principal-designates, e.g., OSPD.

The sui generis integrated-operationally-functionally-singular-per-900-communicating-transmitting system [FIG. 9—900] . . . is real-time-now all dynamically 600-computer-re-purposed-rescue-driven/involved-volunteer-tasked-tasking/as the purposed/now-re-purposed A-OK-to-Urgent FIG. 9 integrated computerized communicating system self-accesses-contacts-communicates-focuses-animal-rescue per FIG. 9—registry resources, including internet-sourced-police-sheriff-animal control-texting+big-data-other 700 contractual sources . . . accessing-and-employing all FIG. 9—System capabilities-and/or-resources . . . re-purposed from A-OK-to-emergency capabilities . . . as the system of itself self-purposes/self-re-purposes . . . from A-OK animal well-being-status . . . to life-threatening-potentially-life terminating-emergency notifications-rescue-coordination-mode. The FIG. 9—system is self-driven per DMSS internet information readings . . . the system "knows" per rising-temperature-DMSS Commercial Media 700=source lethally hot-day forecast-sourced data . . . system-received-read-acted-upon, per "reading" weather forecast=emerging weather situation.

The FIG. 9—System (Hypothetical example) 500 DMSS sensor sourced hot-day-information self-initiated and self-organized and communicated a system protected registrant's pet-rescue, per 500, a DMSS animal rescue from death in a fatally hot truck-cab . . . as every summer, and everywhere in hotter U.S. climates, animals die in hot autos, truck cabs too. The happy ending to this exemplary tale . . . is the sheriffs/animal control officer's truck was (fortunately) in Carson City, as the FIG. 9 System self-corrected-re-purposed from A-OK to Urgent . . . internet-communicating/organizing/texting a pet rescue via the local sheriff/police . . . per the hot-cab hot-day life-threatening-to-dog urgent situation . . . and per our tale, the dog was safely in the animal control officers custody, to be reunited with her no-walk-ankle-sprained owner. (Such is our happy hypothetical example; the real occurrence initiating this disclosure, was . . . per a local veterinarian . . . the dog was brought to the veterinarian in an unresponsive per heat-stroke, and despite heroic and expensive efforts . . . died.) Such is a regular summertime-tale, with both happy and sad outcomes; the FIG. 9 System and Method works toward ever more happy outcomes.

Here we comment on rescue-scenario-options. The first is the FIG. 9 System blanketing location-relevant potential rescue-participants; some we have mentioned . . . the likes of police, sheriff, animal control officers, veterinarians, registry rescue volunteers, next-door, etc. The point is . . . some Care-ful person will be near-by . . . officers, sheriff, animal control officers, veterinarian(s), registry rescue volunteers . . . and a hot-cab-dog-death will be intervened . . . plus, a rescue/reunion-reward is offered.

Our other rescue-option is the sprained-ankle-gal mentioned above. So far, our hypothetical example has (rudely) left her out; the hypothetical paramedics now have her at the local Emergency Room . . . and she is also urgently dialing the bonded Registry . . . as she opted for the Dial-n-Discuss-Real-Professional-Human-Fee-Option. In addition to The FIG. 9 location-relevant-blanket-notifications, other animal professionals are now also contacting location-relevant networks, per this option . . . v. tech-automation.

Thus, we note . . . the one-two-three approach . . . #1=FIG. 9 System smart-location-relevant-zip-code-powered-smart-noticing . . . and—#2=Rewarded Rescuers . . . plus #3=FIG. 9 System social-media-and registrant-etc.-smart-targeted-blanketing . . . all together tripling rescue effectiveness. Purposed/re-purposed and/or multi-re-purposed, tasked/re-tasked, programed/system-internally re-programed . . . for computer-computerized-driven DMSS data-information-system-inquiries . . . are sourced from 500 and 600, contractually-from-700-sources, optionally 800-computer-computerized-smart-sources also, via 900-system-integrating-communications-transmissions . . . sourced from integrated system device(s)/monitor(s)/sensor(s)/source(s) (DMSS) capabilities; thus, an implanted nano-micro-mini-computerized device-monitor-sensor reads raw-granular animal-bodily-processes data-information, as well as intermediate-analytic-computer-computerized unit(s) . . . communicating that data, both raw-granular, and/or analytically/ailment-disease-profiled, and/or otherwise analyzed-assessed DMSS data-information . . . throughout 500-600-700-800 capabilities via 900-system-integrating-communications-transmissions . . . throughout the single and singular FIG. 9—system and method; FIG. 9—System-500-600-700-800-900—components are capable of system-initiated re-purposing/re-programming inputs-outputs, driven by FIG. 9—System-read DMSS-data-information, and/or per AI or human-sourced re-purposing/re-programming intervention(s).

Thus the veterinarian, via 500 and-or 600, 700-contractually, for example, can and may input a FIG. 9—system kidney-function-inquiry-indices-profile request . . . and/or via the 500 nano-computer, and-or integrated-interfaced 600 archive(s)-computer(s)-computerized-unit(s), 800 smart-units input optionally too . . . can and may system-self-re-purpose the kidney-profile-system-inquiry, to a heart-ailment-profile, and/or other ailment-disease-indices-profiles per tech-DMSS-capabilities available. Thus, per DMSS-driven-data-information, system-self-re-purposing, per technologies-DMSS-reading-assessing-analyzing-and/or profiling available, and/or other capabilities-innovations-tech-available . . . and/or system-inclusively, yet per out-of-FIG. 9—system contractual-700-computer(s)/cloud analytics . . . can and may discern ailment-disease-profiles other than the 500 nano-computers-to-cloud 600/700 kidney-functions, to heart-ailment analyses/profiles . . . and/or system-re-purpose the 500 nano-computer-to 600/700 accordingly via 900 communication(s); thus, FIG. 9—System DMSS capabilities can and likely may be tech-expanded to discern a multiplicity of bodily analytics-assessments-functions-indices-ailment-disease profiles via ever-more AI-innovation developing ever-more and improved measures and means.

Likewise, via 800 Animal-Care-Principal System inputs and outputs (902, 904) via 900 . . . 800 interventions can and may be optionally received-sent, and interventions/other-instruction(s) provided. Thus, we see the functions of any and all life-based open (living) animal bodily systems feed-back-loops . . . also as system-animal bodily functions, and DMSS data-information inputs and outputs . . . and OSPD Care-ful Registry inputs-outputs . . . thus FIG. 9—System sui generis singularity. Communications unit 900, (FIG. 9) can both receive input, as well as transmitting information to other locations. Thus, 900 may comprise a receiver, and/or transmitter, and/or transceiver. Data from each of 500, 600, 700 and/or 800 can be communicated to 900 via line segment 902. Additionally, other out of system data may be communicated with 900 via line segment 904. Although line segments 902, 904 have arrowheads depicting information transmitted to 900, it should be also expressly understood that 900 can transmit data to other locations. Thus, line segments 902, 904 are illustrative of data being received by, or transmitted from 900.

Communications unit 900 can comprise additional elements, such as a central processing unit, a buffer, non-transitory memory, a time clock capable of time/data stamping of data received by or transmitted from 900, and similar elements to facilitate the receipt by, or transmission from, 900.

The FIG. 9 System is a “closed system” in the sense that it is monitoring-sensing-data-plus-profiles of living (open) systems . . . AKA The bonded-registry for registered-animals, owners/stewards/principal designates, “OSPD”. Thus, the functional-system-clusters . . . 500-600-700-800 dynamically integrated per 900 . . . function in singular union; therewith, the integrated FIG. 9 System, is also characterized by multiple via-900 feedback-loops to each and every function-cluster . . . per the sui generis FIG. 9—900 dynamic system-integration.

A note on Systems . . . two types=Living Genetically Based Self-Advancing-Adapting-Surviving (see Darwin) aka “Open Systems” . . . and . . . Human-Dependent Created Systems aka “Closed Systems”, the latter being fully dependent on human creation and maintenance, from human-sourced electrical supply-grid-input-linemen to human-built-maintained-electrically-supplied cloud-computers-sheltering-structures. The most advanced cloud-computer-system is still . . . non-operational . . . without an input-electrical-grid, linemen-built-and-maintained, human-engineers-designed! Whether complex systems self-re-purposing-pivots, and/or programed feedback-loop self-correction(s)/re-purposing(s) e.g., kidney-to-heart-ailment per DMSS . . . to the simple thermostat-controlled residence heating system feedback-loop pivot-re-purposing-heat-on-or-off self-correcting temperature . . . Closed Systems are human creations and require human-intervention-maintenance-input . . . for output.

Thus, the most sophisticated self-correcting, e.g., re-purposing-from-kidney-error-to-heart-truth-analytics/self-perfecting system is the result of human programming, and requires human maintenance, e.g. energy inputs (AKA thermo-dynamic off-sets) to maintain system-functionality. Thus, the FIG. 9 system too is a Closed System, human-created, human-maintained-sustained, and/or human-programmed to e.g., re-purpose health-error to health-truth analytically . . . self-correcting erroneous kidney disease to the correct heart-ailment-profile . . . purposed, multi-correcting-re-purposed; key purposing/re-purposing programming/re-programming/re-re-purposed System-9 self-correction-pivots, e.g. kidney-ailment-hypothesis to heart-ailment-data-facts-information-driven-self-correction.

In an all-ailment-technology-capable-analyzing-theoretical-realm . . . the FIG. 9—System can-may process all-DMSS-data-information form any animal . . . and/or human . . . and per re-purposing-self-correcting-pivots . . . know all truthful=accurate conditions of all bodily processes per all animal-veterinary and-or all human-medical knowledge . . . theoretically.

Here we re-introduce the Steve Jobs technological-future-anchor . . . as technology-self-innovates per human input, the mini-micro-to-nano capabilities of technology can/may/will increasingly reach an ever-wider-range of bodily processes analytically, per healthy and/or per ailment assessments. The time will arrive, tech-sooner than we expect, when love-bonded-and-or-financially-valuable canines, equines and felines, or other animals, per mini-micro-nano-implants-devices, will have vital bodily processes continually monitored, with the results of such devices-monitorings-sensorings, sources too, (DMSS), continuously computer-cloud ailment screened, with key results continuously communicated-transmitted to human veterinary and/or medically responsible OSPD . . . and Medina Spirit would not have died on the Santa Anita Racetrack: Amen.

Our discussions/disclosures, to this point, have been purpose-driven by DMSS data-information. Let us now hop to the FIG. 9 Second Data Set, purposed as "the Owner-Steward Care-ful 99-Items-Driven Questionnaire-Databank." Pet-care entails many tasks and much work, in addition to the joys of Little-People-In-Fur-Coats-Companionship, aka Furry Family Members . . . the Other Family Doctor being the household veterinarian. Pet owners tend toward being a bit stand-off-ish, their pet being pet owners (sorta) out-front alter-ego. A conceptual window into understanding here . . . getting it . . . likely proceeds from a tail . . . um tale, below.

We may find ourselves out for a walk, living in a Big City neighborhood; living-close-by-neighbors walk by . . . scarcely a word is spoken. Indeed, initiating a conversation is more often not well received. Now, the same neighborhood, the same silent neighbors . . . yet we are walking our dog; the dogs engage, as do their owners likewise, the conversation likely elongating to include other pets . . . cats and their "personalities", likewise with dog's "personalities". When encountered again . . . again engagement and conversation. The point is obvious . . . pet owners conversationally pivot for other pet owners; yet indeed, the owner on the other end of the leash is somewhat solitary . . . thus the Companion Animal; got it!

Create a pet-based comfortable format for edging-and-inching-out of a tendency toward solitary . . . with/for/by/per The Pet! . . . and solitary is edged out by . . . Pet-powered Care-ful relationships . . . amiability . . . camaraderie . . . companionship . . . fellowship . . . friendliness . . . friendship . . . neighborliness . . . dare we say . . . more happiness . . . edging-inching-out more solitude? One gets the point . . . and should Ms. Corgi-owner "A" likewise, and both also, find dog-walking with Mr. Corgi-Owner "B" "simpatico" . . . nature will take its course . . . and the comfortable-formats-tasks are now initiated. [While not as "hard" as tech-stuff . . . happiness beats "hard-tech-nano-type-stuff" . . . got it!]

Let us approach pet care from another angle . . . pets are a lot-of-work . . . and a lot of responsibility; we have all heard . . . "gotta get home for Rover's walk" (bodily-functions). So, we edge into edging out solitary via a comfortable format for pet care assistance . . . never mentioning . . . more pet owner happiness exchanged for less solitariness . . . this purpose silently powering this 600 database-portion of The FIG. 9—System and Method Care-ful Registry.

The second 600 database set is best summarized as simpatico alignments purposed . . . common interests initially alignment-driven by the 99 Item Questionnaire . . . supplemented by 700 contractual social media/internet interests-alignments, also big-data, and other 700 out-of-system archives-databases-clouds-sources, yet contractually-functionally-operationally in the FIG. 9—system, per privacy-protocols and policies; participation is optional. How interests-orientations-sentiments are aligned and perfected for registry OSPD . . . system techself-aligns interests-orientations per 700-contractual databases access . . . as system-tech likewise collects information to conduct hot-truck-cab system-initiated pet-rescues likewise . . . same searching-reading-Registrant-relevant-information-collecting and interests-and-orientations-alignments.

The third 600 database set . . . 700 contractually supplemented, is purposed for the care and reciprocity-assistance-needs with registered animal owners. As noted, pets are great joys, and by all indices pet owners are generally healthier mentally and physically . . . yet pets entail much expense, care, and responsibility. Who will assist with pet care chores and tasks when infirmed, when recovering from a new knee replacement and/or other surgery . . . likewise recovering from a mountain-biking-crash? And when Mr. Corgi "B" is away on business, likewise Ms. Corgi "A" . . . 'tis likely cage-care mostly at dog-boarding, without Care-ful reciprocity; Corgis A and B reciprocally together, dogs-and-Owner, in A or B's home v. that cage! . . . doggy-and-human socializing, walking, ball-chasing, etc., at home in a home . . . v. that cage!. When traveling, for business and/or for pleasure, animal owner's concern for one's companion animal's care is a significant worry-stress for animal owners . . . and most animal owners cannot afford expensive in-hone-pet-sitters, and-or expensive pet-resorts; thus, the bonded Care-ful-database-resource is both the high-quality pet-care provider, and the high-quality yet low-cost pet-care provider. [Background-checks are an option, for Care-ful reciprocity care, and/or other pet-care providers . . . either for-fee and-or no-fee/reimbursement(s)/other fee/no-fee-options.]

The fourth 600 database-set . . . perfectly complements database-set-three, by supplying non-registrant care-providers . . . being purposed for the animal care needs of registered OSPD both for-fee-animal-care-professionals, reciprocals, reimbursements, volunteers, and/or other care providers. Credentials are itemized, 700 sources are system-technology-reviewed as relevant, and evaluations are provided by registered owners of care described.

The fifth 600 database-set is purposed for registered animals' photos, videos, retina-genetic-DNA-breeding, other identification(s), health profiles, and/or archived DMSS data-information, plus special care needs, and other relevant registered animal information. Data-information sets are purpose-programmed, and perfected/refined, including animal archives and/or profiles.

DMSS-Safe Zone-GPS-Starlink-other location technologies: The FIG. 9 system and method combines DMSS-Safe Zone-GPS/other-location-technologies, in a single unit . . . FIG. 9 system purposed/re-purposed/re-programmable, internally-self-correcting-refining-perfecting-re-purposing, e.g., kidney to heart re-purposed-pivot . . . and/or per external-input re-purposing-re-programmable unit-units . . . implanted and/or animal-out-of-body/on-body-borne . . . and-or DMS-S=externally-sourced information . . . implanted and/or on-animal-borne-device-unit- . . . per purposing/re-purposing(s)/re-programming(s) protocols. Thus, the units . . . DMSS-monitors animal health and safety . . . and/or tracks-records-and/or archives animal location(s) . . . and/or real-time reports-archives safe-zone-presence(es)-and/or exit(s) . . . and/or identifies the animal per system options, DNA, etc., DMSS health and safety—safe-zone/location/identification/for canine(s)/equine(s)/feline(s)/other animals=commercially very valuable.

Safe Zone Discussion: The Animal Health and Safety monitoring System and Method self-senses the animal, likely a canine . . . equines too . . . that have strayed from within its GPS defined safe-zone; the System quickly-repurposes, internally initiating text, email, and other noticing . . . that Ol' Rover has slipped out of his backyard, to relevant neighborhood parties, also Care-ful Registrants and Registrant Volunteer Rescuers, Nextdoor, Animal Control Officers, and other location-relevant Pet-caring individuals-organizations-volunteers . . . location-otherwise-relevant contacts that the self-re-purposing-System has researched and for-action-archived, location-relevant to Rover's Care-ful Registered Pet Parents. The FIG. 9—System's reunion-reward is announced, and communicated for Rover's return-reunion to the Owner, including pet-to-vet payment to any veterinarian for holding Rover 'till owner-reunion occurs, plus palliative care as necessary; all veterinarians in the relevant zip-code-areas are also System-notified, per the Systems purposed, that is self-collected-screened Pet-caring relevant contact resources . . . plus noticing via 900 all location-relevant Care-ful Registered Pet Parents 800 smart-communicating-devices, and other System-self-generated relevant contacts and resources . . . as well as the Pet Parent(s), of course.

The result—rapid system FIG. 9 initiated-re-purposing, driven by out-of-safe-zone DMSS-information, contacting area-relevant Pet-caring entities, in-the-search for subject-canine . . . equine and other animals too, likely in a more rural setting. Ol' Rover is found, say via Nextdoor, in the 'hood by a Volunteer Registry Rescuer . . . and taken per pet-to-vet to an area-relevant veterinary office; fortunately, no Pet-injury occurred and palliative-care is not needed, per a veterinary-check-up, water and food . . . and YES the Registry Rescue Volunteer is paid the pre-authorized reward, per Registry-documentation, by pet-o-vet principals. The reward is charged to the Pet Parents one-of-two-credit-cards required for Animal Registration . . . the reward happily Pet Parent paid, for the volunteer's efforts per Care-ful animal delivery, and owner-reunion.

A more-rural setting is likely for our out-of-safe-zone animals, e.g., equine(s), likely not trucked-trailered to a veterinarian likely safe in a corral and/or stall per a neighborly-farmer-rancher; yet the reward and palliative-care assurances apply, should the registered equine need veterinary attention-intervention. Also, the more likely feline rescue scenario . . . finds our cat (dog, horse, donkey, etc.) identified by per system options, retina, etc.; the registry toll-free-number is called by the rescuer, and the rescuer is rewarded and guided to a convenient, local veterinary office, as the owner is also notified . . . therefrom the owner-feline reunion occurring . . . as Registered Companion Felines are as dearly-lifetime-loved as their fellow Registered Canine Companions, their rescue-reunions both hugely important . . . as to equines also.

Animal care, in addition to tasks and responsibilities, can and may be expensive. The FIG. 9 System and Method includes: "A)" Owner(s)-posthumous lifetime endowment for animal care, either by Last Will and Testament, Trust and/or per applicable law via FIG. 9 System and Method pro forma documentation(s); "B)" likewise per "A)", pooled resources from multiple sources to offset and/or defray veterinary and/or other animal care professionals, animal care, e.g. GoFundMe, grants, bequests, gifts, etc.; "C)" likewise per "A)", multiple bonding options . . . and/or granted-willed-given-other-sourced sums, for individual animals and/or groups of animals aid, comfort and well-being, are also resource-aggregation-options.

Animal Owner-Care Assistance: Having discussed how Animals are FIG. 9—System and Method smart-assisted, we turn our discussion-disclosures toward assisting Animal Owners' joys, cares and tasks. The FIG. 9 System and Method helps Registered Animal Owners with Pet care duties and tasks . . . through assisting Animal Owners in locating no-fee, reciprocal, and-or for-fee Animal Care Providers . . . and also through aligning Animal Owners interests and-or orientations for simpatico Care-ful animal care and task sharing and-or socializing, please see solitary notes.

The owner-steward's health and safety FIG. 9—System "knows" of the owners upcoming knee surgery, (mountain biking crashes, not scheduled) as "health animal care needs" could be one of The 99 Item Questionnaire's Background, Characteristics, Interests and Needs questionnaire items owners may optionally provide, per privacy protocols. Thus, our re-purposing FIG. 9—System "self-corrects" . . . re-purposing to researching-archiving location-relevant Care-ful Registrants, and-or Volunteers, for-fee/no-fee/other care options, whose "99 Profiles" tell of willingness "to dog-walk Animal-exercise during Owner-ailments-recoveries". Please note: love-of-Animals is a powerful motivational presence among Animal-caring-people! Also, 600 System computers, and 700 contractual big-data/other-databases-access, has screened owners per like interests and orientations, per Registrants (optional) Simpatico Scores. Thus, when the time comes for knee surgery, our Owner accesses the FIG. 9—System interests-needs-alignments, per big-data, /99 Questionnaire, for the Animal owner to select a simpatico dog walker, a cat-Care-ful-person, and-or an equine-exerciser. The most convenient per closest-location "Care-ful-walker" does not have the optional FIG. 9—System background report on file . . . so our knee surgery Owner, in upcoming need of dog-walking, selects an almost-as-convenient Care-ful-walker, with a FIG. 9—System background-report on-file. [All Registrant-Animal Care Providers-etc. information is selectively provided per privacy permissions, procedures and protocols.] #17

Animal Care Providers—Discussion: The experience of Animal care-givers is summarized and categorized by the FIG. 9—System—including the breed of equine—and the care-tasks performed, both by duties conducted, and the time-spans involved, e.g. Santa Anita Racetrack Stables—thoroughbred grooming, three race seasons (e.g. example not limiting). Thus, these summaries may vary from "daily feeding, exercise, brush-down of friend's quarter-horse—one summer" . . . to . . . "nine years—experienced in all aspects of stable management—multiple Arabians" . . . all analyzed, assessed, compiled, matched, sorted by the FIG. 9—System per Registrants "99-Item-Profile", internet alignments, big-data relevancies, and other information. (Professionals and persons offering canine-equine-feline expertise and-or services are likewise "scrubbed" by the Computer System.) Individuals who are Computer screened-selected by the System for Registered-Owners, and there-following System selections-per-Owner-profile-alignments, are interviewed by Animal Owners/Care-Principals to confirm a good System-driven "99 Items Simpatico Fit", both personally, and as to both duties and cat(s), dog(s), horse(s) involved.

FIG. 9—System alignments also screen all manner of Animal aficionados, from professionals to Animal-loving-volunteers, including those seeking others with whom to ride-walk-socialize. All information, per privacy principles-protocols, can and may include contacts and locations information-addresses-zip codes-private and-or published phone-text numbers-internet, email, texting connections-websites-social media-other connection-location-social-media relevant personal information-formats-means-to assist meeting Animal care needs, communications and-or joint-group activities and-or socializing—FIG. 9—System assembled per alignments and associations, by contacts and connections . . . per privacy protocols.

Please also note—in the same purposed/re-purposed/programmed/re-programmed/internal System-self-initiating-manner . . . by which the internet/big-data/other-sources, plus-internal-System capabilities, were aligned-orchestrated-executed, e.g. dog's hot-cab-rescue . . . in like DMSS-driven System-comprised, internally-initiated-purposed/multi-re-purposed self-correcting-learning-perfecting-manner . . . as-data-information-situation(s)-requires . . . so too are the computerized purposed/re-purposed/programmed/re-programmed System-assembled-FIG. 9

Care-ful Simpatico Personal Alignments and Associations System-assembled; ("Simpatico" alignment(s)-association(s) defined; persons of like-minds, similar and-or complementary backgrounds, animals, dispositions, experiences, and social orientations.) #18

FIG. 9—System and Method: 500, 600, 700, 800 Integrated-per-900—an iteration of the systems and/or methods (processes) summarized above:

1. The Computer System includes all communications capabilities-devices, including smart and wearable . . . (singulars can and may be plurals and-or combinations thereof)
2 . . . . via all communication means, media, methods, modes, e.g. signal flags to internet, analog to digital, wire to optical, etc.
3 . . . . to-from communicating per all human and/or animal devices-monitors-sensors-sources
4 . . . . and System computers-platforms-processors-programs-servers and/or to-from communicating-transmitting computers and/or computerized-System components, and/or devices-monitors-sensors-sources . . . can-may range in size and capacity from nano-micro-mini computer(s)-computerized devices, to all-size-and-capacity computers/banks of computers/networks/servers/cloud(s) computing
5 . . . . and human-owners-stewards/designates of animals, and owners-animals' health-centric/otherwise employed computer-computerized system(s) maintained archives-databanks-registries
6 . . . . via computers, (nano-technologies) nano/micro/mini/full-sized/integrated-clouds and smart computerized communicating-transmitting devices, laptops, phones, tablets, wearables, and communication(s)-transmission(s) technologies
7 . . . . including (yet not limited to) short range to-from communications-signals-transmissions and-or long-range to-from communications-signals-transmissions and-or short-range-signal(s) gathered-boosted-signal-strengthened-to-long-range to-from transmission(s)-communication(s)
8 . . . . short range to-from signals-communications-transmissions gathered and range-boosted-increased-strengthened to long range communications per #2 as expedient-necessary for to-from-long-range-communication(s)-transmission(s)
9 . . . . communications regarding all life sustaining-threatening-terminating bodily ailments, conditions, functions health, processes, situations
10 . . . . and animal ailments, diseases, their markers, indices, profiles, symptoms and administrations-procedures-treatments
11 . . . . per animal healthy/unhealthy behaviors, biologies, chemistries, indices, markers, profiles, processes, protocols, symptoms and-or other computer system(s)-included ailment(s)-disease(s)-indexes-indices-marker(s), per devices-monitors-sensors-sources-capabilities within FIG. 9—System . . . and-or also animal health-impacting data-information sourced remotely from System, e.g. NOAA—hurricanes, commercial media weather forecasts . . . e.g. examples throughout not limiting capabilities, options, responses and treatments . . . #19
12 . . . . systemically inclusive of devices-monitors-sensors-sources in-animal/implanted/ingested/inserted, and-or on-animal-bridle-collar-garment-halter-harness-hackamore-gear-tack-trappings, bespoke and-or multiple-manufactured-units borne—and/or from sources via #2 (e.g., archives, media, NOAA, yet not limited thereto) remote from the body/bodily processes
13 . . . . with the devices-monitors-sensors-sources and associated-to-from-communication(s)-transmission(s) functionally interfaced-integrated
14 . . . . on-and-or-in-and-or-remote-from-body-bodily-processes per #12, and-or remote from animal-and-or-body-bodily-processes-assessing-computer(s)-cloud(s), computerized device(s), and/or on/in-animal-body smart-nano-micro-mini-computer(s)-computerized-device(s) to-from-communication(s)-transmission(s)-computer(s)-devices-monitors-sensors-sources analytical-health-assessment-capabilities
15 . . . . being non-remotely and-or remotely and-or FIG. 9—System-internally-initiated, and-or purposed/re-purposed/multi-re-purposed, configured and-or re-configured, programed and-or re-multi-programed, platformed and-or re-platformed, enabled and-or re-enabled, focused and-or re-focused, tasked and-or re-tasked per a computer(s)-cloud(s)-computerized-device(s) with-without to-from-communicating(s)-transmission(s) capabilities
16 . . . . per the health, safety, ailment, disease, life sustaining-threatening terminating, and-or gradations thereof, and-or other bodily functions-impacts-results
17 . . . . for which devices-monitors-sensors-sources healthful-unhealthful-gradations-thereof data-information is sought . . . e.g. blood-glucose markers and-or sepsis symptoms sought, etc., e.g. not limiting
18 . . . . either not-remotely, and-or remotely input, and-or per FIG. 9—System-internally-initiated, per to-from DMSS-data-information-driven communication(s)-transmission(s) . . . initially purposed-programed for kidney function analytics-assessments sought, per System-internally-initiated self-correction per DMSS-data-information by monitor-sensor-read, re-purposed/re-programmed/corrected to heart-ailment analysis-assessment ailment-profile and-or treatment-protocols. Thus, System-self-corrected heart ailment assessed per life sustaining-threatening-terminating DMSS-sensed-data-information-markers-indicators, e.g. to cite a likely hypothetical initial kidney-functions to heart ailment System-self-correction re-purposing—System-internally-initiated self-correction re-purposed/re-programed, per-System-DMS(S) data-information-read, thereby System-self-corrected to heart ailment-assessment-analytics—e.g. not by-example-limiting 19 . . . . the device-monitor-sensor-(source) data-information being reported to computer-aligned-archive of animal owners/veterinarians/designates and-or other entities—and-or optionally alarm-noticed-per-data-read-assessment-analytics to animal-owner-steward/veterinarian(s)/care-principal(s)

20 . . . . System-internally-initiated-self-correction per monitor(s)-sensor(s)-data-read, purposed/re-purposed/self-corrected-per granular data . . . from kidney-inquiry . . . to heart analysis-assessment . . . #20

21 . . . . per the healthy-and-or-not-healthy-ailments-diseases-profiles-indices-markers-symptoms for which vital animal health-status data-information is purposed/re-purposed, sought/re-sought, perfected/re-perfected, per System analytics-assessments 22 . . . . in this document, Veterinary example, the System analytically-internally-initiated/purposed/re-purposed/self-corrected per kidney data-information sought . . . being re-purposed per computer-program-platform-processor-server . . . purposed/re-purposed/processed/re-processed, programed/re-programed, profiled/re-profiled per DMSS-data-information analytically assessed per vital animal life sustaining/threatening/terminating bodily processes, (and-or other assessments-gradations-thereof) . . . per DMSS-driven (device-monitor-sensor-source) health-data-information, analytically-assessed . . . System-self-corrected to heart ailment indices-markers-profiles . . . and-or other ailment profiles per DMSS-driven analytics 23 . . . . and optionally alarmed-noticed-reported to the In-System-Registered-Animal-Owner/Veterinarian(s)-Principal-Care-Designate(s), per ailment-disease life-threatening-assessment 24 . . . . and-or human-to-animal-applied medical-veterinary assessments, ailments, conditions, diseases, indices, markers, treatments 25 . . . . and-or programed/re-programed, purposed and-or re-purposed assessments-conditions-profiles solely by System-initiated 26 . . . . and-or therewith human-programmers, and-or by human-programmers-solely-of-themselves, and-or in human-and-System self-correcting, purposing/re-purposing/programing/re-programing system-self-correcting human-System combination(s)

27 . . . . as device-monitor-sensor-data-information-read may discern, e.g. a heart-ailment-profile-inquiry, and re-program/re-purpose the device-monitor-sensor and-or all-of-System-therefor 28 . . . . self-correcting the initial program/re-program, purpose/re-purpose of the kidney-functions-ailments-profiles inquiry sought 29 . . . . per System internally-initiated capabilities—and-or per human programmers-programming—assessment per device-monitor-sensor-data-read—re-purposed as a heart-ailment-profile per data, rather than a kidney ailment profile per initial inquiry 30 . . . . thereby System-self-correction re-purposing the System assessment programming, per device-monitor-sensor-data-information feedback, to a heart-ailment-profile 31 . . . . multiple System-self-correction outcomes being possible, e.g. kidney and heart and other ailments 32 . . . . archived-reported granular device-monitor-sensor data-information allowing veterinary assessments/re-assessments/confirmations . . .

3 . . . . the proven-on-animals System being applicable to humans subject to MD-Specialist oversight . . . .

Example of total Canine Olfactory Bodily Response Assessment—per FIG. 9—System and Method—Guard Dogs, War/Military Dogs, Police Dogs, Rescue Dogs: Olfactory canine trainers consider Total Bodily Response as useful in two situations. The first is pre-training/culling, that is—does a canine have the native dispositions well suited to olfactory tasks and training . . . assessed per how the training-candidate-dog responds to both human scents, predisposing to human search and rescue tasking . . . and/or how the candidate-dog responds to different drug-scents, predisposing to police and law enforcement tasking and training. The second useful purpose of total bodily responses . . . general agitation, panting, barking . . . is assessing general progress per olfactory task-training.

While the selected candidate-dog(s) inherently exhibit visual indicators, such as general agitation, panting, barking, etc., that presupposes that the candidate-dog(s) is within visual observation, either by a human presence or remotely, e.g., by use of a camera. The present system and/or method permits machine observation alone and/or implemented with the use of AI to discern the meaning of the candidate-dog(s) total bodily responses. The following example describes the use of AI assisted total bodily responses.

A harness of any of the types illustrated in FIGS. 1C-1F can be attached to the candidate-dog. The harness is responsive to various DMSS as described above. The candidate-dog senses are challenged one at a time, e.g., the olfactory sense with the senses of hearing, sight, touch being eliminated/blocked by physical shields, i.e., earplugs, eye-masks, etc. By challenging the candite-dogs olfactory sense alone, e.g., various scents, e.g., smoke, human cadaver, oil, illegal drugs/contraband, being utilized to evoke a response and recording/analyzing/archiving the data from the DMSS, while at the same time visually recording/analyzing and archiving the total bodily response, a machine-readable response will be emitted for each of the challenges to the candidate-dog olfactory sense. By repetition of the challenges utilizing at least some of the same scents as well as new scents, a library of data can be compiled for each of the candidate-dog(s) total bodily responses. By similarly challenging each of the candidate-dog(s) responses to other senses, e.g., sight, sound, etc., while blocking other senses, a library of other total bodily response can be prepared from each challenge to the candidate-dog(s) individual senses. Finally, some and/or all of the candidate-dog(s) senses can be challenged without restricting one or more other senses, i.e., olfactory, sight and sound senses can be challenged together, while also obtaining and recording/analyzing/archiving the total bodily response of the candidate-dog while simultaneously under visual observation which is also recorded/analyzed/archived, the data received from the sensor can be interpreted, not by human observation, but with the use of AI. Once the library for each candidate-dog is established, it will be no longer necessary to have the total bodily responses of the candidate-dog under human observation, as the data received from the DMSS sources for each candidate-dog will be interpreted by AI. Thus, individual guard dogs, war/military dogs, police dogs, rescue dogs will no longer be required to be under human observation, but can work independently outside of human observation, with the data from the DMSS being recorded/analyzed/archived by the AI. The AI can be implemented to inform a human handler of the candidate-dog that the dog has, or has not, completed its mission, e.g., location of snow-covered person(s) caught in an avalanche.

The preceding system disclosure is suitable for one, more than one, or a plurality of simultaneous monitoring and sensing capabilities and/or devices for the following animal bodily processes and systems, practices and procedures, while not e.g. limited to the following supplemental examples, e.g.: 1) microfluidics . . . 2) photo-video image detection techniques . . . 3) sound analytics (coughing—contagion) . . . 4) sweat and salivary sensing . . . 5) wearable technologies . . . 6) nano-biosensors . . . 7) serodiagnosis . . . 8) infectious disease detection . . . 9) communicating devices, monitors and sensors/sources . . . 10) molecular biology diagnostics . . . 11) bio-chem sensors . . . 12) internal body temperature and/or ambient temperature measurement, logging and notification . . . 13) metabolites monitoring . . . 14) breath-breathing analysis/monitoring . . . 15) implanted, ingested & inserted devices, monitors and sensors . . . 16) medication patches . . . 17) tracking/location programs . . . 18) behavior and movement monitoring . . . 19) pH detection . . . 20) stress detection . . . 21) sound analytics . . . 22) analytes detection . . . 23) virus-pathogen detection . . . 24) contagion detection & prevention—culling diseased animals . . . 25) solar powered health monitors transmitting data to computer-archives . . . 26) ear attached bio-sensing devices measuring body temperature/other signs . . . 27) iontophoretic drug delivery . . . 28) patched and under-skin devices, treatments . . . 29) antibiotic biosensor detection of subtherapeutic usage causing antibiotic resistance preventing enteric and respiratory disease treatments . . . 30) Maximum Residue Limits biosensors for pharmacologically active antibiotic substances and metabolites . . . 31) integrated data measurements and data acquisition systems via biosensors and monitors producing real-time-rapid health and treatment solutions, and rapid responses to animal-human contagion, including in situ . . . 32) rapid detection of the presence or absence of biomarkers and specific chemicals of life-death importance, e.g. the monitoring of glucose or protein or enzymes or sepsis in the bloodstream . . . 33) bio-nanotechnology and microelectronics make possible the fabrication of transistors smaller than 100 nm & integrating several hundred 100 nm transistors into functional program-platform analytic circuitry via micro-chips . . . 34) microfluidics technology for the rapid detection of analytes . . . 35) thermoplastic and paper based chips have revolutionized disease diagnostic platforms and programs . . . 36) integration of microfluidics and florescent label ensures minimum sample volume and enhancement of sensitivity . . . 37) microfluidics—allows spatial and temporal resolution plus differentiation between non-hybridizing and hybridizing oligomers of DNA, #22 38) surface plasmon resonance—multiple SFR platforms now operational . . . 39) portable SPR device detects antibiotics . . . 40) very accurate screening achieved via digital microfluidics and SPR . . . 41) non-invasive sweat analytics—monitors sodium, potassium, lactate, glucose and skin temperature—blue tooth integrated plus other technologies, communications and analytics . . . 42) diagnosis of diabetic ketoacidosis . . . 43) radio-frequency identification tracking of health related behaviors . . . 44) total quality health management principles substantially benefit animal well-being . . . 45) sweat analytics—pH, CL, Na, glucose, ethanol, lactate, ammonium, electrolytes—sodium, potassium ions, zinc, ions—($Na+$, $CL-$, K═, $NH4+$), cortisol, urea, peptides—neuropeptides & cytokines, calcium . . . 46) pathogen detection—biosensor-based imaging ellipsometry . . . 47) wasting disease detection requires 24 hour audio-video monitoring—cough-sound detected via audio analysis and motion detection . . . 48) temperature—body core & major organs temperature monitored by rectal, vaginal, vascular and digestive-tract monitors and sensors . . . 49) mid-peripheral temperature—monitored by intra-muscular chips . . . 50) peripheral-skin temperature—monitored by skin-embedded micro-chips and through fur-hair skin-contacting multiple sensor probes . . . 51) saliva analytics—as breath and sweat-non-invasive . . . 52) electro-chemical and bio-metric devices, monitors and sensors communicate analytic health data to computer programs and/or platforms integrated and/or interfaced . . . 53) animal-to-human contagion—real-time device, monitor and sensor detection of zoonotic diseases speeds public health contagion and veterinary-medical treatment protocols.

The "Bonded Registry" comprises a system wherein a bond is posted by the owners/principals/officers/managers (depending on the business form) to guarantee care to a registered animal in the form of compensation for any, or all of, housing/transporting/food veterinary care/as well as rewards/remunerations to those persons locating a lost/missing animal from the time of first locating the animal to the time of reunion with the registered owner (or his designate). Unlike the many "pet insurance scenarios" in the pet marketplace, the Bonded Registry does not require the registered owner to purchase and maintain insurance. Rather, the risk on costs/remunerations, etc. are borne by the Bonded Registry with the amount of the bond, as initially determined by the Registry and the owner of the registered animal(s), upon initial registration of the animal(s). This assures that the Bonded Registry has lower risk, and pet owners have lower rates as compared to pet insurance programs.

The understanding of the present disclosure may be better understood by the following additional Examples. FIG. 8 Action Options 140: per raw data link 120, or per platform-program processed data 127, link 121 and/or archive data 127, link 121, multiple actions 140 are undertaken; Examples follow:

ADDITIONAL EXAMPLES

Example 1

An animal, such as an equine, may be away from its stable, when a signal is generated by external DMSS 101. That signal could be detection of hazardous environmental conditions, such as wind-borne traces of harmful agricultural chemicals, e.g., pesticide. The signal from DMSS 101 (FIG. 8) is transmitted to communication device 110. The communication device 110 (for example, medallion 10 and/or 24) will transmit a signal 120 to a location remote from the animal, such as to an owner/stable/veterinarian or other principal designate 125. The signal 120 may also be automatically directed, via 126, directly to an archive 127, or may be manually directed to archive 127, via 121, by the owner/stable/veterinarian 125. If the exposure of the equine to the harmful agricultural chemical requires immediate action, the owner/stable/veterinarian or other designate can retrieve the animal, optionally with the aid of GPS, or other animal locating technologies. Also, 127, via 121 feedback(s), per archive and/or platform(s) and/or program(s) to 125 can and may cause owner/principal/designate to undertake 140 remedial actions; 150, 151, 152, 153, 160, 162,164, 168, 175 are action option(s) examples-action options are not limited to the Examples.

Example 2

Similar to the scenario of Example 1, the DMSS 101 receives a source, such as a NOAA, county, or other governmental advisory of hazardous weather conditions, e.g., high winds, tornado, etc. The signal from DMSS 101 (FIG. 8) is transmitted to communication device 110. The communication device 110 (for example, medallion 10, 24 and/or 210) will transmit a signal 120 to a location remote from the animal, such as to an owner/stable/veterinarian or other designate 125. The signal 120 may also be automatically directed, via 126, directly to an archive/platform(s)/program(s) 127 or may be manually program/platform directed to archive 127, via 121, by the owner/stable/veterinarian/or other designate 125 per program and/or platform. If the exposure of the equine to the hazardous weather conditions requires immediate action, the owner/stable/veterinarian or other designate can retrieve the animal, optionally with the aid of GPS, or other animal locating technologies.

Please note—FIG. 8, 140, Multiple Action Options: Actions can and may be undertaken to protect the health, safety and general well-being of individual Furry Family Members, beloved polo steeds, and pampered thoroughbreds with syndicated ownerships. Yet device(s)/monitor(s)/sensor(s)/sources(s) ("DMSS") information impacting the health and safety of animals can and may also impact animals in multiple U.S. Zip Codes, counties, states, whole regions, with DMSS information impacting Registry-Included Animal(s)-Ownership(s)-Designate(s)-Principal-Steward(s). Please consider . . . thoroughbred horses with multiple-global ownerships, plus the likes of SPCA rescue kennels nationally, and the impacts of recent NOAA sourced tornado warnings, with following destruction and death, as it impacted-impacts thoroughbred farms principal steward's horses, plus rescue canine and feline facilities nationwide; tornadoes (and all manner of extreme environmental conditions, summer heat waves to winter artic air moving south) regularly cause widespread death and suffering, plus extreme emotional and financial losses, across the equine-feline-canine U.S. realm. Thus, the importance of FIG. 8, 140, per DMSS Multiple Animal Health and Safety Action Options, as environmentally (and generally) defined . . . urgent per zip code-county-state-region DMSS advisories, via all communication devices and methods, to Health and Safety System Database-Included Animals-Owners-Designates-Principal Stewards, causes DMSS powered actions, so animals are not being killed by the likes of seasonal heat and seasonal tornadoes. DMSS Health and Safety System Generated Information . . . from sepsis sensed in the individual beloved Furry Family Member, to tornadoes forecast across a vast five-state-region impacting thousands of animals; DMSS Health and Safety System Generated Information powers and sustains animal well-being.

Example 3

As in Example 1, an animal, such as an equine, may be away from its stable, when a signal is generated by near the DMSS 104. DMSS 104 can detect multiple life-threatening or life-sustaining signs or conditions of the animal. In this example, DMSS detects high blood sugar signs or conditions in the equine. Again, this animal sign or condition will be transmitted, via link 97 to communication device 110. Alternatively, if the signal generated by DMSS 104 needs to be modified, it can be first submitted to signal processing 113 and the signal processed DMSS signal is the communicated to the communication device 110 via link 98. Once the communication device receives a signal (via either link 97 or 98) the communication devices communicate, via link 120, to the owner/stable/veterinarian or other designate 125. If the owner/stable/veterinarian or other designate 125 determines that the high blood sugar requires immediate medical intervention, a communication is sent to the communication device 150, via link 140, to administer insulin.

Communication device 150, via link 151, instructs the pharmaceutical dispenser 160 to administer a dose of insulin directly to the animal. Links 120-126-121 per archive(s) and/or program(s) and/or platform(s) interfaced and/or integrated 127, may also per feedback link 121, redirect to 125 per multiple action options 140.

Example 4

In connection with the canine 71, fitted with a harness-strap design of FIG. 1D, the other sensor 103, FIG. 8 determines that the canine is in a no-safe zone, e.g., it has left its yard enclosure and cannot be found therein or nearby. When acting as a GPS, or other technology location, sensor 103 sends a signal, via link 99, to communication device 110, which in turn is communicated remote from the animal, via link 120, to the owner/veterinarian or other designate 125. The owner/veterinarian or other designate can then send a communication, via link 140, to the communication device, which in turn, can activate one, or more, of lights 162, energize ambient video 164, open two-way voice 175, and determine the severity of danger in the no-safe zone. Feedback can be provided, via the links 168 and/or 169, providing additional information through communication device 110 to the owner/veterinarian or other designate to further determine the danger to the canine. Appropriate action can then be taken by the owner/veterinarian or other designate, including the administration of a medicament, eg, a sedative, via the pharmaceutical dispenser 81 of FIG. 1D. Feedback link 121 also can and may per 127 redirect DMSS to 125 for other 140 action options.

Example 5

With regard to canines, especially when the canine is in freezing or sub-freezing weather, DMSS 104 can sense animal temperature (e.g., one of core temperature, skin temperature, or both), before onset of life-threatening hypothermia, and send a signal, via link 97 to communication device 110, which, in turn, via link 120, can activate a smart phone, a wearable or other device warning the owner/veterinarian or other designate that the canine is in distress. Response from the owner/veterinarian or other designate can include the administration of medicament, e.g., adrenaline, via pharmaceutical dispenser 81 of FIG. 1D, as well as activating HHHB sourced body covering heating elements.

While these examples are provided merely to illustrate potential methods of use of the Equine Health and Safety System and Method of this disclosure, they are to be viewed as merely exemplary, and not limiting, as numerous other uses are identified herein, and other uses of the Equine Health and Safety System and Method may be readily apparent to those of ordinary skill in the art, after reading this disclosure and the appended claims.

As used herein, we have identified families of animals, e.g., equine, canine and/or feline, and specific species therein, e.g., horse, dog, and cat. However, this identification was for exemplary and non-limiting purposes. It should be expressly noted that the term "animal" with respect to the present application comprises all companion animal(s), thoroughbred horses, as well as other horses, ponies, mules, donkeys, and ungulates in general, or any other animal (excluding humans) that can benefit from the herein disclosed Animal Health and Safety System and Method.

As used herein, communications and transmissions are via all types of modes, antenna, equipment, communication(s)-device(s), analog and digital, and all transmission methods/frequencies (e.g., microwaves, optical, etc.) and modes. As noted herein, no explanation, example, embodiment or illustration shall serve to limit the invention which is defined by the appended claims.

As used herein, the singular, e.g., device and/or sensor, may also denote the plurals, e.g., devices and/or sensors, and vice-versa.

It is also within the scope of the disclosure, that two or more elements, as disclosed herein, can be combined into one element, with multiple functions. It is also to be understood, that a single element, as disclosed herein, may be divided into two or more elements without the exercise of inventive effort and therefore are within the scope of the present disclosure.

It should also be appreciated that this specification and appended claims are directed to those persons of ordinary skill in the art to which this disclosure pertains and is not limited to the exemplary or preferred embodiments disclosed herein. It will also be apparent to those same persons skilled in the art that various modifications may be made, and technologies employed, without departing from the appended claims.

I claim:

1. An animal health and safety system comprising at least one device/monitor/sensor/sources (DMSS) to generate data-information directly from a living animal;

a communication device configured to communicate the generated data-information obtained directly from the living animal for at least one purpose selected from the group consisting of logging, serve, advise, alert, analyze, assess, administration(s), diagnose, evaluate, treatment(s), procedures, monitor, archiving, and research, for the well-being of the living animal, via platforms and/or programs;

wherein the at least one device/monitor/sensor/sources (DMSS) to generate the data-information is configured to monitor or sense the living animal to obtain the data-information:

the data-information obtained directly from the living animal is from at least one device/monitor/sensor/sources (DMSS) selected from the group consisting of microfluidics, nano-fluidics, sound analytics, nano-biosensors, serodiagnosis, infectious disease detection, molecular biology diagnosis, biochem sensors for enzymes or sepsis, sensors configured for ocular, neural, and brain analytic health data, sensors configured for breath analysis, sensors configured for saliva analytics, sensors configured to detect kidney functions, sensors configured to detect liver functions, sensors configured for digestive functions, sensors configured for reproductive functions, sensors configured to detect health data of bone or integumentary components selected from the group consisting of hair, fur, hooves, and claws, virus-pathogen detectors, sensors configured for contagion detection and prevention, iontophoretic drug delivery, antibiotic biosensor detection of sub-therapeutic usage causing antibiotic resistance preventing enteric and respiratory diseases, maximum residue limit biosensors for pharmacologically active antibiotic substances and metabolites, surface plasmon resonance (SPR)-multiple platform, sensors configured to detect animal-to-animal contagion, and sensors configured for real time animal-to-human contagion detection of zoonotic diseases.

2. The animal health and safety system of claim 1, wherein the at least one device/monitor/sensor/sources (DMSS) to obtain data-information directly from the living animal is borne by a body covering in contact with the animal.

3. The animal health and safety system of claim 2, further comprising embedding, implanting, inserting or ingesting at least one additional device/monitor/sensor in the living animal.

4. The animal health and safety system of claim 1, wherein the microfluidics is one selected from the group consisting of microfluidics for the rapid detection of analytes, breath and salivary sensing.

5. The animal health and safety system of claim 4, wherein the microfluidics is for breath or salivary sensing and comprises the sensing of at least one of protein or hormone levels, pH, Cl, Na, ethanol, ammonium, electrolytes-sodium, potassium ions, zinc, cortisol, urea, peptides-neuropeptides, cytokines, heavy metals, and calcium.

6. The animal health and safety system of claim 1, wherein the at least one device/monitor/sensor/sources (DMSS) within the group consisting of at least one device/monitor/sensor/sources performs multiple functions.

7. The animal health and safety system of claim 1, wherein the data-information obtained directly from the living animal from the at least one device/monitor/sensor/sources (DMSS) is to analyze, assess, diagnose, and evaluate the well-being of the living animal.

8. The animal health and safety system of claim 1, wherein the at least one device/monitor/sensor/sources (DMSS) to obtain data-information directly from the living animal is selected from the group consisting of nano-fluidics and nano-biosensors.

9. The animal health and safety system of claim 8, wherein the nano-fluidics is one selected from the group consisting of nano-fluidics for the rapid detection of analytes, breath and salivary sensing.

10. The animal health and safety system of claim 1, wherein the at least one device/monitor/sensor/sources (DMSS) to obtain data-information directly from the living animal is selected from the group consisting of contagion detection and prevention, virus-pathogen detection, animal-to-animal contagion, and animal-to-human real-time detection of zoonotic diseases.

11. The animal health and safety system of claim 10, wherein the at least one device/monitor/sensor/sources (DMSS) to obtain data-information directly from the living animal detects mink Covid-to-human transmission, Chronic Wasting Disease (CWD) or Mad Cow Disease (BSE).

12. The animal health and safety system of claim 1, wherein the at least one device/monitor/sensor/sources (DMSS) to obtain data-information directly from the living animal is maximum residue limit biosensors for pharmacologically active antibiotic substances and metabolites.

13. The animal health and safety system of claim 1, wherein the at least one device/monitor/sensor/sources (DMSS) to obtain data-information directly from the living animal is selected from the group consisting of molecular biology diagnosis, biochem sensors for enzymes or sepsis, virus-pathogen detection, and contagion detection and prevention.

14. The animal health and safety system of claim 1, wherein the at least one device/monitor/sensor/sources (DMSS) to obtain data-information directly from the living animal is configured to detect ocular, neural, or brain analytic health data-information from the living animal.

15. The animal health and safety system of claim 1, wherein the at least one device/monitor/sensor/sources (DMSS) to obtain data-information directly from the living animal is an antibiotic biosensor detector for sub-therapeutic usage causing antibiotic resistance preventing enteric and respiratory diseases.

16. The animal health and safety system of claim 1, wherein the at least one device/monitor/sensor/sources (DMSS) to obtain data-information directly from the living animal is configured to detect at least one selected from the group consisting of serodiagnosis, iontophoretic drug delivery and molecular biology diagnosis.

17. The animal health and safety system of claim 1, wherein the at least one device/monitor/sensor/sources (DMSS) to obtain data-information directly from the living animal is surface plasmon resonance (SPR)-multiple platform.

18. The animal health and safety system of claim 1, wherein the at least one device/monitor/sensor/sources (DMSS) to obtain data-information directly from the living animal is sound analytics.

19. The animal health and safety system of claim 1, wherein the at least one device/monitor/sensor/sources (DMSS) to obtain data-information directly from the living animal is configured to obtain at least one from the group consisting of kidney functions, liver functions, digestive functions, and reproductive functions.

20. The animal health and safety system of claim 1, wherein the data-information obtained directly from the living animal from the at least one device/monitor/sensor/sources (DMSS) is configured to alert for the well-being of the living animal.

21. The animal health and safety system of claim 1, wherein the data-information obtained directly from the living animal from the at least one device/monitor/sensor/sources (DMSS) is communicated to a smart device or wearable.

22. The animal health and safety system of claim 1, wherein the living animal is a canine.

23. The animal health and safety system of claim 1, wherein the living animal is an ungulate.

* * * * *